US008772314B2

(12) United States Patent
Amari et al.

(10) Patent No.: US 8,772,314 B2
(45) Date of Patent: Jul. 8, 2014

(54) GLYCINE DERIVATIVES AND MEDICINAL COMPOSITIONS THEREOF

(75) Inventors: Gabriele Amari, Parma (IT); Mauro Riccaboni, Parma (IT); Marco Farina, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 352 days.

(21) Appl. No.: 13/303,413

(22) Filed: Nov. 23, 2011

(65) Prior Publication Data

US 2012/0134934 A1 May 31, 2012

(30) Foreign Application Priority Data

Nov. 26, 2010 (EP) ..................................... 10192713

(51) Int. Cl.
*A61K 31/44* (2006.01)
*C07D 453/02* (2006.01)

(52) U.S. Cl.
USPC .......................................... 514/305; 546/137

(58) Field of Classification Search
USPC .......................................... 546/137; 514/305
See application file for complete search history.

(56) References Cited

U.S. PATENT DOCUMENTS

| | | | |
|---|---|---|---|
| 8,039,483 B2 | 10/2011 | Amari et al. |
| 2010/0173880 A1 | 7/2010 | Caligiuri et al. |
| 2011/0311458 A1 | 12/2011 | Amari et al. |
| 2011/0311459 A1 | 12/2011 | Amari et al. |
| 2011/0311461 A1 | 12/2011 | Amari et al. |

FOREIGN PATENT DOCUMENTS

| | | | |
|---|---|---|---|
| WO | 9521820 | * | 8/1995 |
| WO | 99/10312 | | 3/1999 |
| WO | 2010/072338 | | 7/2010 |

OTHER PUBLICATIONS

U.S. Appl. No. 13/729,388, filed Dec. 28, 2012, Amari, et al.
European Search Report in Application No. 10192713.5, issued Mar. 10, 2011.

* cited by examiner

*Primary Examiner* — Niloofar Rahmani
(74) *Attorney, Agent, or Firm* — Oblon, Spivak, McClelland, Maier & Neustadt, L.L.P.

(57) ABSTRACT

Alkaloid aminoester derivatives according to formula (I) and (VI) act as muscarinic receptor antagonists.

12 Claims, No Drawings

GLYCINE DERIVATIVES AND MEDICINAL COMPOSITIONS THEREOF

CROSS REFERENCES TO RELATED APPLICATIONS

This application claims priority to European Patent Application No. 10192713.5 filed on Nov. 26, 2010, which is incorporated herein by reference in its entirety.

BACKGROUND OF THE INVENTION

1. Field of the Invention

The present invention relates to glycine derivatives which act as muscarinic receptor antagonists. The present invention also relates to processes for the preparation of such a glycine derivative, compositions which contain such a glycine derivative, and therapeutic uses of such a glycine derivative, as well as devices which contain such a glycine derivative and combinations which contain such a glycine derivative.

2. Discussion of the Background

Quaternary ammonium salts which act as muscarinic (M) receptor antagonist drugs are currently used in therapy to induce bronchodilation for the treatment of respiratory diseases. Examples of well known M receptor antagonists are for instance represented by ipratropium bromide and tiotropium bromide.

Several chemical classes which act as selective M3 receptor antagonist drugs have been developed for the treatment of inflammatory or obstructive airway diseases such as asthma and chronic obstructive pulmonary disease (COPD).

Quinuclidine carbamate derivatives and their use as M3 antagonists are disclosed e.g. in WO 02/051841, WO 03/053966, and WO 2008/012290, which are incorporated herein by reference in their entireties.

Said M and M3 receptor antagonists are currently administered through inhalation route in order to deliver the drug directly at the site of action, thus limiting the systemic exposure and any undesirable side effect due to systemic absorption. However, even though the systemic exposure may be reduced through the inhalatory route, the compounds of the prior art may still, at least potentially, exhibit undesired side effects due to systemic absorption. Therefore, it is highly desirable to provide M3 receptor antagonists which are able to act locally, while having high selectivity and plasmatic instability. Said drugs, once adsorbed, are degraded to inactive compounds which are deprived of any systemic side effects typical of muscarinic antagonists.

WO 2010/072338, which is incorporated herein by reference in its entirety, describes azonia-bicyclo[2.2.2]octane compounds which act as muscarinic receptor antagonists, further possessing the above therapeutically desirable characteristics.

SUMMARY OF THE INVENTION

Accordingly, it is one object of the present invention to provide novel compounds which act as muscarinic receptor antagonists.

It is another object of the present invention to provide novel processes for the preparation of such a compound.

It is another object of the present invention to provide novel compositions which contain such a compound.

It is another object of the present invention to provide novel therapeutic uses of such a compound.

It is another object of the present invention to provide novel devices which contain such a compound.

It is another object of the present invention to provide novel combinations which contain such a compound.

These and other objects, which will become apparent during the following detailed description, have been achieved by the inventors' discovery that glycine derivatives of general formula (I) or (VI) described below act as muscarinic receptor antagonists.

Thus, in a first embodiment, the present invention provides glycine derivatives of general formula (I) or (VI) described below.

In another embodiment, the present invention provides processes for the preparation of a glycine derivative of general formula (I) or (VI) described below.

In another embodiment, the present invention provides compositions which contain a glycine derivative of general formula (I) or (VI) described below.

In another embodiment, the present invention provides certain therapeutic uses of a glycine derivative of general formula (I) or (VI) described below.

In another embodiment, the present invention provides combinations of a glycine derivative of general formula (I) or (VI) described below with one or more other pharmaceutical active ingredients among which are, for instance, those currently used in the treatment of respiratory disorders, e.g. beta2-agonists, corticosteroids, P38 MAP kinase inhibitors, IKK2 inhibitors, FINE inhibitors, PDE4 inhibitors, leukotriene modulators, NSAIDs, and mucus regulators.

Surprisingly, it has been now found that the glycine derivatives of general formula (I) or (VI) described below, improve even further the selectivity and plasmatic instability with respect to other compounds, with the consequent minimization of side effects.

The compounds of the present invention thus behave as soft-drugs, since they are able to produce a more persistent bronchodilating effect in the lungs but are more consistently and rapidly transformed into inactive metabolites after passing into human plasma. This behavior gives great advantages in terms of safety.

DETAILED DESCRIPTION OF THE PREFERRED EMBODIMENTS

In particular, the invention is directed to glycine derivatives of general formula (I)

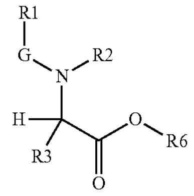

(I)

wherein:

R1 is selected from the group consisting of —H, linear or branched $(C_1-C_{10})$alkyl, $(C_2-C_6)$alkenyl, aryl, $(C_3-C_8)$cycloalkyl, $(C_5-C_{10})$heterocycloalkyl, aryl$(C_1-C_6)$alkyl, and heteroaryl, optionally substituted by one or more substituents selected from the group consisting of halogen atoms, —OH, oxo(═O), —SH, —$NO_2$, —N(R5)(R8), —CN, —$CON(R5)_2$, —NHCO(R5), —COR5, —$CO_2R5$, $(C_1-C_{10})$alkylsulfanyl, $(C_1-C_{10})$alkylsulfinyl, $(C_1-C_{10})$alkylsulfonyl, $(C_1-C_{10})$alkyl, $(C_1-C_{10})$alkylcarboxyl, $(C_1-C_{10})$alkoxy, aryl, aryloxy, and heteroaryl;

G is selected from the group consisting of —OC(O)—, —$SO_2$—, and —C(O)—;

R2 is selected from the group consisting of —H, ($C_1$-$C_{10}$)alkyl, and aryl($C_1$-$C_6$)alkyl, optionally substituted by one or more substituents selected from the group consisting of halogen atoms, —OH, oxo(═O), —SH, —$NO_2$, —N$(R5)_2$, —CN, —CON$(R5)_2$, —NHCO(R5), —CO(R5), —$CO_2$(R5), ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, and heteroaryl;

R3 is selected from the group consisting of —H, ($C_1$-$C_{10}$)alkyl, aryl, ($C_3$-$C_8$)cycloalkyl, heteroaryl, aryl($C_1$-$C_6$)alkyl, and heteroaryl($C_1$-$C_6$)alkyl, optionally substituted by one or more substituents selected from the group consisting of halogen atoms, —OH, oxo(═O), —SH, —$NO_2$, —N$(R5)_2$, —CN, —CON$(R5)_2$, —NHCO(R5), —CO(R5), —$CO_2$(R5), ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, aryl($C_1$-$C_{10}$)alkylenoxy, and heteroaryl;

R6 is selected from the group consisting of residues of formula (I), (ii), (iii) and (iv)

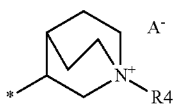

(i)

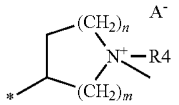

(ii)

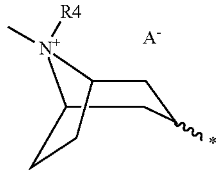

(iii)

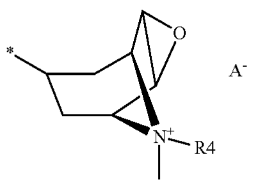

(iv)

wherein m=1, 2, or 3;

n=1, 2, or 3;

$A^-$ is a physiologically acceptable anion;

R4 is a group of formula (Y)

$$—(CH_2)_p—P—(CH_2)_q—W \quad (Y)$$

wherein p is 0 or an integer from 1 to 4;

q is 0 or an integer from 1 to 4;

P is absent or is selected from the group consisting of —O—, —S—, —SO—, —$SO_2$—, —C(O)—, —N(R5)-, —CH═CH—, —N(R5)($SO_2$)—, —N(R5)(COO)—, —N(R5)(C(O))—, —S($O_2$)N(R5)-, —CO(O)N(R5)-, and —C(O)N(R5)-;

W is selected from the group consisting of H, linear or branched ($C_1$-$C_{10}$)alkyl, ($C_2$-$C_6$)alkenyl, aryl, ($C_3$-$C_8$)cycloalkyl, ($C_5$-$C_{10}$)heterocycloalkyl, aryl($C_1$-$C_6$)alkyl, and heteroaryl, optionally substituted by one or more substituents selected from the group consisting of halogen atoms, —OH, oxo(═O), —SH, —$NO_2$, —N$(R5)_2$, —CN, —CON$(R5)_2$, —NH(COR5), —CO(R5), —$CO_2$(R5), ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, and heteroaryl;

R5 and R8 are independently selected from the group consisting of —H, ($C_1$-$C_{10}$)alkyl, ($C_1$-$C_{10}$)alkoxy, ($C_2$-$C_6$)alkynyl, ($C_2$-$C_6$)alkenyl, ($C_3$-$C_7$)cycloalkyl, ($C_3$-$C_7$)cycloalkyl-($C_1$-$C_{10}$)alkyl, heteroaryl, ($C_1$-$C_{10}$)alkyl-heteroaryl, and aryl optionally substituted by one or more substituents selected from the group consisting of halogen atoms, —OH, oxo (═O), —SH, —$NO_2$, —CN, —$CONH_2$, ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, and heteroaryl; and pharmaceutically acceptable salts thereof.

The present invention is also directed to compounds of general formula (VI):

(VI)

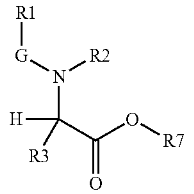

wherein:

R1, R2, R3, and G are as defined above;

R7 is selected from the group consisting of residues of formula (v), (vi), (vii), and (viii):

(v)

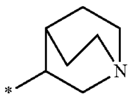

(vi)

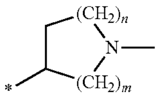

(vii)

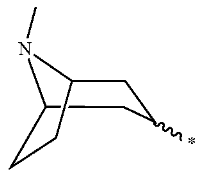

(viii)

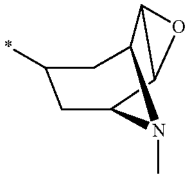

wherein:

m and n are as defined above.

The asterisk within groups of formula (i) to (viii), denotes the point of attachment with the rest of the molecule.

In the present disclosure, unless otherwise specified, the term "halogen" includes fluorine, chlorine, bromine, and iodine atoms.

The expression "$(C_1-C_{10})$alkyl", refers to straight or branched chain alkyl groups wherein the number of carbon atoms is from 1 to 10. Examples of said groups are methyl, ethyl, n-propyl, isopropyl, n-butyl, isobutyl, sec-butyl, tert-butyl, pentyl, hexyl, heptyl, octyl, nonyl, decyl, and the like.

The expression "$(C_2-C_6)$alkenyl" refers to straight or branched carbon chains with one or more double bonds. Examples of said groups are ethenyl, propenyl, butenyl, pentenyl, hexenyl, and the like.

The expression "$(C_1-C_{10})$alkoxy" refers to alkoxy groups formed from the above alkyl groups. Examples of said groups are methoxy, ethoxy, n-propoxy, isopropoxy, n-butoxy, isobutoxy, sec-butoxy, tert-butoxy, pentoxy, hexoxy, and the like.

Likewise, the expressions "$(C_1-C_{10})$alkylsulfanyl," "$(C_1-C_{10})$alkylsulfinyl," "$(C_1-C_{10})$alkylsulfonyl," and "$(C_1-C_{10})$ alkylcarboxyl refer, respectively, to alkyl-S—, alkyl-SO—, alkyl-$SO_2$—, or alkyl-COO groups.

The expression "$(C_3-C_8)$cycloalkyl" refers to cyclic non-aromatic hydrocarbon groups with 3 to 8 carbon atoms. Examples include cyclopropyl, cyclobutyl, cyclopentyl, cyclohexyl, cycloheptyl, cyclooctyl, and the like.

The expression "$(C_5-C_{10})$heterocycloalkyl" refers to $(C_5-C_{10})$cycloalkyl wherein one or more hydrogen atoms are replaced by one or more halogen atoms, which can be the same or different.

The expression "aryl" refers to mono-, or bi-, or tricyclic ring systems which have 6 to 20 ring atoms, preferably 6 to 15 and wherein at least one ring is aromatic.

The expressions "aryl$(C_1-C_6)$alkyl," "heteroaryl$(C_1-C_6)$ alkyl," and "$(C_3-C_8)$cycloalkyl$(C_1-C_6)$alkyl" refer to $(C_1-C_6)$ alkyl groups further substituted by aryl, heteroaryl or cycloalkyl rings.

The expression "aryloxy" refers to —O-aryl group. An example may be phenyloxy.

The expression "$(C_1-C_{10})$alkylene" refers to a chain with 1 to 10 —$CH_2$— groups. An example may be methylene.

The expression "$(C_1-C_{10})$alkyleneoxy" refers to —O$(C_1-C_{10})$alkylene.

The expression "aryl$(C_1-C_{10})$alkyleneoxy" refers to $(C_1-C_{10})$alkyleneoxy further substituted by aryl. An example may be benzyloxy.

The expression "heteroaryl" refers to mono-, bi-, or tricyclic ring systems which have 5 to 20 ring atoms, preferably 5 to 15, in which at least one ring is aromatic and in which at least one ring atom is a heteroatom or heteroaromatic group (e.g. N, NH, S, or O).

Examples of suitable aryl or heteroaryl monocyclic systems include for instance thiophene, benzene, pyrrole, pyrazole, imidazole, isoxazole, oxazole, oxadiazole, isothiazole, thiazole, pyridine, imidazolidine, and furan residues, and the like.

Examples of suitable aryl or heteroaryl bicyclic systems include benzodioxole, naphthalene, biphenylene, purine, pteridine, benzotriazole, quinoline, isoquinoline, indole, isoindole, benzothiophene, dihydrobenzo dioxin, dihydrobenzo dioxepin, and benzo oxazin residues, and the like.

Advantageously, the physiologically acceptable anions $A^-$ include those selected from chloride, bromide, iodide, trifluoroacetate, formate, sulfate, phosphate, methanesulfonate, nitrate, maleate, acetate, citrate, fumarate, tartrate, oxalate, succinate, benzoate, and p-toluenesulfonate.

Besides the presence of $A^-$ anion, whenever further basic amino groups are present in the compounds of formula (I), additional physiologically acceptable anions, among those formerly indicated, may be present. Likewise, in the presence of acidic groups such as COOH groups, corresponding physiologically acceptable cation salts may be present as well, for instance including alkali or earth-alkali metal ions.

A first preferred group of compounds of general formula (I) or (VI) is that wherein G is selected from the group consisting of —OC(O)—, —$SO_2$—, and —C(O)—, R1 is selected from the group consisting of linear or branched $(C_1-C_{10})$alkyl, aryl, $(C_3-C_8)$cycloalkyl, aryl$(C_1-C_6)$alkyl, $(C_2-C_6)$ alkenyl, $(C_5-C_{10})$heterocycloalkyl, and heteroaryl, optionally substituted by one or more substituents selected from halogen atoms, —N(R5)(R8), $(C_1-C_{10})$alkyl, $(C_1-C_{10})$alkylcarboxyl, $(C_1-C_{10})$alkoxy, aryloxy, and heteroaryl; R2 is H; and R3 and R6 are as defined above.

Still more preferred, within this class, are the compounds of general formula (I) or (VI) wherein R1 is selected from the group consisting of methyl, ethyl, methoxyethoxyl, tert-butyl, ethenyl, cyclohexyl, phenyl, methoxyphenyl, chlorophenyl, difluorophenyl, dimethylthiazole, trifluoroethyl, phenylethyl, cyclopentyl, methylethoxyl, oxo-phenylethyl, thiophenyl, thiazolyl, fluorophenyl, amino-phenyl, tert-butoxycarbonylamino-phenyl, and methylphenyl.

Another preferred group of compounds of general formula (I) or (VI) within this class, is that wherein G, R1, and R2 are as defined above; R3 is selected from the group consisting of $(C_1-C_{10})$alkyl, aryl and heteroaryl, optionally substituted by one or more groups selected from halogen atoms, $(C_1-C_{10})$ alkyl, $(C_1-C_{10})$alkoxy and aryl$(C_1-C_{10})$alkylenoxy; and R6 is as defined above.

An even more preferred group of compounds of general formula (I) or (VI) is that wherein G, R1, R2, and R3 are as defined above; R6 is selected from the group consisting of residues of formula (I), (ii) and (iii), wherein $A^-$ is as defined above, R4 is a group of formula (Y) wherein p is 0, 1, and 3, P is —C(O)—, q is 0, W is selected from the group consisting of $(C_1-C_{10})$alkyl, aryl, heteroaryl, $(C_5-C_{10})$heterocycloalkyl, optionally substituted by one or more substituents selected from the group consisting of halogen atoms, $(C_1-C_{10})$alkyl, $(C_1-C_{10})$alkoxy, —OH, and $(C_1-C_{10})$alkylcarboxyl.

Still more preferred, within this class, are the compounds of general formula (I) or (VI) wherein W is selected from the group consisting of phenyl, benzothioxol, thiophenyl, and thiazolyl, optionally substituted by one or more halogen atoms, —OH, methyl, and methylcarboxyl.

According to specific embodiments, the present invention provides the following compounds:

| Compound | Chemical name |
|---|---|
| C1 | (R)-quinuclidin-3-yl 2-(tert-butoxycarbonylamino)-2-phenylacetate |
| C2 | (3R)-3-(2-(tert-butoxycarbonylamino)-2-phenylacetoxy)-1-(2-oxo-2-phenylethyl)-1-azoniabicyclo[2.2.2]octane chloride |
| C3 | (3R)-3-(2-(tert-butoxycarbonylamino)-2-phenylacetoxy)-1-(2-oxo-2-(thiophen-2-yl)ethyl)-1-azoniabicyclo[2.2.2]octane chloride |
| C4 | (3R)-3-(2-(tert-butoxycarbonylamino)-2-phenylacetoxy)-1-(2-(4-fluorophenyl)-2-oxoethyl)-1-azoniabicyclo[2.2.2]octane bromide |
| C5 | (3R)-3-(2-(tert-butoxycarbonylamino)-2-phenylacetoxy)-1-(2-(3-fluorophenyl)-2-oxoethyl)-1-azoniabicyclo[2.2.2]octane bromide |
| C6 | (3R)-3-(2-(tert-butoxycarbonylamino)-2-phenylacetoxy)-1-(2-(2-fluorophenyl)-2-oxoethyl)-1-azoniabicyclo[2.2.2]octane bromide |
| C7 | (3R)-3-(2-(tert-butoxycarbonylamino)-2-phenylacetoxy)-1-(2-(2,4-difluorophenyl)-2-oxoethyl)-1-azoniabicyclo[2.2.2]octane bromide |
| C8 | (3R)-3-(2-(tert-butoxycarbonylamino)-2-phenylacetoxy)-1-(2-(4-chlorophenyl)-2-oxoethyl)-1-azoniabicyclo[2.2.2]octane bromide |
| C9 | (3R)-3-(2-(tert-butoxycarbonylamino)-2-phenylacetoxy)-1-(2-oxo-2-p-tolylethyl)-1-azoniabicyclo[2.2.2]octane bromide |

-continued

| Compound | Chemical name |
|---|---|
| C10 | (3R)-3-(2-(tert-butoxycarbonylamino)-2-phenylacetoxy)-1-(2-(4-methoxyphenyl)-2-oxoethyl)-1-azoniabicyclo[2.2.2]octane bromide |
| C11 | (3R)-3-(2-(tert-butoxycarbonylamino)-2-phenylacetoxy)-1-(2-(4-hydroxyphenyl)-2-oxoethyl)-1-azoniabicyclo[2.2.2]octane bromide |
| C12 | (3R)-3-(2-(tert-butoxycarbonylamino)-2-phenylacetoxy)-1-(2-(4-(methoxycarbonyl)phenyl)-2-oxoethyl)-1-azoniabicyclo[2.2.2]-octane bromide |
| C13 | (3R)-1-(2-(benzo[d][1,3]dioxol-5-yl)-2-oxoethyl)-3-(2-(tert-butoxycarbonylamino)-2-phenylacetoxy)-1-azoniabicyclo[2.2.2]-octane bromide |
| C14 | (3R)-1-(2-(benzo[b]thiophen-5-yl)-2-oxoethyl)-3-(2-(tert-butoxycarbonylamino)-2-phenylacetoxy)-1-azoniabicyclo[2.2.2]-octane bromide |
| C15 | (3R)-3-(2-(tert-butoxycarbonylamino)-2-phenylacetoxy)-1-(2-(5-chlorothiophen-2-yl)-2-oxoethyl)-1-azoniabicyclo[2.2.2]octane bromide |
| C16 | (3R)-3-(2-(tert-butoxycarbonylamino)-2-phenylacetoxy)-1-(2-oxo-2-(thiazol-2-yl)ethyl)-1-azoniabicyclo[2.2.2]octane bromide |
| C17 | (3R)-3-(2-(tert-butoxycarbonylamino)-2-phenylacetoxy)-1-(2-oxo-2-(thiophen-3-yl)ethyl)-1-azoniabicyclo[2.2.2]octane bromide |
| C18 | (3R)-3-(2-(tert-butoxycarbonylamino)-2-phenylacetoxy)-1-methyl-1-azoniabicyclo[2.2.2]octane iodide |
| C19 | (3R)-3-(2-(tert-butoxycarbonylamino)-2-phenylacetoxy)-1-(3-phenoxypropyl)-1-azoniabicyclo[2.2.2]octane bromide |
| C20 | (3R)-3-(2-(tert-butoxycarbonylamino)-2-phenylacetoxy)-1-(2-(2-methoxyphenyl)-2-oxoethyl)-1-azoniabicyclo[2.2.2]octane bromide |
| C21 | (3R)-3-(2-(tert-butoxycarbonylamino)-2-phenylacetoxy)-1-((5-phenyl-1,2,4-oxadiazol-3-yl)methyl)-1-azoniabicyclo[2.2.2]octane chloride |
| C22 | (3R)-1-(2-tert-butoxy-2-oxoethyl)-3-(2-(tert-butoxycarbonylamino)-2-phenylacetoxy)-1-azoniabicyclo[2.2.2]octane bromide |
| C23 | (3R)-3-(2-(tert-butoxycarbonylamino)-2-phenylacetoxy)-1-(2-(2-nitrophenyl)-2-oxoethyl)-1-azonia-bicyclo[2.2.2]octane bromide |
| C24 | (3R)-3-(2-(tert-butoxycarbonylamino)-2-phenylacetoxy)-1-(2-(2-hydroxyphenyl)-2-oxoethyl)-1-azoniabicyclo[2.2.2]octane bromide |
| C26 | (R)-quinuclidin-3-yl 2-(methoxycarbonylamino)-2-phenylacetate |
| C27 | (3R)-3-(2-(methoxycarbonylamino)-2-phenylacetoxy)-1-(2-oxo-2-phenylethyl)-1-azoniabicyclo[2.2.2]octane bromide |
| C29 | (R)-quinuclidin-3-yl 2-(benzyloxycarbonylamino)-2-phenylacetate |
| C31 | (3R)-3-(2-(benzyloxycarbonylamino)-2-phenylacetoxy)-1-(2-oxo-2-phenylethyl)-1-azoniabicyclo[2.2.2]octane bromide |
| C32 | (R)-quinuclidin-3-yl 2-phenyl-2-(vinyloxycarbonylamino)acetate |
| C33 | (3R)-1-(2-oxo-2-phenylethyl)-3-(2-phenyl-2-(vinyloxycarbonylamino)acetoxy)-1-azoniabicyclo[2.2.2]octane bromide |
| C34 | (R)-quinuclidin-3-yl 2-(ethoxycarbonylamino)-2-phenylacetate |
| C35 | (3R)-3-(2-(ethoxycarbonylamino)-2-phenylacetoxy)-1-(2-oxo-2-phenylethyl)-1-azoniabicyclo[2.2.2]octane bromide |
| C36 | (R)-quinuclidin-3-yl 2-((2-methoxyethoxy)carbonylamino)-2-phenylacetate |
| C37 | (3R)-3-(2-((2-methoxyethoxy)carbonylamino)-2-phenylacetoxy)-1-(2-oxo-2-phenylethyl)-1-azoniabicyclo[2.2.2]octane bromide |
| C38 | (R)-quinuclidin-3-yl 2-(cyclohexyloxycarbonylamino)-2-phenylacetate |
| C39 | (3R)-3-(2-(cyclohexyloxycarbonylamino)-2-phenylacetoxy)-1-(2-oxo-2-phenylethyl)-1-azoniabicyclo[2.2.2]octane bromide |
| C41 | (R)-quinuclidin-3-yl 2-(tert-butoxycarbonylamino)-2-p-tolylacetate |
| C42 | (3R)-3-(2-(tert-butoxycarbonylamino)-2-p-tolylacetoxy)-1-(2-oxo-2-phenylethyl)-1-azoniabicyclo[2.2.2]octane bromide |
| C44 | (R)-quinuclidin-3-yl 2-(tert-butoxycarbonylamino)-2-(4-methoxyphenyl)acetate |
| C45 | (3R)-3-(2-(tert-butoxycarbonylamino)-2-(4-methoxyphenyl)acetoxy)-1-(2-oxo-2-phenylethyl)-1-azoniabicyclo[2.2.2]octane bromide |
| C47 | (R)-quinuclidin-3-yl 2-(tert-butoxycarbonylamino)-2-(4-chlorophenyl)acetate |
| C48 | (3R)-3-(2-(tert-butoxycarbonylamino)-2-(4-chlorophenyl)acetoxy)-1-(2-oxo-2-phenylethyl)-1-azoniabicyclo[2.2.2]octane bromide |
| C50 | (R)-quinuclidin-3-yl 2-(tert-butoxycarbonylamino)-2-(4-fluorophenyl)acetate |
| C51 | (3R)-3-(2-(tert-butoxycarbonylamino)-2-(4-fluorophenyl)acetoxy)-1-(2-oxo-2-phenylethyl)-1-azoniabicyclo[2.2.2]octane bromide |
| C53 | (R)-quinuclidin-3-yl 2-(tert-butoxycarbonylamino)-2-(3-fluorophenyl)acetate |

-continued

| Compound | Chemical name |
|---|---|
| C54 | (3R)-3-(2-(tert-butoxycarbonylamino)-2-(3-fluorophenyl)acetoxy)-1-(2-oxo-2-phenylethyl)-1-azoniabicyclo[2.2.2]octane bromide |
| C56 | (R)-quinuclidin-3-yl 2-(tert-butoxycarbonylamino)-2-(2-fluorophenyl)acetate |
| C57 | (3R)-3-(2-(tert-butoxycarbonylamino)-2-(2-fluorophenyl)acetoxy)-1-(2-oxo-2-phenylethyl)-1-azoniabicyclo[2.2.2]octane bromide |
| C58 | (1R,3r,5S)-8-methyl-8-azabicyclo[3.2.1]octan-3-yl 2-(tert-butoxycarbonylamino)-2-phenylacetate |
| C59 | (1R,3r,5S)-3-(2-(tert-butoxycarbonylamino)-2-phenylacetoxy)-8-methyl-8-(2-oxo-2-phenylethyl)-8-azoniabicyclo[3.2.1]octane bromide |
| C60 | 3-(2-(tert-butoxycarbonylamino)-2-phenylacetoxy)-8,8-dimethyl-8-azoniabicyclo[3.2.1]octane iodide |
| C61 | (R)-1-methylpyrrolidin-3-yl 2-(tert-butoxycarbonylamino)-2-phenylacetate |
| C62 | (3R)-3-(2-(tert-butoxycarbonylamino)-2-phenylacetoxy)-1-methyl-1-(2-oxo-2-phenylethyl)pyrrolidinium bromide |
| C63 | (3R)-3-(2-(tert-butoxycarbonylamino)-2-phenylacetoxy)-1-methyl-1-(2-oxo-2-(thiophen-2-yl)ethyl)pyrrolidinium bromide |
| C64 | (R)-quinuclidin-3-yl 2-phenyl-2-(phenylsulfonamido)acetate |
| C65 | (3R)-1-(2-oxo-2-phenylethyl)-3-(2-phenyl-2-(phenylsulfonamido)-acetoxy)-1-azoniabicyclo[2.2.2]octane chloride |
| C66 | (3R)-1-(2-oxo-2-(thiazol-2-yl)ethyl)-3-(2-phenyl-2-(phenylsulfonamido)acetoxy)-1-azoniabicyclo[2.2.2]octane 2,2,2-trifluoroacetate |
| C67 | (3R)-1-(2-oxo-2-(thiophen-2-yl)ethyl)-3-(2-phenyl-2-(phenylsulfonamido)acetoxy)-1-azoniabicyclo[2.2.2]octane 2,2,2-trifluoroacetate |
| C68 | (R)-quinuclidin-3-yl 2-(4-methoxyphenylsulfonamido)-2-phenylacetate hydrochloride |
| C69 | (3R)-3-(2-(4-methoxyphenylsulfonamido)-2-phenylacetoxy)-1-(2-oxo-2-phenylethyl)-1-azoniabicyclo[2.2.2]octane bromide |
| C70 | (R)-quinuclidin-3-yl 2-(4-chlorophenylsulfonamido)-2-phenylacetate |
| C71 | (3R)-3-(2-(4-chlorophenylsulfonamido)-2-phenylacetoxy)-1-(2-oxo-2-phenylethyl)-1-azoniabicyclo[2.2.2]octane bromide |
| C72 | (R)-quinuclidin-3-yl 2-(3,4-difluorophenylsulfonamido)-2-phenylacetate |
| C73 | (3R)-3-(2-(3,4-difluorophenylsulfonamido)-2-phenylacetoxy)-1-(2-oxo-2-phenylethyl)-1-azoniabicyclo[2.2.2]octane 2,2,2-trifluoroacetate |
| C74 | (R)-quinuclidin-3-yl 2-(2,4-dimethylthiazole-5-sulfonamido)-2-phenylacetate |
| C75 | (3R)-3-(2-(2,4-dimethylthiazole-5-sulfonamido)-2-phenylacetoxy)-1-(2-oxo-2-phenylethyl)-1-azoniabicyclo[2.2.2]octane 2,2,2-trifluoroacetate |
| C76 | (R)-quinuclidin-3-yl 2-(methylsulfonamido)-2-phenylacetate |
| C77 | (3R)-3-(2-(methylsulfonamido)-2-phenylacetoxy)-1-(2-oxo-2-phenylethyl)-1-azoniabicyclo[2.2.2]octane bromide |
| C78 | (R)-quinuclidin-3-yl 2-phenyl-2-(2,2,2-trifluoroethylsulfonamido)-acetate |
| C79 | (3R)-1-(2-oxo-2-phenylethyl)-3-(2-phenyl-2-(2,2,2-trifluoroethylsulfonamido)acetoxy)-1-azoniabicyclo[2.2.2]octane bromide |
| C80 | (R)-quinuclidin-3-yl 2-phenyl-2-(phenylmethylsulfonamido)acetate |
| C81 | (3R)-1-(2-oxo-2-phenylethyl)-3-(2-phenyl-2-(phenylmethylsulfonamido)acetoxy)-1-azoniabicyclo[2.2.2]octane bromide |
| C83 | (R)-quinuclidin-3-yl 2-(4-fluorophenyl)-2-(phenylsulfonamido)-acetate |
| C84 | (3R)-3-(2-(4-fluorophenyl)-2-(phenylsulfonamido)acetoxy)-1-(2-oxo-2-phenylethyl)-1-azoniabicyclo[2.2.2]octane 2,2,2-trifluoroacetate |
| C85 | (R)-quinuclidin-3-yl 2-benzamido-2-phenylacetate |
| C86 | (3R)-3-(2-benzamido-2-phenylacetoxy)-1-(2-oxo-2-phenylethyl)-1-azoniabicyclo[2.2.2]octane chloride |
| C87 | (3R)-3-(2-benzamido-2-phenylacetoxy)-1-(2-(4-fluorophenyl)-2-oxoethyl)-1-azoniabicyclo[2.2.2]octane 2,2,2-trifluoroacetate |
| C88 | (3R)-3-(2-benzamido-2-phenylacetoxy)-1-(2-(4-hydroxyphenyl)-2-oxoethyl)-1-azoniabicyclo[2.2.2]octane 2,2,2-trifluoroacetate |
| C89 | (3R)-3-(2-benzamido-2-phenylacetoxy)-1-(2-oxo-2-(thiazol-2-yl)ethyl)-1-azoniabicyclo[2.2.2]octane 2,2,2-trifluoroacetate |
| C90 | (3R)-3-(2-benzamido-2-phenylacetoxy)-1-(2-oxo-2-(thiophen-3-yl)ethyl)-1-azoniabicyclo[2.2.2]octane 2,2,2-trifluoroacetate |
| C91 | (3R)-3-(2-benzamido-2-phenylacetoxy)-1-(2-oxo-2-(thiophen-2-yl)ethyl)-1-azoniabicyclo[2.2.2]octane 2,2,2-trifluoroacetate |
| C92 | (R)-quinuclidin-3-yl 2-acetamido-2-phenylacetate |

-continued

| Compound | Chemical name |
|---|---|
| C93 | (3R)-3-(2-acetamido-2-phenylacetoxy)-1-(2-oxo-2-phenylethyl)-1-azoniabicyclo[2.2.2]octane 2,2,2-trifluoroacetate |
| C94 | (R)-quinuclidin-3-yl 2-phenyl-2-pivalamidoacetate |
| C95 | (3R)-1-(2-oxo-2-phenylethyl)-3-(2-phenyl-2-pivalamidoacetoxy)-1-azoniabicyclo[2.2.2]octane 2,2,2-trifluoroacetate |
| C96 | (3R)-3-(2-(cyclopentanecarboxamido)-2-phenylacetoxy)-1-(2-oxo-2-phenylethyl)-1-azoniabicyclo[2.2.2]octane 2,2,2-trifluoroacetate |
| C97 | (3R)-1-(2-oxo-2-phenylethyl)-3-(2-phenyl-2-(2-phenylacetamido)-acetoxy)-1-azoniabicyclo[2.2.2]octane 2,2,2-trifluoroacetate |
| C98 | (3R)-3-(2-(3-ethoxy-3-oxopropanamido)-2-phenylacetoxy)-1-(2-oxo-2-phenylethyl)-1-azoniabicyclo[2.2.2]octane 2,2,2-trifluoroacetate |
| C99 | (3R)-1-(2-oxo-2-phenylethyl)-3-(2-(2-phenoxyacetamido)-2-phenylacetoxy)-1-azoniabicyclo[2.2.2]octane 2,2,2-trifluoroacetate |
| C100 | (3R)-1-(2-oxo-2-phenylethyl)-3-(2-phenyl-2-(thiophene-2-carboxamido)acetoxy)-1-azoniabicyclo[2.2.2]octane 2,2,2-trifluoroacetate |
| C101 | (3R)-1-(2-oxo-2-phenylethyl)-3-(2-phenyl-2-(thiazole-2-carboxamido)acetoxy)-1-azoniabicyclo[2.2.2]octane 2,2,2-trifluoroacetate |
| C102 | (3R)-3-(2-(4-fluorobenzamido)-2-phenylacetoxy)-1-(2-oxo-2-phenylethyl)-1-azoniabicyclo[2.2.2]octane 2,2,2-trifluoroacetate |
| C103 | (3R)-3-(2-(3-fluorobenzamido)-2-phenylacetoxy)-1-(2-oxo-2-phenylethyl)-1-azoniabicyclo[2.2.2]octane 2,2,2-trifluoroacetate |
| C104 | (3R)-3-(2-(4-methylbenzamido)-2-phenylacetoxy)-1-(2-oxo-2-phenylethyl)-1-azoniabicyclo[2.2.2]octane 2,2,2-trifluoroacetate |
| C105 | (3R)-3-(2-(4-methoxybenzamido)-2-phenylacetoxy)-1-(2-oxo-2-phenylethyl)-1-azoniabicyclo[2.2.2]octane 2,2,2-trifluoroacetate |
| C107 | (R)-quinuclidin-3-yl 2-benzamido-2-(4-methoxyphenyl)acetate |
| C108 | (3R)-3-(2-benzamido-2-(4-methoxyphenyl)acetoxy)-1-(2-oxo-2-phenylethyl)-1-azoniabicyclo[2.2.2]octane 2,2,2-trifluoroacetate |
| C110 | (R)-quinuclidin-3-yl 2-benzamido-2-p-tolylacetate |
| C111 | (3R)-3-(2-benzamido-2-p-tolylacetoxy)-1-(2-oxo-2-phenylethyl)-1-azoniabicyclo[2.2.2]octane 2,2,2-trifluoroacetate |
| C113 | (R)-quinuclidin-3-yl 2-benzamido-2-(4-chlorophenyl)acetate |
| C114 | (3R)-3-(2-benzamido-2-(4-chlorophenyl)acetoxy)-1-(2-oxo-2-phenylethyl)-1-azoniabicyclo[2.2.2]octane 2,2,2-trifluoroacetate |
| C116 | (3R)-3-(2-(tert-butoxycarbonylamino)-2-(thiophen-2-yl)acetoxy)-1-(2-oxo-2-phenylethyl)-1-azoniabicyclo[2.2.2]octane chloride |
| C118 | (3R)-3-(2-(tert-butoxycarbonylamino)-3-(1H-indol-3-yl)-propanoyloxy)-1-(2-oxo-2-phenylethyl)-1-azoniabicyclo[2.2.2]octane bromide |
| C120 | ((R)-3-((S)-3-(4-(benzyloxy)phenyl)-2-(tert-butoxycarbonylamino)-propanoyloxy)-1-(2-oxo-2-phenylethyl)-1-azoniabicyclo[2.2.2]octane bromide |
| C122 | (R)-3-((S)-2-(tert-butoxycarbonylamino)-3-(4-hydroxyphenyl)-propanoyloxy)-1-(2-oxo-2-phenylethyl)-1-azoniabicyclo[2.2.2]octane bromide |
| C124 | (R)-3-((S)-2-(tert-butoxycarbonylamino)-3-phenylpropanoyloxy)-1-(2-oxo-2-phenylethyl)-1-azoniabicyclo[2.2.2]octane bromide |
| C127 | (3R)-3-(2-(2-amino-2-phenylacetamido)-2-phenylacetoxy)-1-(2-oxo-2-phenylethyl)-1-azoniabicyclo[2.2.2]octane 2,2,2-trifluoroacetate 2,2,2-trifluoroacetic acid |
| C130 | (3R)-3-(2-benzamido-3-methylbutanoyloxy)-1-(2-oxo-2-phenylethyl)-1-azoniabicyclo[2.2.2]octane 2,2,2-trifluoroacetate |
| C131 | (3R)-3-(2-benzamido-3-methylbutanoyloxy)-1-(2-oxo-2-(thiophen-2-yl)ethyl)-1-azoniabicyclo[2.2.2]octane 2,2,2-trifluoroacetate |

The compounds of formula (I) and (VI) may possess at least one chiral center, when R3 is not H. Further, depending on the meanings of R1, R2, R6, and R7, it will be clear that additional asymmetric centers may be present in the compounds of formula (I) and (VI). Therefore, the invention also includes any of the optical stereoisomers, diastereoisomers and mixtures thereof, in any proportion.

In one of the preferred embodiment, the chiral center on rings (i), (iii), (iv), (v), (vii), and (viii), and (ii), (vi) when m and n are different, have the R configuration.

In the present invention, since the absolute configuration of the diastereomers is not always defined, they are indicated in the examples as diastereomer 1, 2, or mixtures of them.

The present invention also provides pharmaceutical compositions of compounds of formula (I) or (VI) alone or in combination or in admixture with one or more pharmaceutically acceptable carriers and/or excipients.

The present invention also provides pharmaceutical compositions suitable for administration by inhalation such as, for instance, inhalable powders, propellant-containing metering aerosols or propellant-free inhalable formulations.

The present invention also provides compounds of formula (I) or (VI) for use as a medicament.

The present invention also provides compounds of formula (I) or (VI) for use in the treatment of broncho-obstructive or inflammatory diseases, preferably asthma or chronic bronchitis or chronic obstructive pulmonary disease (COPD).

In a further aspect, the present invention provides the use of the compounds of formula (I) or (VI) for the manufacture of a medicament for the prevention and/or treatment of broncho-obstructive or inflammatory diseases, preferably asthma or chronic bronchitis or chronic obstructive pulmonary disease (COPD).

The present invention also provides a method for the prevention and/or treatment of broncho-obstructive or inflammatory diseases, preferably asthma or chronic bronchitis or chronic obstructive pulmonary disease (COPD), which comprises administering to a subject in need thereof a therapeutically effective amount of a compound of general formula (I) or (VI).

The present invention also provides pharmaceutical compositions suitable for administration by inhalation, such as inhalable powders, propellant-containing metering aerosols or propellant-free inhalable formulations.

The present invention also provides devices which may be a single- or multi-dose dry powder inhaler, a metered dose inhaler and a soft mist nebulizer comprising the compounds of formula (I) or (VI).

The present invention also refers to kits comprising the above pharmaceutical compositions in a suitable vial or container and a device which may be a single- or multi-dose dry powder inhaler, a metered dose inhaler and a soft mist nebulizer, adapted to hold the above vial or container.

The present invention is also directed to a process for the preparation of a compound of formula (I) or (VI) which comprises:

(a) the reaction of compounds of general formula (III):

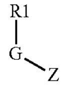

(III)

(b) with compounds of general formula (II):

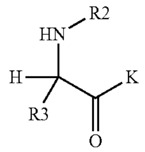

(II)

to provide the corresponding compounds of general formula (IV):

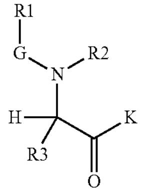

(IV)

(c) the coupling between compounds of general formula (IV) and (V)

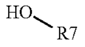

(V)

to obtain a compound of general formula (VI):

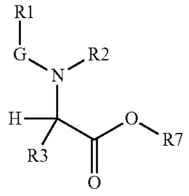

(VI)

and and (d) the alkylation of compounds of general formula (VI) by alkylating agents of general formula (Y):

$$-(CH_2)_p-P-(CH_2)_q-W \qquad (Y)$$

linked to a group A, which is a suitable leaving group, to obtain a compound of general formula (I), wherein p, P, q, W, R1, R2, R3, R6, and R7 have the above reported meanings.

The present invention is also directed to a process for the preparation of a compound of formula (VI) which comprises:

(a) the treatment of the acid of formula (IV) with one or more equivalents of a condensing agent to obtain an activated intermediate; and (b) the reaction of the activated intermediate with alcohol of general formula (V).

The present invention is also directed to a process for the preparation of a compound of formula (VI) which comprises:

(a) the conversion of a compound of formula (IV) wherein K=OH into the corresponding acyl halide of formula (IV) wherein K=halide; and (b) the reaction of the acyl halide of formula (IV) with a compound of formula (V).

The compounds of formula (I) or (VI) may be prepared according to known methods.

The starting materials for the preparation of the compounds of formula (I) or (VI), as well as any reactant of the processes, are known or easily prepared according to known procedures.

The operative conditions that may be used in the process of the present invention are described in more details below and are further reported in the following Scheme 1.

Scheme 1

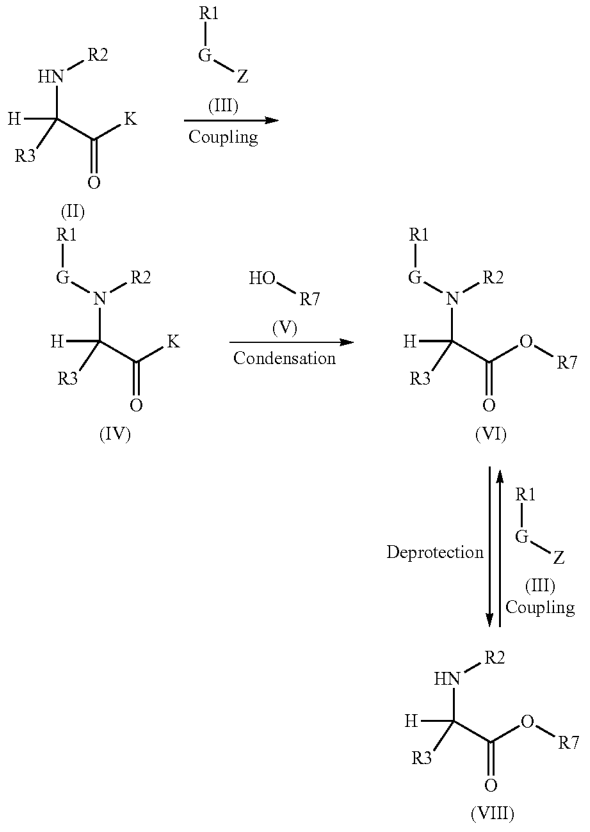

(II) (IV) (VI) (VIII)

Procedure for the Preparation of Compounds of Formula (VI) and (I).

Compounds reported in the present invention can be most conveniently prepared starting from compounds of general formula (II), in which K may be either a hydroxyl group or a suitable protecting hydroxyl group (e.g. K=($C_1$-$C_{10}$)alkoxy such as OMe). The compounds of general formula (II) can be reacted with compounds of general formula (III), in which z is a suitable leaving group such as an halide (i.e. chlorine, bromine, fluorine) or a oxygen substituted with another R1-G group (e.g. when R1 is a tert-butyl group, G is a COO group and z is a —O-G-R1 group, compound (III) is di-tert-butyl dicarbonate or Boc anhydride; when R1 is methyl, G is CO and z is a —O-G-R1 group, compound (III) is acetic anhydride; when R1 is $CF_3$, G is $SO_2$ and z is a —O-G-R1 group, compound (III) is trifluoromethanesulphonic anhydride). This reaction can be effected according to standard procedures reported in the literature. In a typical procedure, compounds of formula (III) are added to a solution of compounds of formula (II) in a suitable solvent (e.g. dichloromethane, ethyl acetate, tetrahydrofuran and water) to provide the corresponding compounds of general formula (IV). The reaction is conveniently promoted by a base such as triethylamine, pyridine, 4-dimethylaminopyridine and sodium hydroxide. This reaction is usually performed in a temperature range from 0° C. to 130° C. over a period of 30 minutes up to 74 hours. The reaction may be carried out under conventional heating (using an oil bath) or microwave heating. The reaction may be carried out in an open vessel or in a sealed tube.

Reagents of general formula (III) are commercially available or may be prepared according to standard procedures reported in literature. When z in compounds (III) is a hydroxyl group (z=OH), it may be either converted into a suitable leaving group (such as a halide or a oxygen substituted with another R1-G group to form an anhydride) or condensed to compounds of formula (II) under standard amidation and peptide coupling conditions.

The coupling between compounds of general formula (IV) and (V) may be conducted in several ways (a survey of the suitable reactions is given by Carey, F. A. and Sundeberg, R. J. Advanced Organic Chemistry, Third Edition (1990), Plenum Press, New York and London, pg 145, which is incorporated herein by reference).

In particular, when K is a protected hydroxyl group, the protecting group has to be removed before the coupling with (V). For instance, if K═OMe, hydrolysis of the ester moiety may be performed treating the compound (IV) wherein K═OMe with a suitable aqueous base selected from sodium, lithium, and potassium hydroxide in the suitable solvents (e.g. tetrahydrofuran, dioxane etc). The reaction proceeds at room temperature (RT), over a period of 1 hour up to 36 hours.

Alternative one—In a typical procedure, compounds (VI) may be prepared by condensation between compounds of formula (V) and (IV) wherein K═OH, under standard amidation and peptide coupling conditions. For instance, treatment of compound (IV) with one or more equivalents of a commercially available condensing agent such as a carbodiimide (e.g. N,N'-Dicyclohexylcarbodiimide (DCC) and the like) for example in the presence of N-hydroxybenzotriazole (HOBt) followed by reaction of the activated intermediate with alcohol (V), results in the formation of compounds of formula (VI). An organic base such as triethylamine or 4-dimethylaminopyridine may be also present in the reaction mixture. The activated intermediate may be either isolated, or pre-formed or generated in situ. Suitable solvents for the coupling include, but are not limited to, halocarbon solvents (e.g. dichloromethane), tetrahydrofuran, dioxane, and acetonitrile. The reaction proceeds at temperature range from 0° C. up to 170° C., for a time in the range of about 1 hour up to 72 hours. The reaction may be carried out under conventional heating (using an oil bath) or under microwave irradiation. The reaction may be conducted either in an open vessel or in a sealed tube.

Alternative two—In some embodiments of the present invention, a compound of formula (IV) wherein K═OH, is first converted into the corresponding acyl halide (IV) wherein K=halide. This activation may be effected according to one of the standard procedures reported in the literature. For instance, treatment of acid (IV) wherein K═OH, with one or more equivalents of oxalyl chloride in the presence of a catalytic amount of dimethylformamide (DMF) in a halocarbon solvent, such as dichloromethane, at temperature ranging form 0° C. to 35° C., affords the required acyl chloride (IV) wherein K═Cl.

Alcohol (V) is then reacted with the acyl halide (IV), using known methods. The reaction may be promoted by a base such as triethylamine, pyridine and 4-dimethylaminopyridine, in a suitable solvent (e.g. dichloromethane). This reaction is performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

Alternative three—Alternatively, acylation of alcohol (V) to give compounds of general formula (VI) may be accomplished using procedures which convert in situ the acid (IV) wherein K═OH, into the corresponding acyl halides. For example, alcohols (V) are reacted with acids (IV) wherein K═OH, in presence of triphenylphosphine and a halocarbon solvent such as carbon tetrachloride or dichloromethane, at about RT, in a maximum period of time of 16 hours (see Lee, J. B. *J. Am. Chem. Soc.,* 1966, 88, 3440, which is incorporated herein by reference).

Alternative four—In another process for the preparation of the compounds of the present invention, acid (IV) wherein K═OH, may be activated with other commercially available activating agents such as bromotripyrrolidinophosphonium hexafluorophosphate (PyBrOP) or carbonylimidazole, in the suitable solvent (e.g. dichloromethane, tetrahydrofuran and DMF), at about RT. Subsequent reaction of the activated intermediate with alcohol (V) provides the desired compound of formula (VI). The reaction may also require the use of an organic base such as diisopropylethylamine and the like and usually proceeds at about RT.

Alternative five—In another process for the preparation of the compounds of the present invention, compounds (VI) can be efficiently prepared by the condensation between acids (IV) wherein K═OH and alcohol (V) under typical Mitsunobu conditions (see Kumara Swamy, K. C., *Chem. Rev.,* 2009, 109, 2551-2651, which is incorporated herein by reference). For example, acids (IV) and alcohol (V) are reacted in presence of a phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from 0° C. up to 100° C., for a time in the range of about 30 minutes up to 72 hours.

In some embodiments of the present invention, group R1-G- in compounds of general formula (VI) can be most conveniently used as a protecting group and can be removed to obtain compounds of general formula (VIII). These protecting groups are selected, manipulated and removed according to standard methods of organic synthesis (see Green T. W. and Wuts P. G. M. (1991) Protecting Groups in Organic Synthesis, John Wiley et Sons, which is incorporated herein by reference in its entirety). For instance, if R1 in compounds (VI) is tert-butyl and G is O(CO), the tert-butyloxycarbonyl (boc) protecting group can be cleaved by treating compounds of general formula (VI) with a protic acid such as hydrochloric acid, trifluoroacetic acid and the like. Suitable solvents for deprotection include, but are not limited to, 1,4-dioxane, tetrahydrofuran, dichloromethane, and methanol. Water may be also present in the reaction mixture. The reaction proceeds at temperature range from 0° C. up to 80° C., for a time in the range of few minutes up to 72 hours.

Compounds of general formula (VIII) may be then coupled to compounds of general formula (III) to yield compounds (VI), applying known procedures. For instance, the conditions used to perform the coupling may be selected among those described to produce the coupling between compound (II) and (III) in Scheme 1.

Compounds of general formula (VI) can be obtained either as a single diastereoisomer or as a mixture of diastereoisomers. For instance, in the case R7 is a group of formula (V), the alcohol features either a R or a S configuration. If the R-enantiomer is used, the compound of formula (VI) can be obtained in the S—R configuration, in the R—R configuration or as a mixture of diastereoisomers (R—R and S—R configuration).

The mixture of diastereoisomers may be converted to compounds of formula (I) of Scheme 1 or resolved to give the two single diastereoisomers, which in turn may be converted to compounds of formula (I) of Scheme 1. This separation can be accomplished using known procedures. These procedures include, but are not limited to, chromatography purification, preparative HPLC purification and crystallization. For example, the two diastereoisomers can be separated by flash chromatography on silica gel eluting with suitable solvents or mixture of solvents such as DCM and methanol and the like. In another process of the present invention separation of diastereoisomers may be obtained using a column filled with a chiral stationary phase, for example Chiralpack® AY or Chiralcel OD®, or Chiralcel OZ®, and eluting, for example, with acetonitrile and/or with mixtures of acetonitrile and an alcohol. Alternatively, the separation of diastereoisomers may be most conveniently achieved by crystallization from a suitable solvent (e.g. ethyl ether and acetone), as a free base or after the formation of a suitable salt (e.g. D-tartaric acid)).

The alkylation of compounds of general formula (VI) by alkylating agents of general formula (Y), linked to a suitable leaving group A selected from the group consisting of halide (i.e. bromine, iodine, chlorine) and sulfonate ester (i.e. tosylate, triflate, mesylate), gives the compounds of general formula (I). This kind of reaction is widely described in literature under several different conditions, for instance, the reaction may be performed neat or in a suitable solvent selected from acetonitrile, ethyl acetate, DMF, DMSO, and tetrahydrofuran. The reaction typically proceeds at temperatures from 0° C. up to 170° C., for a time in the range of few minutes up to 72 hours. The reaction may be carried out under conventional heating (using an oil bath) or under microwave irradiation. The reaction may be conducted either in an open vessel or in a sealed tube.

Compounds of general formula (I) in Scheme 1 can be either considered as final products or can be further reacted to prepare other compounds of general formula (I). Thus, a moiety of R1, R2, R3, or R6 group in general formula (I) can undergo oxidation, reduction or cleavage reactions (e.g. to remove a needed protecting group) to afford other final compounds of general formula (I).

The present invention also provides pharmaceutical compositions of compounds of formula (I) or (VI) in admixture with one or more pharmaceutically acceptable carriers, for example those described in *Remington's Pharmaceutical Sciences Handbook*, XVII Ed., Mack Pub., N.Y., U.S.A., which is incorporated herein by reference in its entirety.

Administration of the compounds of the invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges, and bulk powders. The compounds of the present invention can be administered alone or combined with various known pharmaceutically acceptable carriers, diluents (such as sucrose, mannitol, lactose, starches) and excipients, including but not limited to suspending agents, solubilizers, buffering agents, binders, disintegrants, preservatives, colorants, flavors, lubricants, and the like. Time release capsules, tablets, and gels are also advantageous.

Various liquid oral dosage forms can also be used for administering the compounds of the invention, including aqueous and non-aqueous solutions, emulsions, suspensions, syrups, and elixirs. Such dosage forms can also contain suitable known inert diluents such as water, excipients such as preservatives, wetting agents, sweeteners, flavors, as well as agents for emulsifying and/or suspending the compounds of the invention. The compounds of the invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates, and polyethylene glycols.

Formulations for vaginal administration can be in the form of cream, gel, paste, foam, or spray formulations containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the present invention are preferably administered by inhalation.

Inhalable compositions include inhalable powders, propellant-containing metering aerosols, or propellant-free inhalable formulations.

For administration as a dry powder, known single- or multi-dose inhalers may be utilized. In that case, the powder may be filled in gelatine, plastic or other capsules, cartridges or blister packs or in a reservoir.

A diluent or carrier, generally non-toxic and chemically inert to the compounds of the present invention, e.g. lactose or any other additive suitable for improving the respirable fraction, may be added to the powdered compounds of the invention.

Inhalation aerosols containing a propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic, or hydroalcoholic medium and they may be delivered by jet or ultrasonic nebulizers or by soft-mist nebulizers.

The compounds of the present invention may be administered as the sole active agent or in combination with other pharmaceutical active ingredients including those currently used in the treatment of respiratory disorders, e.g. beta2-agonists, corticosteroids, P38 MAP kinase inhibitors, IKK2 inhibitors, HNE inhibitors, PDE4 inhibitor, leukotriene modulators, NSAIDs, and mucus regulators.

The present invention also provides combinations of a compound of formula (I) or (VI) with a β2-agonist selected from the group consisting of GSK-642444, indacaterol, milveterol, arformoterol, salbutamol, levalbuterol, terbutaline, AZD-3199, BI-1744-CL, LAS-100977, bambuterol, isoproterenol, procaterol, clenbuterol, reproterol, fenoterol, and ASF-1020.

The present invention also provides combinations of a compound of formula (I) or (VI) with a corticosteroid selected from the group consisting of propionate, ciclesonide, mometasone furoate, and budesonide.

The present invention also provides combinations of a compound of formula (I) or (VI) with a P38 inhibitor selected from the group consisting of semapimod, talmapimod, pirfenidone, PH-797804, GSK-725, minokine, and losmapimod.

The present invention also provides combinations of a compound of formula (I) or (VI) with an IKK2 inhibitor.

The present invention also provides combinations of a compound of formula (I) or (VI) with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound of formula (I) or (VI) with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TP1-PD3, ELB-353, CC-11050, GSK-256066, oglemilast, OX-914, tetomilast, MEM-1414, and RPL-554.

The present invention also provides combinations of a compound of consisting of montelukast, zafirlukast, and pranlukast.

The present invention also provides combinations of a compound of formula (I) or (VI) with a NSAID selected from the group consisting of ibuprofen and ketoprofen.

The present invention also provides combinations of a compound of formula (I) (VI) with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) or (VI) can be administered for example, at a dosage comprised between 0.001 and 1000 mg/day, preferably between 0.1 and 500 mg/day.

When the compounds of formula (I) or (VI) are administered by inhalation route, they are preferably given at a dosage comprised between 0.001 and 500 mg/day, preferably between 0.1 and 200 mg/day.

The compounds of formula (I) or (VI) may be administered for the prevention and/or treatment of any disease wherein M3 antagonists are active. Said diseases include: diseases involving inflammation such as asthma and COPD, acute rhinitis; diseases of the gastrointestinal tract such as peptic ulcer; diseases of the cardiovascular system such as acute myocardial infarction; diseases of the genitourinary tract such as renal colic; anticholinesterase and mushroom poisoning; uses in anesthesia; uses in ophthalmology. They also include neurological and psychiatric disorders such as Parkinsonism and motion sickness.

Preferably, the compounds of formula (I) or (VI) may be administered for the prevention and/or treatment of respiratory diseases such as from mild to acute severe conditions of asthma and COPD.

Other respiratory diseases include bronchitis, bronchiolitis, bronchiectasis, acute nasopharyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, nasal abscess or ulcer, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, and mediastinitis.

Other features of the invention will become apparent in the course of the following descriptions of exemplary embodiments which are given for illustration of the invention and are not intended to be limiting thereof.

EXAMPLES

In the examples below, the following abbreviations are used:

I=intermediates

C=compounds

RT=room temperature.

Example 1

Preparation of (R)-3-((R)-2-(tert-butoxycarbonylamino)-2-phenylacetoxy)-1-(2-oxo-2-phenylethyl)-1-azoniabicyclo[2.2.2]octane bromide (Diastereoisomers 1 of C2)

Scheme 2

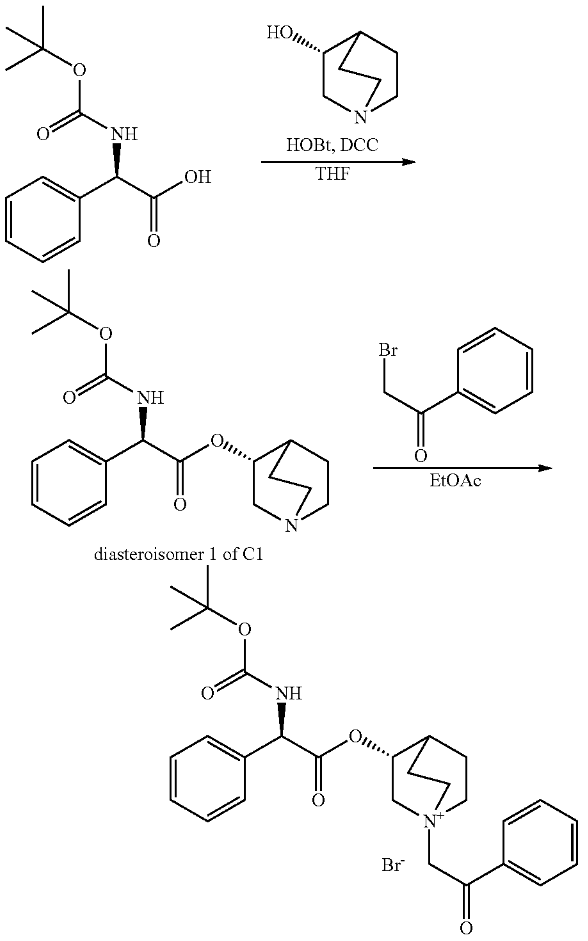

diasteroisomer 1 of C1 diasteroisomer 1 of C2

Preparation of (R)—((R)-quinuclidin-3-yl)2-(tert-butoxycarbonylamino)-2-phenylacetate (Diasteroisomer 1 of C1)

A mixture of (R)-2-(tert-butoxycarbonylamino)-2-phenylacetic acid (1.00 g, 3.98 mmol), (R)-quinuclidin-3-ol (0.51 g, 3.98 mmol), 1H-benzo[d][1,2,3]triazol-1-ol (0.64 g, 4.78 mmol), and DCC (0.98 g, 4.78 mmol) was stirred at RT overnight. Then THF was removed by vacuum, and the residue was partitioned between EtOAc and 2M $K_2CO_3$. The organic phase was dried over $Na_2SO_4$, filtered, and evaporated to dryness. The crude was purified by flash chromatography (DCM/MeOH=98/2 to 95/5) to obtain (R)—((R)-quinuclidin-3-yl) 2-(tert-butoxycarbonylamino)-2-phenylacetate (612 mg; 43% yield).

$^1$H NMR (300 MHz, DMSO-$d_6$) δ ppm 7.74 (d, 1H), 7.17-7.52 (m, 5H), 5.19 (d, 1H), 4.58-4.82 (m, 1H), 2.99 (ddd, 1H), 2.55-2.69 (m, 3H), 2.32-2.46 (m, 1H), 2.18 (d, 1H), 1.79-1.98 (m, 1H), 1.44-1.71 (m, 3H), 1.40 (s, 9H), 1.11-1.33 (m, 1H);

LC-MS (ESI POS): 361.4 (MH+).

Preparation of (R)-3-((R)-2-(tert-butoxycarbonylamino)-2-phenylacetoxy)-1-(2-oxo-2-phenylethyl)-1-azoniabicyclo[2.2.2]octane bromide (Diastereoisomers 1 of C2)

2-Bromo-1-phenylethanone (27.6 mg, 0.14 mmol) was added to a solution of (R)—((R)-quinuclidin-3-yl) 2-(tert-butoxycarbonylamino)-2-phenylacetate (Diasteroisomer 1 of C1) (50 mg, 0.14 mmol) in EtOAc (3 ml). The reaction was stirred at RT overnight. The precipitate was collected by suction filtration and washed with $Et_2O$ to obtain (R)-3-((R)-2-(tert-butoxycarbonylamino)-2-phenylacetoxy)-1-(2-oxo-2-phenylethyl)-1-azoniabicyclo[2.2.2]octane bromide (65 mg; 84% yield).

$^1$H NMR (300 MHz, DMSO-$d_6$) δ ppm 7.92-8.03 (m, 2H), 7.89 (d, 1H), 7.70-7.80 (m, 1H), 7.56-7.68 (m, 2H), 7.30-7.52 (m, 5H), 5.30 (d, 1H), 5.17-5.24 (m, 1H), 5.15 (s, 2H), 4.02-4.19 (m, 1H), 3.42-3.83 (m, 5H), 2.30-2.42 (m, 1H), 1.75-2.12 (m, 4H), 1.42 (s, 9H);

LC-MS (ESI POS): 479.09 (M+).

Example 2

Preparation of (3R)-3-(2-(tert-butoxycarbonylamino)-2-phenylacetoxy)-1-(2-oxo-2-phenylethyl)-1-azoniabicyclo[2.2.2]octane chloride (C2)

Scheme 3

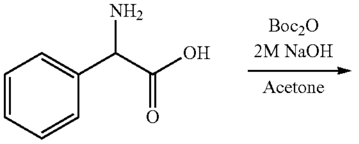

-continued

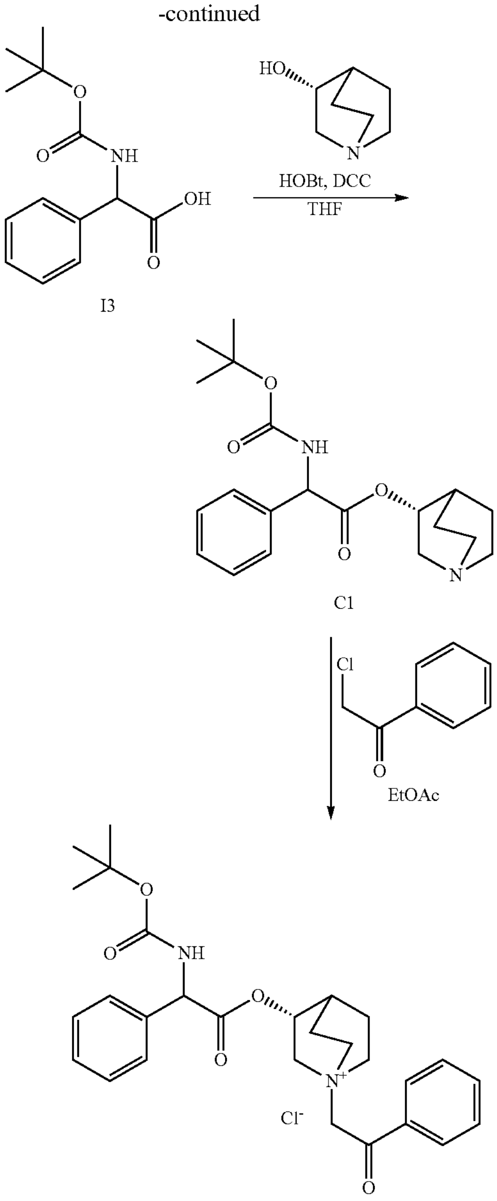

I3

C1

C2

Preparation of 2-(tert-butoxycarbonylamino)-2-phenylacetic acid (I3)

A mixture of 2-amino-2-phenylacetic acid (2.00 g, 13.2 mmol) and di-tert-butyl dicarbonate (3.47 g, 15.9 mmol) in sodium hydroxide (50 ml, 100 mmol) and acetone (50 ml) was stirred at RT for 1 hour. Acetone was removed under reduced pressure, the aqueous phase was acidified to pH about 5 with HCl and extracted twice with EtOAc. The organic phase was dried over $Na_2SO_4$, filtered, and evaporated to dryness to provide 2-(tert-butoxycarbonylamino)-2-phenylacetic acid (1.42 g; 43% yield). The compound was used in the next step without any further purification.

Preparation of (R)-quinuclidin-3-yl 2-(tert-butoxycarbonylamino)-2-phenylacetate (C1)

A mixture of 2-(tert-butoxycarbonylamino)-2-phenylacetic acid (I3) (2.00 g, 7.96 mmol), (R)-quinuclidin-3-ol (1.21 g, 9.55 mmol), HOBt (1.46 g, 9.55 mmol), and DCC (1.97 g, 9.55 mmol) in dry THF (70 ml) was stirred at RT overnight. Then THF was evaporated and the crude was taken up with DCM and washed twice with 2M $K_2CO_3$ and brine. The organic phase was dried over $Na_2SO_4$, filtered, and evaporated to dryness. The crude was purified by flash chromatography (DCM/MeOH=95/5) to get (R)-quinuclidin-3-yl 2-(tert-butoxycarbonylamino)-2-phenylacetate (1.68 g; 58.5% yield).

$^1$H NMR (300 MHz, DMSO-$d_6$) δ ppm

Diastereoisomer 1: 7.73 (d, 1H), 7.12-7.54 (m, 5H), 5.19 (d, 1H), 4.52-4.84 (m, 1H), 2.99 (ddd, 1H), 2.54-2.70 (m, 3H), 2.31-2.47 (m, 1H), 2.12-2.24 (m, 1H), 1.84-1.92 (m, 1H), 1.47-1.71 (m, 2H), 1.40 (s, 9H), 1.06-1.36 (m, 2H);

Diastereoisomer 2: 7.73 (d, 1H), 7.12-7.54 (m, 5H), 5.19 (d, 1H), 4.52-4.84 (m, 1H), 2.99 (ddd, 1H), 2.54-2.70 (m, 5H), 1.69-1.79 (m, 1H), 1.47-1.71 (m, 2H), 1.40 (s, 9H), 1.06-1.36 (m, 2H);

LC-MS (ESI POS): 361.16 (MH+).

Preparation of (3R)-3-(2-(tert-butoxycarbonylamino)-2-phenylacetoxy)-1-(2-oxo-2-phenylethyl)-1-azoniabicyclo[2.2.2]octane chloride (C2)

2-Chloro-1-phenylethanone (30.0 mg, 0.19 mmol) was added to a solution of (R)-quinuclidin-3-yl 2-(tert-butoxycarbonylamino)-2-phenylacetate (C1) (70.0 mg, 0.19 mmol) in EtOAc (2 ml). The reaction was stirred at RT for 24 hours. Then $Et_2O$ (1 ml) was added, and the reaction was sonicated. The solid was collected by suction filtration to obtain (3R)-3-(2-(tert-butoxycarbonylamino)-2-phenylacetoxy)-1-(2-oxo-2-phenylethyl)-1-azoniabicyclo[2.2.2]octane chloride (54.6 mg; 55% yield).

$^1$H NMR (300 MHz, DMSO-$d_6$) δ ppm 7.94-8.05 (m, 2H), 7.89 (d, 1H), 7.70-7.82 (m, 1H), 7.54-7.70 (m, 2H), 7.28-7.53 (m, 5H), 5.27-5.37 (m, 1H), 5.08-5.27 (m, 2H), 3.95-4.28 (m, 1H), 3.44-3.88 (m, 5H), 2.19 and 2.37 (br. s., 1H), 1.52-2.12 (m, 4H), 1.41 (s, 9H);

LC-MS (ESI POS): 479.21 (M+).

The compounds listed in Table 1 were obtained as previously described for C2, starting from compound C1 and the suitable commercially available alkylating agents.

TABLE 1

| Compound | Structure | Yield | Analytical |
|---|---|---|---|
| C3 | 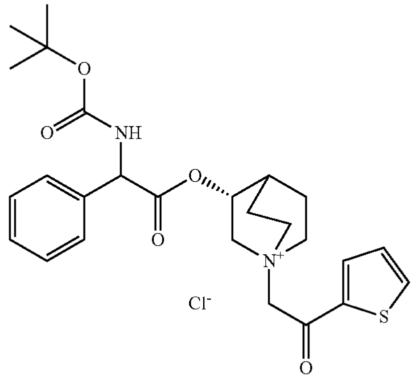 [SMILES: CC(C)(C)OC(=O)NC(C(=O)O[C@H]1C[N+]2(CC(=O)c3cccs3)CCC1CC2)c1ccccc1 ; [Cl-]] Mixture of diastereoisomers | 70% | LC-MS (ESI POS): 485.15 ($M^+$) $^1$H NMR (300 MHz, DMSO-$d_6$) δ ppm 8.17-8.24 (m, 1 H), 8.05-8.15 (m, 1 H), 7.88 (d, 1 H), 7.23-7.56 (m, 6 H), 5.24-5.37 (m, 1 H), 5.13-5.23 (m, 1 H), 4.99-5.10 (m, 1 H), 3.96-4.21 (m, 1 H), 3.43-3.81 (m, 5 H), 2.12-2.23 and 2.31-2.39 (m, 1 H), 1.46-2.12 (m, 4 H), 1.41 (s, 9 H) |
| C4 | 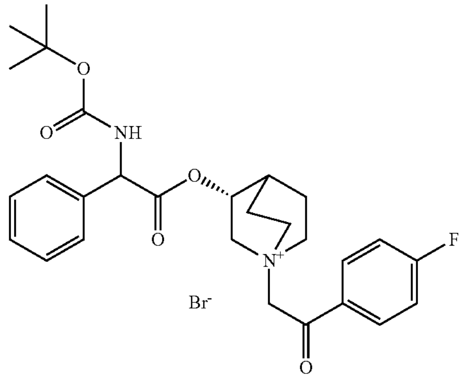 [SMILES: CC(C)(C)OC(=O)NC(C(=O)O[C@H]1C[N+]2(CC(=O)c3ccc(F)cc3)CCC1CC2)c1ccccc1 ; [Br-]] Mixture of diastereoisomers | 63% | LC-MS (ESI POS): 497.22 ($M^+$) $^1$H NMR (300 MHz, DMSO-$d_6$) δ ppm 8.00-8.13 (m, 2 H), 7.88 (d, 1 H), 7.25-7.52 (m, 7 H), 5.26-5.36 (m, 1 H), 5.16-5.26 (m, 1 H), 5.02-5.16 (m, 1 H), 3.91-4.28 (m, 1 H), 3.43-3.86 (m, 5 H), 2.15-2.23 and 2.31-2.41 (m, 1 H), 1.55-2.12 (m, 4 H), 1.41 (s, 9 H) |

TABLE 1-continued

| Compound | Structure | Yield | Analytical |
|---|---|---|---|
| C5 | 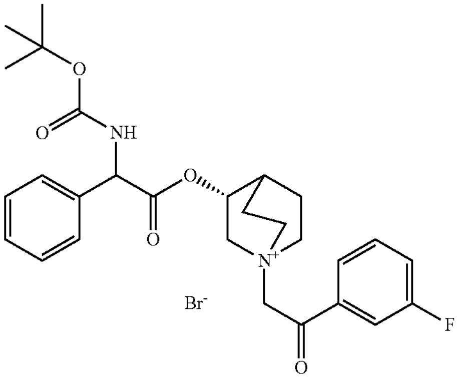 [SMILES: CC(C)(C)OC(=O)NC(C(=O)O[C@H]1C[N+]2(CC(=O)c3cccc(F)c3)CCC1CC2)c1ccccc1 ; [Br-]]<br>Mixture of diastereoisomers | 89% | LC-MS (ESI POS): 497.20 ($M^+$)<br>$^{1}$H NMR (300 MHz, DMSO-$d_6$) δ ppm 7.88 (d, 1 H), 7.72-7.85 (m, 2 H), 7.55-7.74 (m, 2 H), 7.26-7.52 (m, 5 H), 5.03-5.46 (m, 3 H), 3.98-4.22 (m, 1 H), 3.38-3.83 (m, 5 H), 2.15-2.25 and 2.31-2.44 (m, 1 H), 1.57-2.13 (m, 4 H), 1.41 (s, 9 H) |
| C6 | 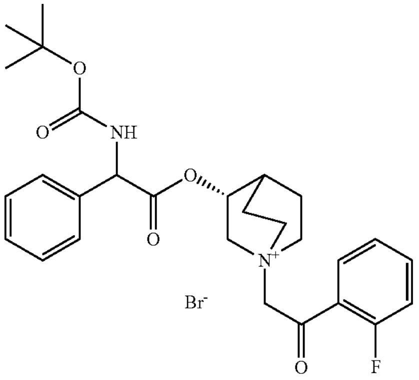 [SMILES: CC(C)(C)OC(=O)NC(C(=O)O[C@H]1C[N+]2(CC(=O)c3ccccc3F)CCC1CC2)c1ccccc1 ; [Br-]]<br>Mixture of diastereoisomers | 85% | LC-MS (ESI POS): 497.21 ($M^+$)<br>$^{1}$H NMR (300 MHz, DMSO-$d_6$) δ ppm 7.91-8.03 (m, 1 H), 7.88 (d, 1 H), 7.70-7.85 (m, 1 H), 7.29-7.54 (m, 7 H), 5.11-5.45 (m, 2 H), 4.90-5.11 (m, 1 H), 3.96-4.28 (m, 1 H), 3.45-3.86 (m, 5 H), 2.15-2.23 and 2.31-2.42 (m, 1 H), 1.51-2.13 (m, 4 H), 1.41 (s, 9 H) |
| C7 | 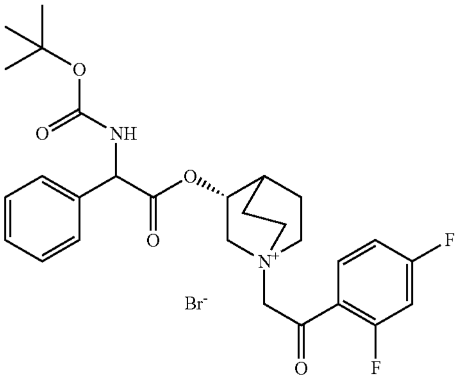 [SMILES: CC(C)(C)OC(=O)NC(C(=O)O[C@H]1C[N+]2(CC(=O)c3ccc(F)cc3F)CCC1CC2)c1ccccc1 ; [Br-]]<br>Mixture of diastereoisomers | 99% | LC-MS (ESI POS): 515.10 ($M^+$)<br>$^{1}$H NMR (300 MHz, DMSO-$d_6$) δ ppm 7.96-8.19 (m, 1 H), 7.88 (d, 1 H), 7.26-7.63 (m, 7 H), 5.11-5.44 (m, 2 H), 4.88-5.04 (m, 1 H), 3.95-4.22 (m, 1 H), 3.45-3.84 (m, 5 H), 2.14-2.23 and 2.32-2.42 (m, 1 H), 1.53-2.13 (m, 4 H), 1.42 (s, 9 H) |

TABLE 1-continued

| Compound | Structure | Yield | Analytical |
|---|---|---|---|
| C8 | 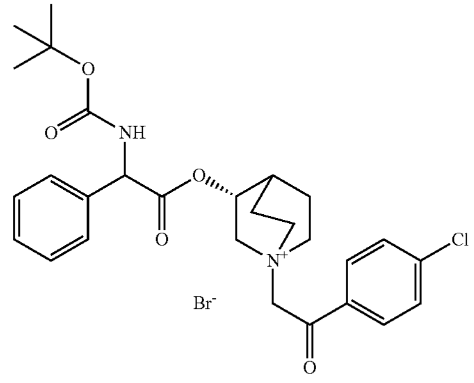 [SMILES: CC(C)(C)OC(=O)NC(C(=O)O[C@H]1C[N+]2(CC(=O)c3ccc(Cl)cc3)CCC1CC2)c1ccccc1 ; [Br-]] Mixture of diastereoisomers | 52% | LC-MS (ESI POS): 531.31 ($M^+$) $^1H$ NMR (300 MHz, DMSO-$d_6$) δ ppm 7.93-8.04 (m, 2 H), 7.88 (d, 1 H), 7.66-7.76 (m, 2 H), 7.30-7.52 (m, 5 H), 5.26-5.38 (m, 1 H), 5.16-5.25 (m, 1 H), 5.04-5.16 (m, 1 H), 3.94-4.23 (m, 1 H), 3.43-3.82 (m, 5 H), 2.19 and 2.37 (br. s., 1 H), 1.53-2.12 (m, 4 H), 1.41 (s, 9 H) |
| C9 | 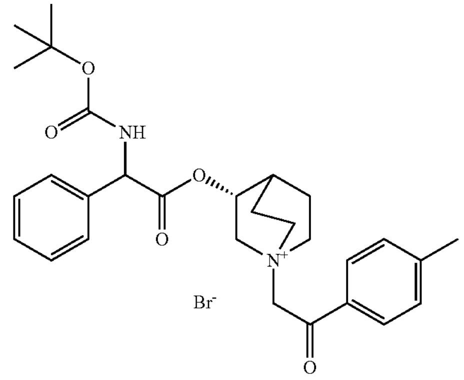 [SMILES: Cc1ccc(C(=O)C[N+]23CCC(CC2)[C@@H](OC(=O)C(NC(=O)OC(C)(C)C)c2ccccc2)C3)cc1 ; [Br-]] Mixture of diastereoisomers | 55% | LC-MS (ESI POS): 493.27 ($M^+$) $^1H$ NMR (300 MHz, DMSO-$d_6$) δ ppm 7.81-7.93 (m, 3 H), 7.26-7.51 (m, 7 H), 5.25-5.37 (m, 1 H), 5.14-5.25 (m, 1 H), 4.97-5.14 (m, 1 H), 3.94-4.19 (m, 1 H), 3.45-3.82 (m, 5 H), 2.42 (s, 3 H), 2.19 and 2.37 (br. s., 1 H), 1.54-2.13 (m, 4 H), 1.41 (s, 9 H) |
| C10 | 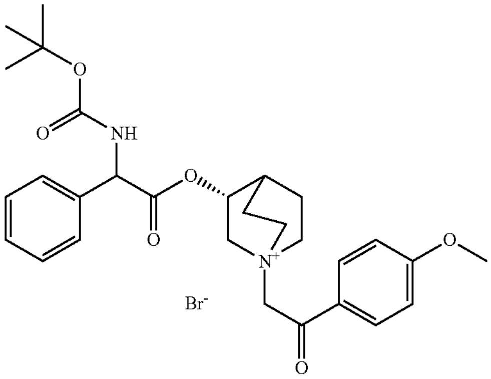 [SMILES: COc1ccc(C(=O)C[N+]23CCC(CC2)[C@@H](OC(=O)C(NC(=O)OC(C)(C)C)c2ccccc2)C3)cc1 ; [Br-]] Mixture of diastereoisomers | 64% | LC-MS (ESI POS): 509.3 ($M^+$) $^1H$ NMR (300 MHz, DMSO-$d_6$) δ ppm 7.91-8.07 (m, 2 H), 7.88 (d, 1 H), 7.26-7.54 (m, 5 H), 6.99-7.22 (m, 2 H), 5.25-5.42 (m, 1 H), 5.16-5.25 (m, 1 H), 5.03-5.16 (m, 2 H), 3.99-4.24 (m, 1 H), 3.88 (s, 3 H), 3.45-3.80 (m, 5 H), 2.15-2.22 and 2.31-2.40 (m, 1 H), 1.49-2.14 (m, 4 H), 1.41 (s, 9 H) |

TABLE 1-continued

| Compound | Structure | Yield | Analytical |
|---|---|---|---|
| C11 | 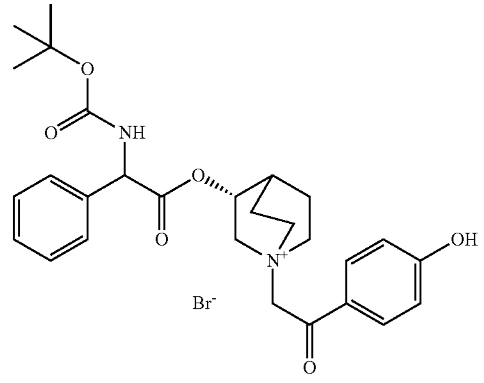 [SMILES: CC(C)(C)OC(=O)NC(C(=O)O[C@H]1C[N+]2(CC(=O)c3ccc(O)cc3)CCC1CC2)c1ccccc1 ; [Br-]] Mixture of diastereoisomers | 87% | LC-MS (ESI POS): 495.24 ($M^+$) $^1H$ NMR (300 MHz, DMSO-$d_6$) δ ppm 10.70 (br. s., 1 H), 7.75-7.98 (m, 2 H), 7.25-7.56 (m, 5 H), 6.86-6.96 (m, 2 H), 5.10-5.40 (m, 2 H), 4.94-5.06 (m, 1 H), 3.97-4.21 (m, 1 H), 3.45-3.87 (m, 5 H), 2.31-2.42 (m, 1 H), 1.53-2.09 (m, 4 H), 1.41 (s, 9 H) |
| C12 | 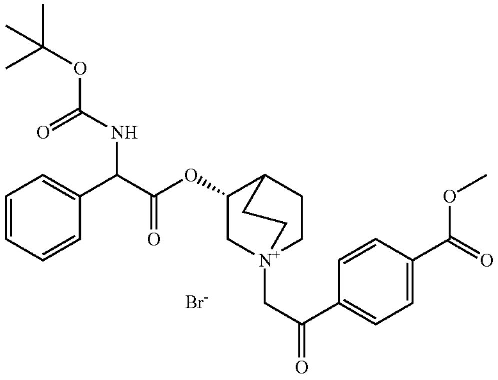 [SMILES: COC(=O)c1ccc(C(=O)C[N+]23CCC(CC2)[C@@H](OC(=O)C(NC(=O)OC(C)(C)C)c2ccccc2)C3)cc1 ; [Br-]] Mixture of diastereoisomers | 62% | LC-MS (ESI POS): 537.25 ($M^+$) $^1H$ NMR (300 MHz, DMSO-$d_6$) δ ppm 8.13-8.21 (m, 2 H), 8.04-8.13 (m, 2 H), 7.88 (d, 1 H), 7.31-7.54 (m, 5 H), 5.26-5.38 (m, 1 H), 5.08-5.26 (m, 2 H), 4.02-4.26 (m, 1 H), 3.91 (s, 3 H), 3.43-3.79 (m, 5 H), 2.19 and 2.37 (br. s., 1 H), 1.58-2.15 (m, 4 H), 1.41 (s, 9 H) |
| C13 | 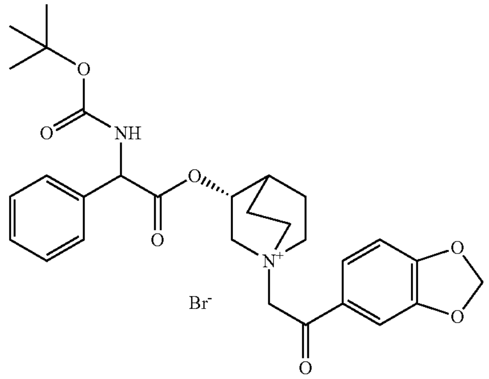 [SMILES: CC(C)(C)OC(=O)NC(C(=O)O[C@H]1C[N+]2(CC(=O)c3ccc4c(c3)OCO4)CCC1CC2)c1ccccc1 ; [Br-]] Mixture of diastereoisomers | 88% | LC-MS (ESI POS): 523.20 ($M^+$) $^1H$ NMR (300 MHz, DMSO-$d_6$) δ ppm 7.88 (d, 1 H), 7.57-7.68 (m, 1 H), 7.27-7.51 (m, 6 H), 7.14 (d, 1 H), 6.19 (s, 2 H), 5.12-5.41 (m, 2 H), 4.90-5.12 (m, 1 H), 3.89-4.26 (m, 1 H), 3.38-3.79 (m, 5 H), 2.15-2.23 and 2.31-2.41 (m, 1 H), 1.51-2.13 (m, 4 H), 1.41 (s, 9 H) |

TABLE 1-continued

| Compound | Structure | Yield | Analytical |
| --- | --- | --- | --- |
| C14 | 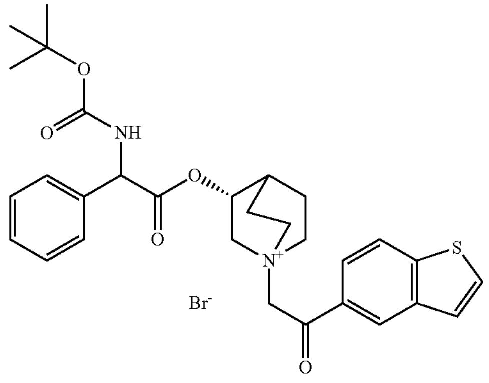 [SMILES: CC(C)(C)OC(=O)NC(C(=O)O[C@H]1C[N+]2(CC(=O)c3ccc4sccc4c3)CCC1CC2)c1ccccc1 ; [Br-]] Mixture of diastereoisomers | 90% | LC-MS (ESI POS): 535.06 ($M^+$) $^1H$ NMR (300 MHz, DMSO-$d_6$) δ ppm 8.56 and 8.58 (d, 1 H), 8.24 and 8.25 (d, 1 H), 7.81-8.03 (m, 2 H), 7.66 (d, 1 H), 7.32-7.53 (m, 5 H), 5.04-5.40 (m, 3 H), 3.97-4.25 (m, 1 H), 3.45-3.86 (m, 5 H), 2.16-2.24 and 2.34-2.41 (m, 1 H), 1.52-2.12 (m, 4 H), 1.42 (s, 9 H) |
| C15 | 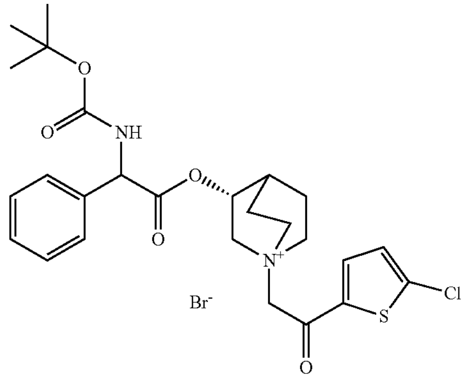 [SMILES: CC(C)(C)OC(=O)NC(C(=O)O[C@H]1C[N+]2(CC(=O)c3ccc(Cl)s3)CCC1CC2)c1ccccc1 ; [Br-]] Mixture of diastereoisomers | 87% | LC-MS (ESI POS): 519.03 ($M^+$) $^1H$ NMR (300 MHz, DMSO-$d_6$) δ ppm 7.80-8.12 (m, 2 H), 7.19-7.57 (m, 6 H), 5.09-5.38 (m, 2 H), 4.83-5.05 (m, 1 H), 3.97-4.16 (m, 1 H), 3.35-3.82 (m, 5 H), 2.13-2.23 and 2.32-2.40 (m, 1 H), 1.50-2.09 (m, 4 H), 1.41 (s, 9 H) |
| C16 | 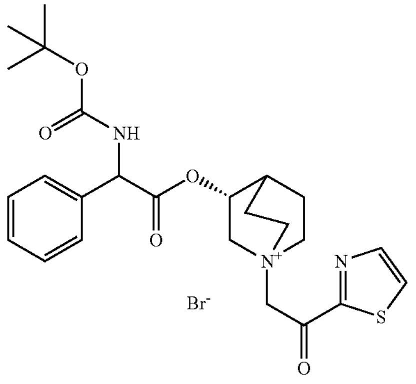 [SMILES: CC(C)(C)OC(=O)NC(C(=O)O[C@H]1C[N+]2(CC(=O)c3nccs3)CCC1CC2)c1ccccc1 ; [Br-]] Mixture of diastereoisomers | 83% | LC-MS (ESI POS): 486.20 ($M^+$) $^1H$ NMR (300 MHz, DMSO-$d_6$) δ ppm 8.36-8.41 (m, 1 H), 8.18-8.28 (m, 1 H), 7.88 (d, 1 H), 7.25-7.54 (m, 5 H), 5.24-5.40 (m, 1 H), 5.08-5.25 (m, 3 H), 3.97-4.25 (m, 1 H), 3.47-3.88 (m, 5 H), 2.13-2.24 and 2.32-2.42 (m, 1 H), 1.54-2.13 (m, 4 H), 1.41 (s, 9 H) |

Example 3

Preparation of (3R)-3-(2-(tert-butoxycarbonylamino)-2-phenylacetoxy)-1-(2-oxo-2-(thiophen-3-yl)ethyl)-1-azoniabicyclo[2.2.2]-octane bromide (C17)

Scheme 4

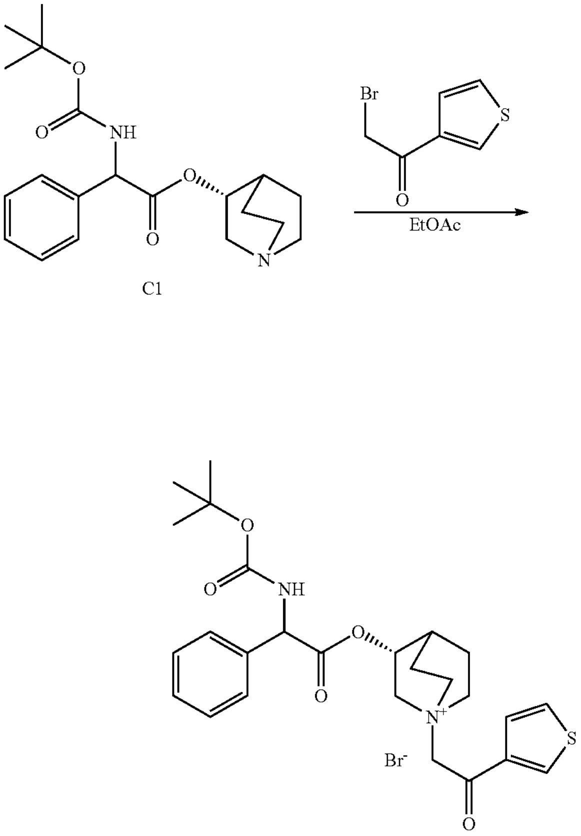

C1

C17

2-Bromo-1-(thiophen-3-yl)ethanone (39.8 mg, 0.19 mmol) was added to a solution of (R)-quinuclidin-3-yl 2-(tert-butoxycarbonylamino)-2-phenylacetate (C1) (70.0 mg, 0.19 mmol) in ethyl acetate (2 ml). The reaction was stirred at RT overnight. $Et_2O$ (1 ml) was added, and the solid was collected by suction filtration. The compound was further purified by flash chromatography (DCM/MeOH=95/5) to obtain (3R)-3-(2-(tert-butoxycarbonylamino)-2-phenylacetoxy)-1-(2-oxo-2-(thiophen-3-yl)ethyl)-1-azoniabicyclo[2.2.2]octane bromide (55.6 mg; 51% yield).

$^1H$ NMR (300 MHz, DMSO-$d_6$) δ ppm 8.60-8.65 (m, 1H) 7.88 (d, 1H) 7.75 and 7.73 (dd, 1H) 7.51-7.61 (m, 1H) 7.27-7.50 (m, 5H) 5.10-5.39 (m, 2H) 4.93-5.08 (m, 1H) 4.02-4.22 (m, 1H) 3.43-3.79 (m, 5H) 2.30-2.41 (m, 1H) 1.85-2.11 (m, 5H) 1.41 (s, 9H);

LC-MS (ESI POS): 485.06 (M+).

Example 4

Preparation of (3R)-3-(2-(tert-butoxycarbonylamino)-2-phenylacetoxy)-1-methyl-1-azoniabicyclo[2.2.2]octane iodide (C18)

Scheme 5

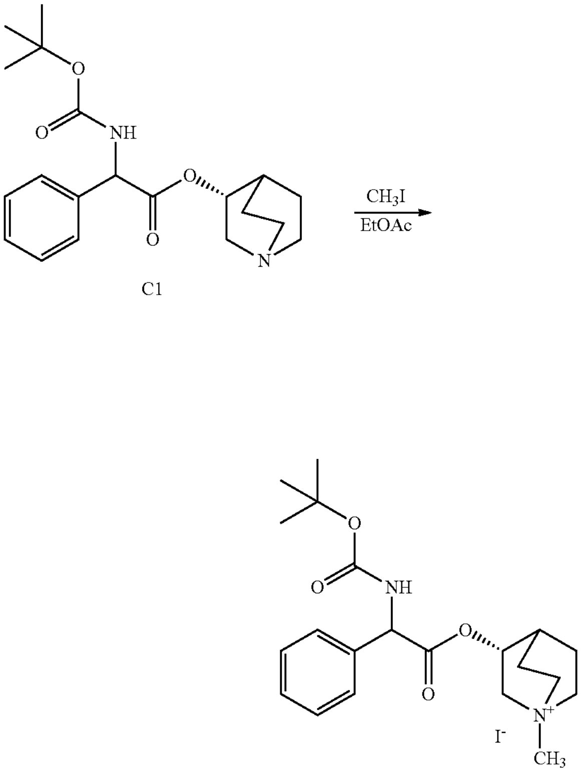

C1

C18

Methyl iodide (8.6 μl, 0.14 mmol) was added to a solution of (R)-quinuclidin-3-yl 2-(tert-butoxycarbonylamino)-2-phenylacetate (C1) (50 mg, 0.14 mmol) in ethyl acetate (2 ml), and the reaction was stirred at RT overnight. $Et_2O$ (1 ml) was added, and the precipitate was collected by suction filtration and dried under vacuum at 40° C. The product was further purified by preparative HPLC to obtain (3R)-3-(2-(tert-butoxycarbonylamino)-2-phenylacetoxy)-1-methyl-1-azoniabicyclo[2.2.2]octane iodide (24.2 mg; 35% yield).

$^1H$ NMR (300 MHz, DMSO-$d_6$) δ ppm 7.85 (d, 1H) 7.20-7.55 (m, 5H) 5.26 and 5.31 (d, 1H) 4.93-5.18 (m, 1H) 3.83 (ddd, 1H) 3.30-3.53 (m, 3H) 3.09-3.27 (m, 1H) 3.16 (dt, 1H) 2.93 and 2.95 (s, 3H) 2.04-2.14 and 2.25-2.33 (m, 1H) 1.52-2.03 (m, 4H) 1.40 (s, 9H);

LC-MS (ESI POS): 375.20 (M+).

The compound listed in Table 2 was obtained as previously described for C18, starting from intermediate C1 and (3-bromopropoxy)benzene.

TABLE 2

| Compound | Structure | Yield | Analytical |
|---|---|---|---|
| C19 | 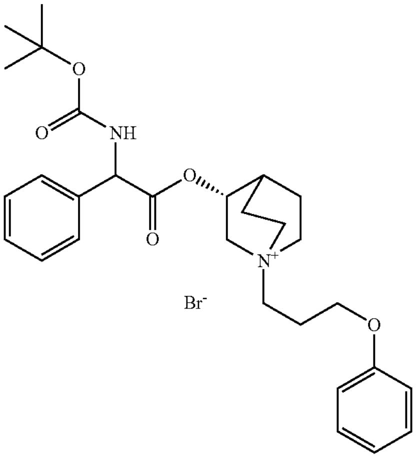 [SMILES: CC(C)(C)OC(=O)NC(C(=O)O[C@H]1C[N+]2(CCCOc3ccccc3)CCC1CC2)c1ccccc1 ; [Br-]]<br>Mixture of diastereoisomers | 39% | LC-MS (ESI POS): 495.28 ($M^+$)<br>$^1H$ NMR (300 MHz, DMSO-$d_6$) δ ppm 7.87 (d, 1 H) 7.18-7.58 (m, 7 H) 6.81-7.08 (m, 3 H) 5.27 and 5.32 (d, 1 H) 5.00-5.20 (m, 1 H) 4.02 and 4.04 (t, 2 H) 3.73-3.95 (m, 1 H) 3.31-3.55 (m, 6 H) 2.97-3.20 (m, 1 H) 2.29-2.39 (m, 1 H) 1.51-2.22 (m, 6 H) 1.40 (s, 9 H) |

Example 5

Preparation of (3R)-3-(2-(tert-butoxycarbonylamino)-2-phenylacetoxy)-1-(2-(2-methoxyphenyl)-2-oxoethyl)-1-azoniabicyclo[2.2.2]octane bromide (C20)

Scheme 6

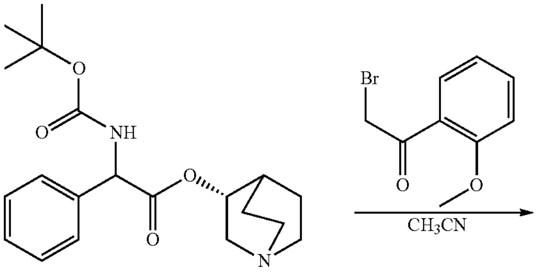

C1

-continued

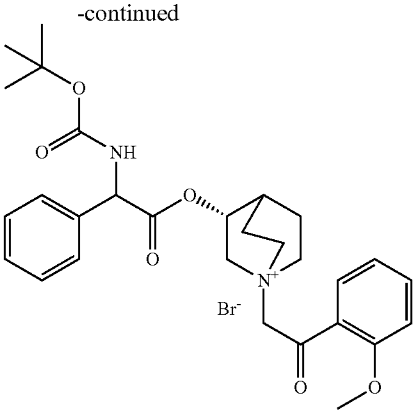

C20

2-Bromo-1-(2-methoxyphenyl)ethanone (45.8 mg, 0.20 mmol) was added to a solution of (R)-quinuclidin-3-yl 2-(tert-butoxycarbonylamino)-2-phenylacetate (C1) (72.0 mg, 0.20 mmol) in acetonitrile (3 ml). The reaction was stirred at RT overnight. The product was collected by suction filtration to get (3R)-3-(2-(tert-butoxycarbonylamino)-2-phenylacetoxy)-1-(2-(2-methoxyphenyl)-2-oxoethyl)-1-azoniabicyclo[2.2.2]octane bromide (112 mg; 95% yield).

$^1H$ NMR (300 MHz, DMSO-$d_6$) δ ppm 7.88 (d, 1H), 7.76-7.84 (m, 1H), 7.64-7.75 (m, 1H), 7.30-7.54 (m, 5H), 7.23-7.30 (m, 1H), 7.03-7.19 (m, 1H), 5.24-5.36 (m, 1H), 5.11-5.24 (m, 1H), 4.89 (s, 2H), 4.03-4.23 (m, 1H), 3.95 and 3.96 (s, 3H), 3.45-3.84 (m, 5H), 2.13-2.23 and 2.31-2.42 (m, 1H), 1.51-2.12 (m, 4H), 1.41 (s, 9H);

LC-MS (ESI POS): 509.33 (M+).

The compound listed in Table 3 was obtained as previously described for C20, starting from intermediate C1 and 3-(chloromethyl)-5-phenyl-1,2,4-oxadiazole.

TABLE 3

| Compound | Structure | Yield | Analytical |
| --- | --- | --- | --- |
| C21 | 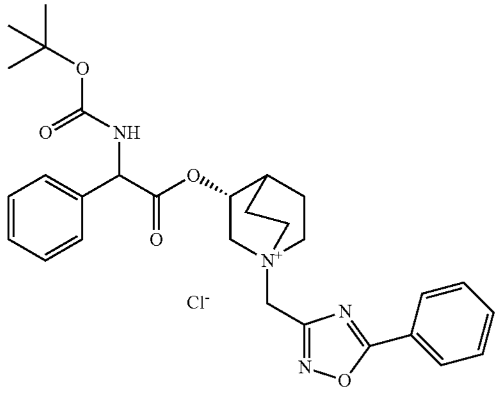 [SMILES: CC(C)(C)OC(=O)NC(C(=O)O[C@H]1C[N+]2(Cc3noc(-c4ccccc4)n3)CCC1CC2)c1ccccc1 ; [Cl-]]<br>Mixture of diastereoisomers | 97% | LC-MS (ESI POS): 519.33 ($M^+$)<br>$^1H$ NMR (300 MHz, DMSO-$d_6$) δ ppm 8.09-8.28 (m, 2 H), 7.84-7.97 (m, 1 H), 7.62-7.84 (m, 3 H), 7.18-7.51 (m, 5 H), 5.25 and 5.32 (d, 1 H), 5.04-5.16 (m, 1 H), 4.87 (s, 2 H), 3.99-4.25 (m, 1 H), 3.35-3.82 (m, 5 H), 2.13-2.23 and 2.29-2.40 (m, 1 H), 1.52-2.09 (m, 4 H), 1.37 and 1.39 (s, 9 H) |

Example 6

Preparation of (3R)-1-(2-tert-butoxy-2-oxoethyl)-3-(2-(tert-butoxycarbonylamino)-2-phenylacetoxy)-1-azoniabicyclo[2.2.2]octane bromide (C22)

Scheme 7

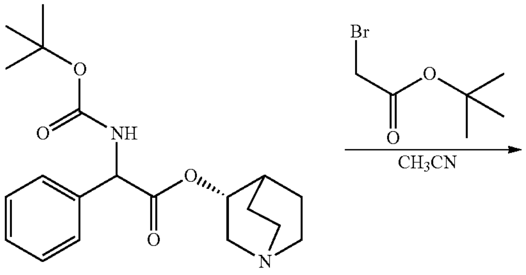

C1

-continued

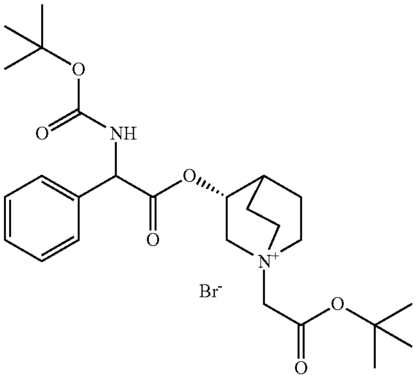

C22

Tert-butyl 2-bromoacetate (29.5 μl, 0.20 mmol) was added to a solution of (R)-quinuclidin-3-yl 2-(tert-butoxycarbonylamino)-2-phenylacetate (C1) (72 mg, 0.20 mmol) in acetonitrile (3 ml). The reaction was stirred at RT overnight. The product was collected by suction filtration and then purified by flash chromatography (DCM/MeOH=98/2 to 95/5) to get (3R)-1-(2-tert-butoxy-2-oxoethyl)-3-(2-(tert-butoxycarbonylamino)-2-phenylacetoxy)-1-azoniabicyclo[2.2.2]octane bromide (97 mg; 87% yield).

$^1H$ NMR (300 MHz, DMSO-$d_6$) δ ppm 7.87 (d, 1H), 7.20-7.54 (m, 5H), 5.23-5.44 (m, 1H), 5.08-5.22 (m, 1H), 4.21 and 4.23 (s, 2H), 3.88-4.08 (m, 1H), 3.37-3.72 (m, 5H), 2.09-2.22 and 2.30-2.40 (m, 1H), 1.76-2.08 (m, 4H), 1.46 and 1.48 (s, 9H), 1.41 (s, 9H);

LC-MS (ESI POS): 475.33 (M+).

The compounds listed in Table 4 were obtained as previously described for C22, starting from intermediate C1 and 2-bromo-1-(2-nitrophenyl)ethanone or 2-bromo-1-(2-hydroxyphenyl)ethanone.

TABLE 4

| Compound | Structure | Yield | Analytical |
|---|---|---|---|
| C23 | 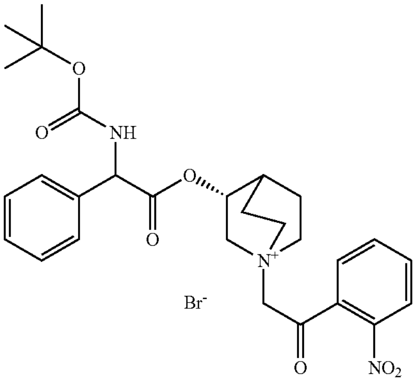 [SMILES: CC(C)(C)OC(=O)NC(C(=O)O[C@H]1C[N+]2(CC(=O)c3ccccc3[N+](=O)[O-])CCC1CC2)c1ccccc1 ; [Br-]] Mixture of diastereoisomers | 54% | LC-MS (ESI POS): 524.27 ($M^+$) $^1H$ NMR (300 MHz, DMSO-$d_6$) δ ppm 8.30 (m, 1 H), 7.94-8.08 (m, 1 H), 7.74-7.94 (m, 3 H), 7.24-7.55 (m, 5 H), 5.26-5.36 (m, 1 H), 5.18-5.27 (m, 1 H), 5.02 and 5.05 (s, 2 H), 4.04-4.25 (m, 1 H), 3.45-3.81 (m, 5 H), 2.17-2.25 and 2.30-2.43 (m, 1 H), 1.54-2.16 (m, 4 H), 1.41 (s, 9 H) |
| C24 | 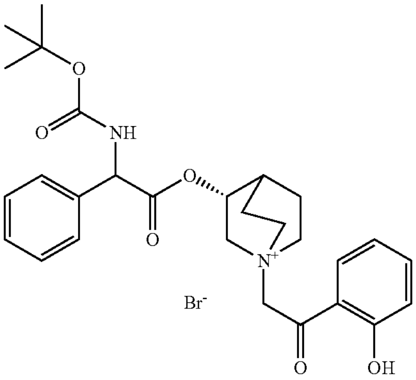 [SMILES: CC(C)(C)OC(=O)NC(C(=O)O[C@H]1C[N+]2(CC(=O)c3ccccc3O)CCC1CC2)c1ccccc1 ; [Br-]] Mixture of diastereoisomers | 56% | LC-MS (ESI POS): 495.32 ($M^+$) $^1H$ NMR (300 MHz, DMSO-$d_6$) δ ppm 11.17 (br. s., 1 H), 7.82-7.94 (m, 1 H), 7.73-7.82 (m, 1 H), 7.50-7.63 (m, 1 H), 7.43-7.50 (m, 2 H), 7.25-7.43 (m, 3 H), 7.01-7.10 (m, 1 H), 6.91-7.01 (m, 1 H), 5.24-5.44 (m, 1 H), 5.07-5.25 (m, 1 H), 4.83-5.07 (m, 2 H), 3.96-4.23 (m, 1 H), 3.46-3.83 (m, 5 H), 2.13-2.24 and 2.31-2.42 (m, 1 H), 1.47-2.12 (m, 4 H), 1.41 (s, 9 H) |

Example 7

Preparation of (3R)-3-(2-(methoxycarbonylamino)-2-phenylacetoxy)-1-(2-oxo-2-phenylethyl)-1-azoni-abicyclo[2.2.2]octane bromide (C27)

Scheme 8

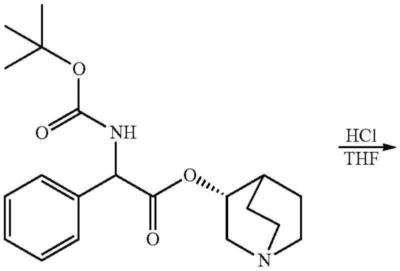

C1

-continued

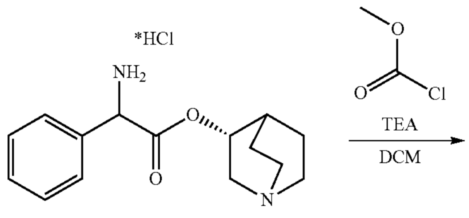

I25

-continued

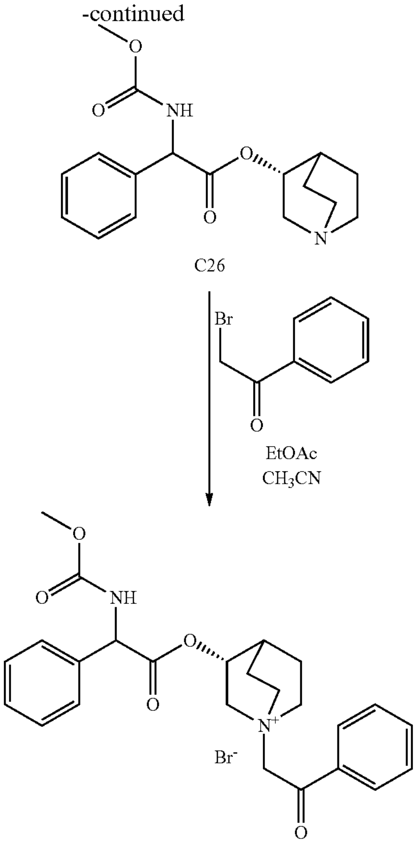

C26

C27

Preparation of (R)-quinuclidin-3-yl 2-amino-2-phenylacetate dihydrochloride (I25)

To a solution of (R)-quinuclidin-3-yl 2-(tert-butoxycarbonylamino)-2-phenylacetate (C1) (1.25 g, 3.47 mmol) in THF (20 ml), was added 37% hydrogen chloride (2.00 ml, 24.3 mmol) dropwise. The reaction was stirred at RT for 15 hours. The solvent was evaporated to obtain (R)-quinuclidin-3-yl 2-amino-2-phenylacetate dihydrochloride (1.16 g; quantitative yield) as a solid. The compound was used in the next step without any further purification.

Preparation of (R)-quinuclidin-3-yl 2-(methoxycarbonylamino)-2-phenylacetate (C26)

To a suspension of (R)-quinuclidin-3-yl 2-amino-2-phenylacetate dihydrochloride (I25) (150 mg, 0.45 mmol) in DCM (5 ml), were added triethylamine (188 μl, 1.35 mmol) and methyl carbonochloridate (41.7 μl, 0.54 mmol). The reaction was stirred at RT for 4 hours, and then the solvent was evaporated. The residue was taken up with EtOAc and washed with water and brine. The organic phase was dried over $Na_2SO_4$ and evaporated to obtain (R)-quinuclidin-3-yl 2-(methoxycarbonylamino)-2-phenylacetate (58.0 mg; 40% yield). The compound was used in the next step without any further purification.

Preparation of (3R)-3-(2-(methoxycarbonylamino)-2-phenylacetoxy)-1-(2-oxo-2-phenylethyl)-1-azoniabicyclo[2.2.2]octane bromide (C27)

To a solution of (R)-quinuclidin-3-yl 2-(methoxycarbonylamino)-2-phenylacetate (C26) (58.0 mg, 0.18 mmol) in EtOAc (3 ml) and $CH_3CN$ (1 ml), was added 2-bromo-1-phenylethanone (39.9 mg, 0.20 mmol). The reaction was stirred at RT for 15 hours, and then the solvent was evaporated. The crude was purified by flash chromatography (DCM/MeOH=95/5 to 92/8) and the resulting product was triturated with i-$Pr_2O$ to obtain (3R)-3-(2-(methoxycarbonylamino)-2-phenylacetoxy)-1-(2-oxo-2-phenylethyl)-1-azoniabicyclo[2.2.2]octane bromide (55.2 mg; 58.6% yield).

$^1H$ NMR (300 MHz, DMSO-d6) δ ppm 8.17-8.30 (m, 1H) 7.98 (dd, 2H) 7.71-7.84 (m, 1H) 7.61 (td, 2H) 7.30-7.52 (m, 5H) 5.36 (dd, 1H) 5.20-5.30 (m, 1H) 5.16 (d, 2H) 4.01-4.23 (m, 1H) 3.61 (s, 3H) 3.45-3.81 (m, 5H) 2.39 (s, 1H) 1.90-2.11 (m, 3H) 1.54-1.71 (m, 1H);

LC-MS (ESI POS): 437.12 (M+).

Example 8

Preparation of (R)-quinuclidin-3-yl 2-amino-2-phenylacetate (I30)

Scheme 9

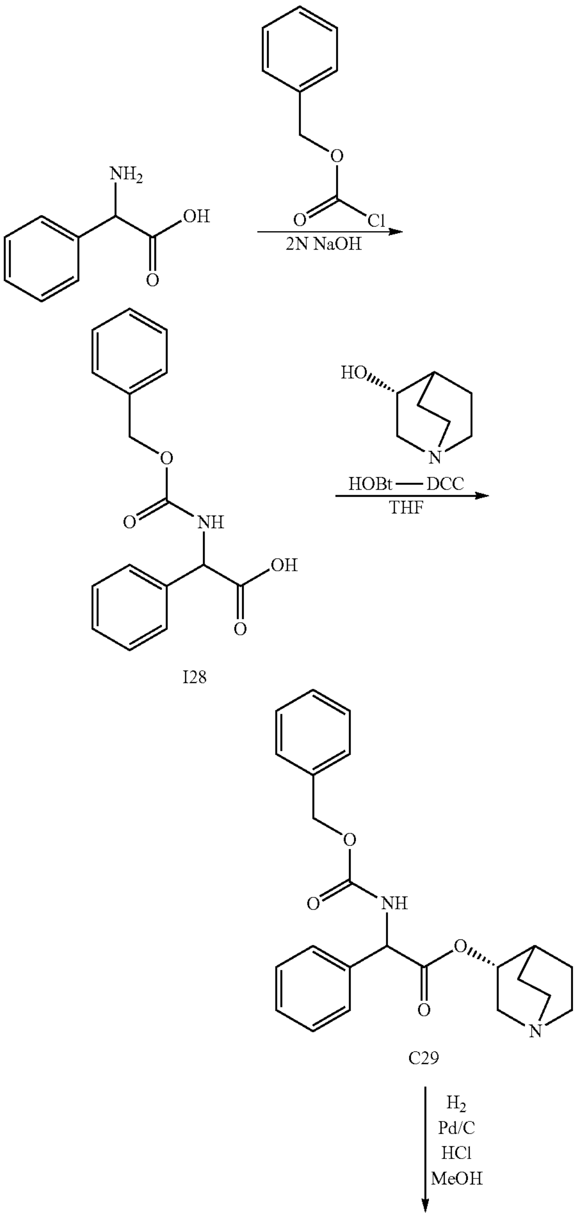

I28

C29

-continued

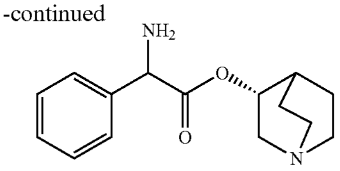

I30

Preparation of 2-(benzyloxycarbonylamino)-2-phenylacetic acid (I28)

To a solution of 2-amino-2-phenylacetic acid (500 mg, 3.31 mmol) in 2N sodium hydroxide (1.65 ml, 3.31 mmol) stirred at 0° C., benzyl carbonochloridate (512 μl, 3.64 mmol) and 2N sodium hydroxide (1.82 ml, 3.64 mmol) were simultaneously added dropwise from two different syringes. The reaction was stirred at RT for 45 minutes, and a precipitate appeared. Water was added, and the solution was extracted with $Et_2O$. The aqueous phase was acidified with 1N HCl and the desired product was extracted again with $Et_2O$. The combined organic phases were dried over $Na_2SO_4$, filtered and evaporated to obtain 2-(benzyloxycarbonylamino)-2-phenylacetic acid (855 mg; 91% yield).

Preparation of (R)-quinuclidin-3-yl 2-(benzyloxycarbonylamino)-2-phenylacetate (C29)

To a solution of 2-(benzyloxycarbonylamino)-2-phenylacetic acid (I28) (855 mg, 3.00 mmol) in THF (20 ml), were added (R)-quinuclidin-3-ol (457 mg, 3.60 mmol), N,N'-methanediylidenedicyclohexanamine (742 mg, 3.60 mmol) and 1H-benzo[d][1,2,3]triazol-1-ol (486 mg, 3.60 mmol). The reaction was stirred at RT for 15 hours, and then the solvent was evaporated. The residue was taken up with DCM, the insoluble solid was filtered off, and the clear solution was washed twice with $Na_2CO_3$ and brine, dried over $Na_2SO_4$ and evaporated. The resulting crude is purified by silica gel flash chromatography (DCM/MeOH=9/1) to obtain (R)-quinuclidin-3-yl 2-(benzyloxy-carbonylamino)-2-phenylacetate (925 mg; 78% yield).

$^1H$ NMR (300 MHz, DMSO-$d_6$) δ ppm 8.26 (d, 1H), 7.19-7.54 (m, 10H), 5.28 and 5.29 (d, 1H), 5.10 (d, 1H), 5.05 (d, 1H), 4.59-4.80 (m, 1H), 2.95-3.07 (m, 1H), 2.09-2.71 (m, 5H), 1.70-1.80 and 1.81-1.99 (m, 1H), 1.01-1.70 (m, 4H).

Preparation of (R)-quinuclidin-3-yl 2-amino-2-phenylacetate dihydrochloride (I30)

A solution of (R)-quinuclidin-3-yl 2-(benzyloxycarbonylamino)-2-phenylacetate (C29) (100 mg, 0.25 mmol) in MeOH (7 ml) and 37% hydrogen chloride (20.8 μl, 0.25 mmol) was stirred at RT under hydrogen atmosphere (25 psi) for 3 hours in a Parr apparatus, in presence of palladium on activate carbon (10 mg, 9.40 μmol). The catalyst was removed by filtration, and the solvent was evaporated. The resulting oil was purified by SCX cartridge eluting with MeOH and then $MeOH/NH_4OH$ (97/3) to obtain (R)-quinuclidin-3-yl 2-amino-2-phenylacetate dihydrochloride (55.0 mg; 65.1% yield).

Example 9

Preparation of (3R)-3-(2-(benzyloxycarbonylamino)-2-phenylacetoxy)-1-(2-oxo-2-phenylethyl)-1-azoniabicyclo[2.2.2]octane bromide (C31)

Scheme 10

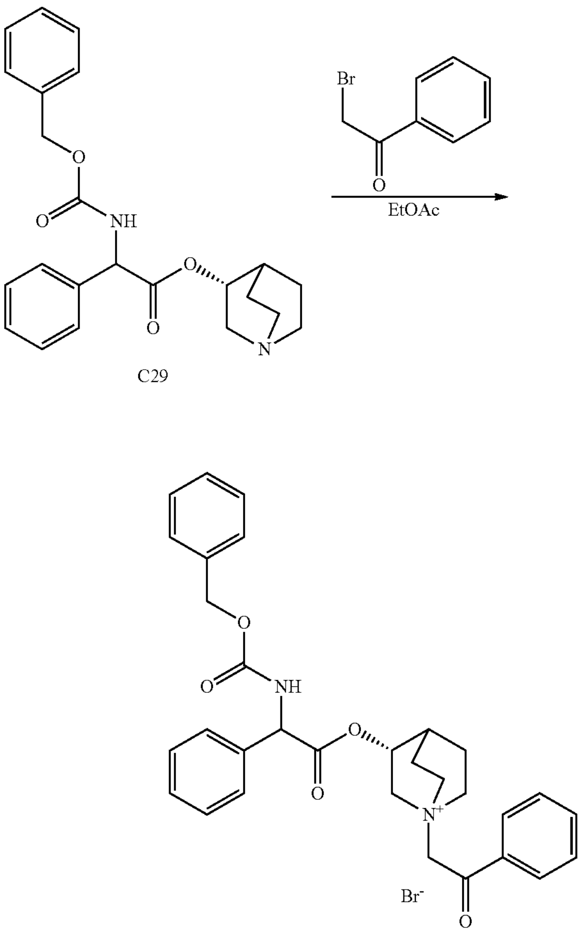

C29

C31

To a solution of (R)-quinuclidin-3-yl 2-(benzyloxycarbonylamino)-2-phenylacetate (C29) (100 mg, 0.25 mmol) in EtOAc (5 ml), was added 2-bromo-1-phenylethanone (55.5 mg, 0.28 mmol), and the reaction was stirred at RT for 15 hours. The solvent was evaporated, and the resulting crude was purified by silica gel flash chromatography (DCM/MeOH=93/7) to obtain (3R)-3-(2-(benzyloxycarbonylamino)-2-phenylacetoxy)-1-(2-oxo-2-phenylethyl)-1-azoniabicyclo[2.2.2]octane bromide (127.5 mg; 85% yield).

$^1H$ NMR (300 MHz, DMSO-$d_6$) δ ppm 8.22-8.52 (m, 1H), 7.90-8.07 (m, 2H), 7.69-7.83 (m, 1H), 7.54-7.69 (m, 2H), 7.19-7.54 (m, 10H), 5.39 and 5.40 (d, 1H), 4.99-5.29 (m, 5H), 3.93-4.23 (m, 1H), 3.39-3.78 (m, 5H), 2.10-2.23 and 2.30-2.44 (m, 1H), 1.40-2.12 (m, 4H);

LC-MS (ESI POS): 513.25 (M+).

Example 10

Preparation of (R)—((R)-quinuclidin-3-yl) 2-(benzyloxycarbonylamino)-2-phenylacetate (Diastereoisomer 1 of C31)

Scheme 11

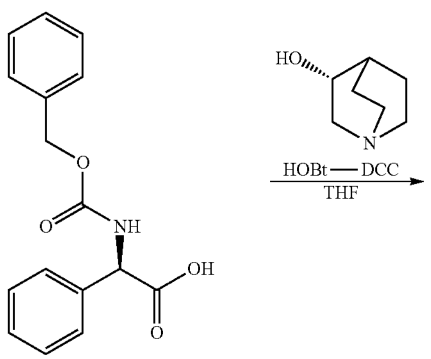

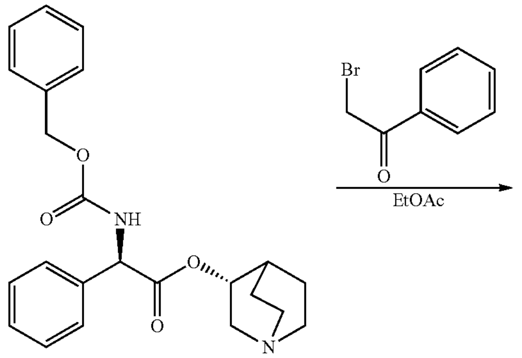

Diastereoisomer 1 of C29

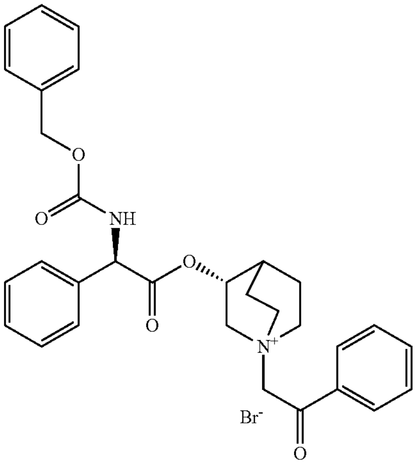

Diastereoisomer 1 of C31

Preparation of (R)—((R)-quinuclidin-3-yl) 2-(benzyloxycarbonylamino)-2-phenylacetate (Diastereoisomer 1 of C29)

(R)-quinuclidin-3-ol (214 mg, 1.68 mmol), N,N'-methanediylidenedicyclohexanamine (347 mg, 1.68 mmol) and 1H-benzo[d][1,2,3]triazol-1-ol (227 mg, 1.68 mmol) were added to a solution of (R)-2-(benzyloxycarbonylamino)-2-phenylacetic acid (400 mg, 1.40 mmol) in THF (15 ml). The reaction was stirred at RT for 15 hours, and then the solvent was evaporated. DCM was added, and the insoluble solid was removed by filtration. The organic phase was washed twice with $Na_2CO_3$ and brine, dried over $Na_2SO_4$ and evaporated. The crude was purified by silica gel flash chromatography (DCM/MeOH=9/1) to obtain (R)—((R)-quinuclidin-3-yl) 2-(benzyloxycarbonylamino)-2-phenylacetate (63 mg; 11.4% yield). ((R)-quinuclidin-3-yl 2-(benzyloxycarbonylamino)-2-phenylacetate is also collected (300 mg; 54.2% yield)).

$^1$H NMR (300 MHz, DMSO-$d_6$) δ ppm 8.26 (d, 1H), 7.14-7.58 (m, 10H), 5.28 (d, 1H), 5.10 (d, 1H), 5.05 (d, 1H), 4.59-4.79 (m, 1H), 3.01 (dd, 1H), 2.54-2.70 (m, 3H), 2.32-2.45 (m, 1H), 2.22 (d, 1H), 1.82-1.99 (m, 1H), 1.35-1.68 (m, 3H), 1.16-1.35 (m, 1H).

Preparation of (R)-3-((R)-2-(benzyloxycarbonylamino)-2-phenylacetoxy)-1-(2-oxo-2-phenylethyl)-1-azoniabicyclo[2.2.2]octane bromide (Diastereoisomer 1 of C31)

To a solution of (R)—((R)-quinuclidin-3-yl) 2-(benzyloxy-carbonylamino)-2-phenylacetate (40 mg, 0.10 mmol) in EtOAc (3 ml), 2-bromo-1-phenylethanone (22.2 mg, 0.11 mmol) was added and the reaction was stirred at RT for 15 hours, and then the solvent was evaporated. The crude was purified by silica gel flash chromatography (DCM/MeOH=93/7) to obtain (R)-3-((R)-2-(benzyloxycarbonylamino)-2-phenylacetoxy)-1-(2-oxo-2-phenylethyl)-1-azoniabicyclo[2.2.2]octane bromide (45.0 mg; 74.8% yield).

$^1$H NMR (300 MHz, DMSO-$d_6$) δ ppm 8.37 (d, 1H), 7.87-8.04 (m, 2H), 7.69-7.82 (m, 1H), 7.56-7.69 (m, 2H), 7.18-7.54 (m, 10H), 5.38 (d, 1H), 5.17-5.26 (m, 1H), 5.15 (s, 2H), 5.09 (s, 2H), 3.95-4.21 (m, 1H), 3.42-3.75 (m, 5H), 2.31-2.44 (m, 1H), 1.39-2.12 (m, 4H);

LC-MS (ESI POS): 513.17 (M+).

Example 11

Preparation of (3R)-1-(2-oxo-2-phenylethyl)-3-(2-phenyl-2-(vinyloxycarbonylamino)acetoxy)-1-azoniabicyclo[2.2.2]octane bromide (C33)

Scheme 12

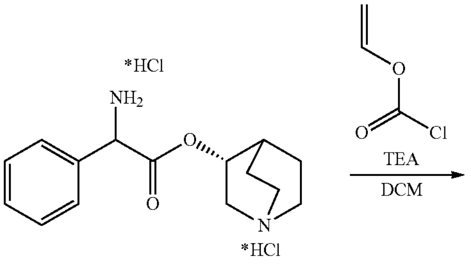

I25

-continued

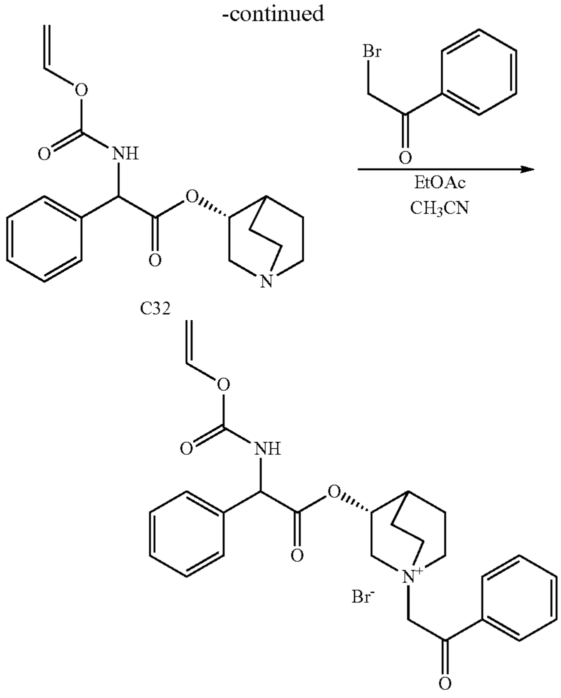

C32

C33

Preparation of (R)-quinuclidin-3-yl 2-phenyl-2-(vinyloxycarbonylamino)acetate (C32)

To a suspension of (R)-quinuclidin-3-yl 2-amino-2-phenylacetate dihydrochloride (I25) (110 mg, 0.33 mmol) in DCM (5 ml), were added triethylamine (138 μl, 0.99 mmol) and vinyl carbonochloridate (36.2 μl, 0.40 mmol). The reaction was stirred at RT for 4 hours, and then the solvent was evaporated. The residue was taken up with EtOAc and washed with water and brine, dried over $Na_2SO_4$ and evaporated to dryness to obtain (R)-quinuclidin-3-yl 2-phenyl-2-(vinyloxycarbonylamino)acetate (70 mg; 64% yield). The product was used in the next step without any further purification.

Preparation of (3R)-1-(2-oxo-2-phenylethyl)-3-(2-phenyl-2-(vinyloxycarbonylamino)acetoxy)-1-azoniabicyclo[2.2.2]octane bromide (C33)

To a solution of (R)-quinuclidin-3-yl 2-phenyl-2-(vinyloxycarbonylamino)acetate (C32) (70.0 mg, 0.21 mmol) in EtOAc (2 ml) and acetonitrile (0.5 ml), was added 2-bromo-1-phenylethanone (46.4 mg, 0.23 mmol). The reaction was stirred at RT for 15 hours, and then the solvent was evaporated. The resulting solid was triturated with i-$Pr_2O$/EtOAc (1/1) to obtain (3R)-1-(2-oxo-2-phenylethyl)-3-(2-phenyl-2-(vinyloxycarbonylamino)-acetoxy)-1-azoniabicyclo[2.2.2] octane bromide (82.4 mg; 73% yield).

$^1H$ NMR (300 MHz, DMSO-d6) δ ppm 8.76 and 8.78 (d, 1H), 7.90-8.08 (m, 2H), 7.71-7.80 (m, 1H), 7.56-7.67 (m, 2H), 7.30-7.54 (m, 5H), 7.07-7.20 (m, 1H), 5.41 and 5.42 (d, 1H), 5.20-5.30 (m, 1H), 5.15 and 5.17 (s, 2H), 4.78 (dd, 1H), 4.53 (dd, 1H), 3.97-4.22 (m, 1H), 3.43-3.83 (m, 5H), 2.15-2.24 and 2.35-2.44 (m, 1H), 1.50-2.14 (m, 4H);

LC-MS (ESI POS): 449.27 (M+).

Example 12

Preparation of (3R)-3-(2-(ethoxycarbonylamino)-2-phenylacetoxy)-1-(2-oxo-2-phenylethyl)-1-azoniabicyclo[2.2.2]octane bromide (C35)

Scheme 13

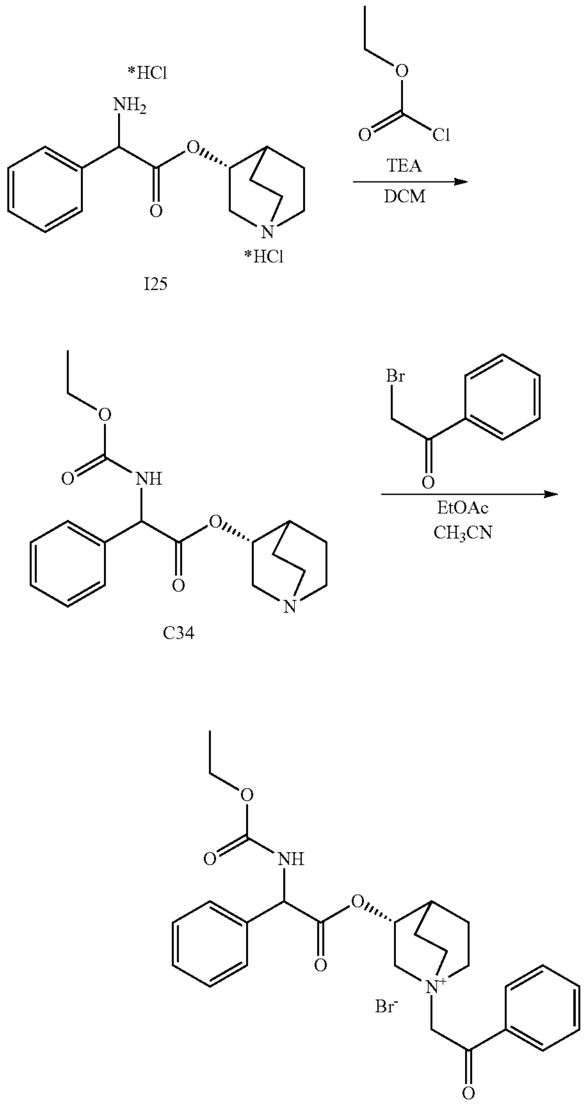

I25

C34

C35

Preparation of (R)-quinuclidin-3-yl 2-(ethoxycarbonylamino)-2-phenylacetate (C34)

To a suspension of (R)-quinuclidin-3-yl 2-amino-2-phenylacetate dihydrochloride (I25) (110 mg, 0.33 mmol) in DCM (5 ml), were added triethylamine (138 μl, 0.99 mmol) and ethyl carbonochloridate (38 μl, 0.40 mmol). The reaction was stirred at RT for 4 hours, and then solvent was evaporated. EtOAc was added, and the organic phase was washed with water and brine, dried over $Na_2SO_4$ and evaporated to obtain (R)-quinuclidin-3-yl 2-(ethoxycarbonylamino)-2-phenylacetate (60 mg; 55% yield). The product was used as such in the next step.

Preparation of (3R)-3-(2-(ethoxycarbonylamino)-2-phenylacetoxy)-1-(2-oxo-2-phenylethyl)-1-azoniabicyclo[2.2.2]octane bromide (C35)

To a solution of (R)-quinuclidin-3-yl 2-(ethoxycarbonylamino)-2-phenylacetate (C34) (60.0 mg, 0.18 mmol) in EtOAc (2 ml) and acetonitrile (0.5 ml), was added 2-bromo-1-phenylethanone (39.5 mg, 0.20 mmol). The reaction was stirred at RT for 15 hours, and the solvent was evaporated. The resulting solid was triturated in i-$Pr_2O$/EtOAc (1/1) to obtain (3R)-3-(2-(ethoxycarbonylamino)-2-phenylacetoxy)-1-(2-oxo-2-phenylethyl)-1-azoniabicyclo[2.2.2]octane bromide (76 mg; 80% yield).

$^1$H NMR (300 MHz, DMSO-$d_6$) δ ppm 8.11-8.29 (m, 1H), 7.91-8.03 (m, 2H), 7.70-7.81 (m, 1H), 7.56-7.67 (m, 2H), 7.29-7.54 (m, 5H), 5.35 and 5.36 (d, 1H), 5.20-5.26 (m, 1H), 5.16 and 5.18 (s, 2H), 4.09-4.22 (m, 1H), 4.06 (q, 2H), 3.43-3.84 (m, 5H), 2.15-2.24 (m, 1H), 1.52-2.14 and 2.32-2.42 (m, 4H), 1.19 (t, 3H);

LC-MS (ESI POS): 451.27 (M+).

Example 13

Preparation of (3R)-3-(2-((2-methoxyethoxy)carbonylamino)-2-phenylacetoxy)-1-(2-oxo-2-phenylethyl)-1-azoniabicyclo[2.2.2]octane bromide (C37)

Scheme 14

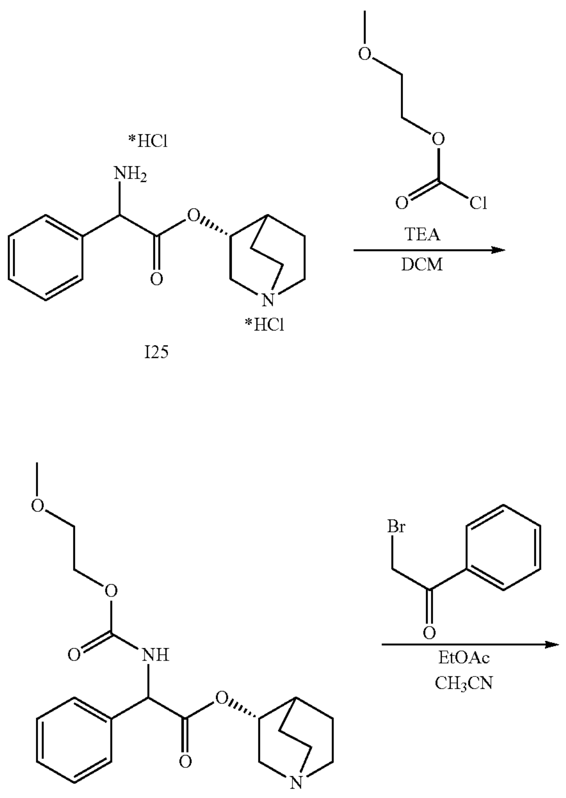

I25

C36

-continued

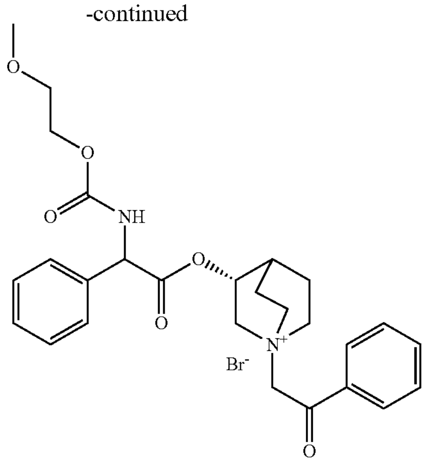

C37

Preparation of (R)-quinuclidin-3-yl 2-((2-methoxyethoxy)-carbonylamino)-2-phenylacetate (C36)

To a suspension of (R)-quinuclidin-3-yl 2-amino-2-phenylacetate dihydrochloride (I25) (150 mg, 0.45 mmol) in DCM (5 ml), was added triethylamine (188 μl, 1.35 mmol) and 2-methoxyethyl carbonochloridate (63 μl, 0.54 mmol). The reaction was stirred at RT for 4 hours, and then the solvent was evaporated. The residue was taken up with EtOAc, and the organic phase was washed with water and brine, dried over $Na_2SO_4$ and evaporated to dryness, obtaining (R)-quinuclidin-3-yl 2-((2-methoxyethoxy)-carbonylamino)-2-phenylacetate (73.0 mg; 45% yield).

Preparation of (3R)-3-(2-((2-methoxyethoxy)carbonylamino)-2-phenylacetoxy)-1-(2-oxo-2-phenylethyl)-1-azoniabicyclo[2.2.2]octane bromide (C37)

To a solution of (R)-quinuclidin-3-yl 2-((2-methoxyethoxy)-carbonylamino)-2-phenylacetate (C36) (73.0 mg, 0.20 mmol) in EtOAc (3 ml) and acetonitrile (1 ml), was added 2-bromo-1-phenylethanone (44.1 mg, 0.22 mmol). The reaction was stirred at RT for 15 hours, and then the solvent was evaporated, and the resulting crude was purified by flash chromatography (DCM/MeOH=95/5 to 93/7). The product was triturated with i-Pr2O to obtain (3R)-3-(2-((2-methoxyethoxy)carbonylamino)-2-phenylacetoxy)-1-(2-oxo-2-phenylethyl)-1-azoniabicyclo[2.2.2]octane bromide (61.3 mg; 54% yield).

$^1$H NMR (300 MHz, DMSO-$d_6$) δ ppm 8.23-8.44 (m, 1H) 7.89-8.08 (m, 2H) 7.69-7.83 (m, 1H) 7.54-7.68 (m, 2H) 7.29-7.52 (m, 5H) 5.36 (dd, 1H) 5.08-5.28 (m, 3H) 4.05-4.21 (m, 3H) 3.44-3.80 (m, 7H) 3.26 (s, 3H) 2.32-2.43 (m, 1H) 1.88-2.12 (m, 3H) 1.69-1.88 (m, 1H);

LC-MS (ESI POS): 481.18 (M+).

Example 14

Preparation of (3R)-3-(2-(cyclohexyloxycarbonylamino)-2-phenylacetoxy)-1-(2-oxo-2-phenylethyl)-1-azoniabicyclo[2.2.2]octane bromide (C39)

Scheme 15

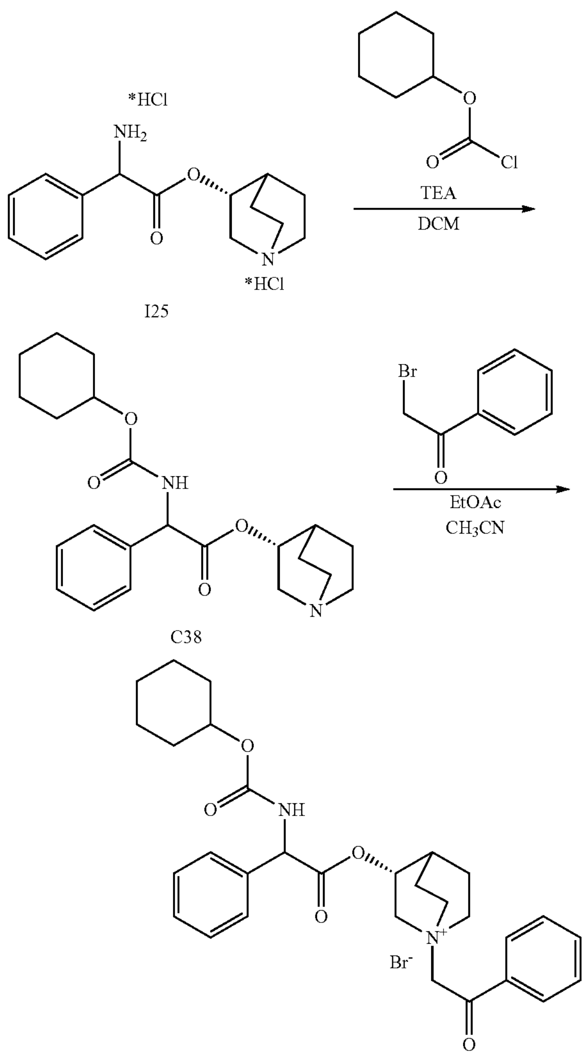

I25

C38

C39

Preparation of (R)-quinuclidin-3-yl 2-(cyclohexyloxycarbonylamino)-2-phenylacetate (C38)

To a suspension of (R)-quinuclidin-3-yl 2-amino-2-phenylacetate dihydrochloride (I25) (150 mg, 0.45 mmol) in DCM (5 ml), were added triethylamine (188 μl, 1.35 mmol) and cyclohexyl carbonochloridate (78 μl, 0.54 mmol). The reaction was stirred at RT for 4 hours, and then the solvent was evaporated. The residue was taken up with EtOAc and washed with water and brine, dried over $Na_2SO_4$ and evaporated to dryness to obtain (R)-quinuclidin-3-yl 2-(cyclohexyloxycarbonylamino)-2-phenylacetate (105 mg; 60% yield).

Preparation of (3R)-3-(2-(cyclohexyloxycarbonylamino)-2-phenylacetoxy)-1-(2-oxo-2-phenylethyl)-1-azoniabicyclo[2.2.2]octane bromide (C39)

To a solution of (R)-quinuclidin-3-yl 2-(cyclohexyloxycarbonylamino)-2-phenylacetate (C38) (105 mg, 0.27 mmol) in EtOAc (3 ml), was added 2-bromo-1-phenylethanone (59.5 mg, 0.30 mmol). The reaction was stirred at RT for 15 hours, and then the solvent was evaporated. The crude was purified by flash chromatography (DCM/MeOH=95/5 to 93/7) to obtain (3R)-3-(2-(cyclohexyloxycarbonylamino)-2-phenylacetoxy)-1-(2-oxo-2-phenylethyl)-1-azoniabicyclo[2.2.2]octane bromide (83.8 mg; 53% yield).

$^1$H NMR (300 MHz, DMSO-$d_6$) δ ppm 8.13 (m, 1H) 7.90-8.04 (m, 2H) 7.69-7.84 (m, 1H) 7.61 (td, 2H) 7.25-7.53 (m, 5H) 5.35 (dd, 1H) 5.05-5.28 (m, 3H) 4.41-4.67 (m, 1H) 3.91-4.23 (m, 1H) 3.49-3.76 (m, 5H) 2.12-2.24 (m, 1H) 1.89-2.12 (m, 3H) 1.57-1.89 (m, 5H) 1.11-1.56 (m, 6H);

LC-MS (ESI POS): 505.19 (M+).

Example 15

Preparation of (3R)-3-(2-(tert-butoxycarbonylamino)-2-p-tolylacetoxy)-1-(2-oxo-2-phenylethyl)-1-azoniabicyclo[2.2.2]octane bromide (C42)

Scheme 16

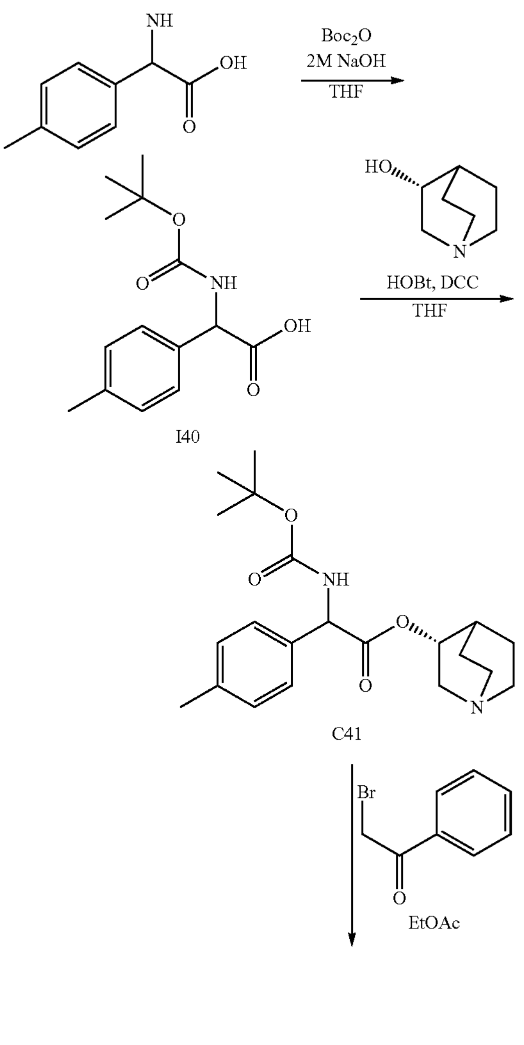

I40

C41

-continued

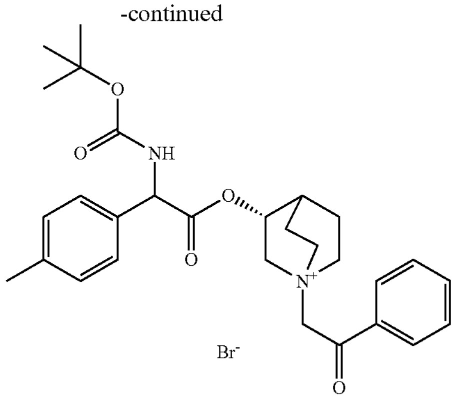

C42

Preparation of 2-(tert-butoxycarbonylamino)-2-p-tolylacetic acid (I40)

To a suspension of 2-amino-2-p-tolylacetic acid (1.00 g, 6.05 mmol) in THF (30 ml) and water (30 ml), was added 2N sodium hydroxide (30.3 ml, 60.5 mmol) and di-tert-butyl dicarbonate (2.64 g, 12.1 mmol). The reaction was stirred at RT for 15 hours, and then THF was evaporated. The remaining aqueous phase was cooled and acidified with 37% HCl until pH 1. The desired compound was extracted with EtOAc, and the organic phase was washed with brine, dried over $Na_2SO_4$ and evaporated to obtain 2-(tert-butoxycarbonylamino)-2-p-tolylacetic acid (1.29 g; 80% yield).

Preparation of (R)-quinuclidin-3-yl 2-(tert-butoxycarbonylamino)-2-p-tolylacetate (C41)

To a solution of 2-(tert-butoxycarbonylamino)-2-p-tolylacetic acid (I40) (1.29 g, 4.86 mmol) in THF (70 ml), are added N,N'-methanediylidenedicyclohexanamine (1.20 g, 5.83 mmol), 1H-benzo[d][1,2,3]triazol-1-ol (0.79 g, 5.83 mmol), and (R)-quinuclidin-3-ol (0.74 g, 5.83 mmol). The reaction was stirred at RT for 15 hours, and then solvent was evaporated. The residue was taken up with DCM, the insoluble solid was filtered off, and the organic solution was washed twice with aq. $Na_2CO_3$ and then brine, dried over $Na_2SO_4$ and evaporated to dryness. The crude was purified by flash chromatography (EtOAc/MeOH=8/2 to 7/3) to obtain (R)-quinuclidin-3-yl 2-(tert-butoxycarbonylamino)-2-p-tolylacetate (1.03 g; 57% yield).

Preparation of (3R)-3-(2-(tert-butoxycarbonylamino)-2-p-tolylacetoxy)-1-(2-oxo-2-phenylethyl)-1-azoniabicyclo[2.2.2]octane bromide (C42)

To a solution of (R)-quinuclidin-3-yl 2-(tert-butoxycarbonylamino)-2-p-tolylacetate (C41) (100 mg, 0.27 mmol) in EtOAc (3 ml), was added 2-bromo-1-phenylethanone (58.5 mg, 0.29 mmol), and the reaction was stirred at RT for 36 hours. The solvent was evaporated, and the residue was first triturated with i-$Pr_2O$ and then purified by flash chromatography (DCM/MeOH=95/5 to 9/1) to obtain (3R)-3-(2-(tert-butoxycarbonylamino)-2-p-tolylacetoxy)-1-(2-oxo-2-phenylethyl)-1-azoniabicyclo[2.2.2]octane bromide (94.4 mg; 62% yield).

$^1H$ NMR (300 MHz, DMSO-$d_6$) δ ppm 7.92-8.06 (m, 2H), 7.70-7.86 (m, 2H), 7.54-7.68 (m, 2H), 7.27-7.42 (m, 2H), 7.12-7.25 (m, 2H), 4.91-5.36 (m, 3H), 3.92-4.21 (m, 1H), 3.44-3.85 (m, 5H), 2.34-2.40 (m, 1H), 2.30 (s, 3H), 1.53-2.22 (m, 4H), 1.41 (s, 9H);

LC-MS (ESI POS): 493.61 (M+).

Example 16

Preparation of (3R)-3-(2-(tert-butoxycarbonylamino)-2-(4-methoxyphenyl)acetoxy)-1-(2-oxo-2-phenylethyl)-1-azoniabicyclo[2.2.2]octane bromide (C45)

Scheme 17

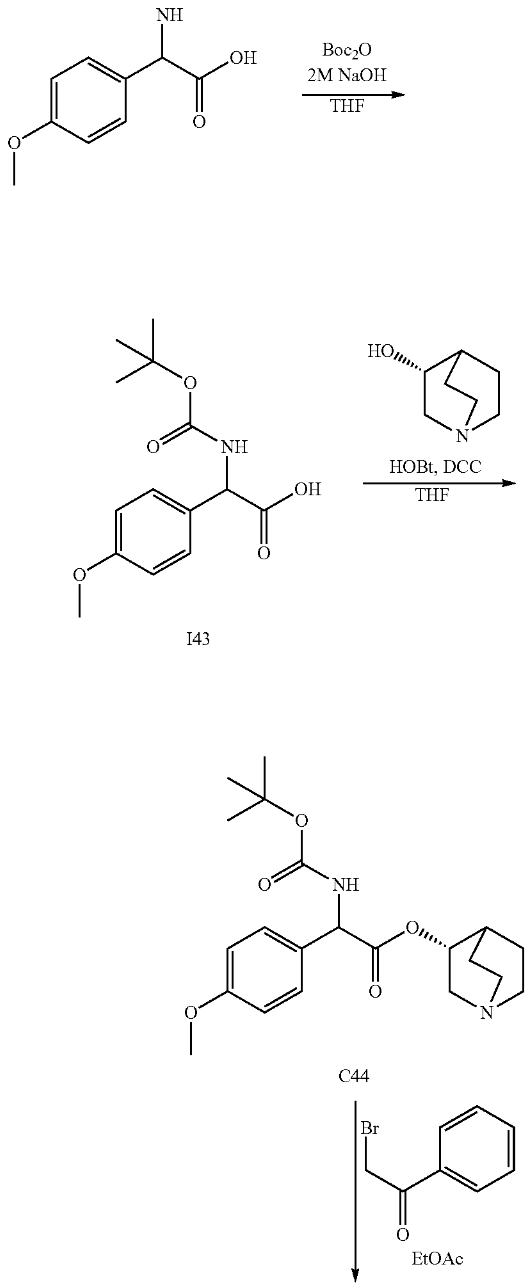

I43

C44

-continued

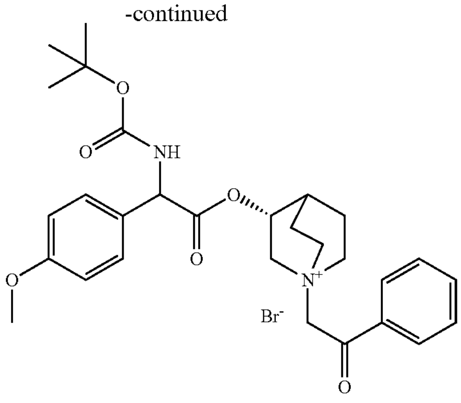

C45

Preparation of 2-(tert-butoxycarbonylamino)-2-(4-methoxyphenyl)acetic acid (I43)

To a suspension of 2-amino-2-(4-methoxyphenyl)acetic acid (360 mg, 1.99 mmol) in THF (30 ml) and water (30 ml), was added 2N sodium hydroxide (20 ml, 40.0 mmol) and di-tert-butyl dicarbonate (867 mg, 3.97 mmol). The reaction was stirred at RT for 15 hours. THF was evaporated, and the remaining aqueous phase was cooled and acidified with 37% HCl until pH 1. The desired compound was extracted with EtOAc, and the organic phase was washed with brine, dried over $Na_2SO_4$ and evaporated to afford 2-(tert-butoxycarbonylamino)-2-(4-methoxyphenyl)acetic acid (430 mg; 77% yield).

Preparation of (R)-quinuclidin-3-yl 2-(tert-butoxycarbonylamino)-2-(4-methoxyphenyl)acetate (C44)

To a solution of 2-(tert-butoxycarbonylamino)-2-(4-methoxyphenyl)acetic acid (I43) (1.39 g, 4.94 mmol) in dry THF (60 ml), were added N,N'-methanediylidenedicyclohexanamine (1.22 g, 5.94 mmol), 1H-benzo[d][1,2,3]triazol-1-ol (802 mg, 5.94 mmol), and (R)-quinuclidin-3-ol (755 mg, 5.94 mmol). The reaction was stirred at RT for 15 hours, and the solvent was evaporated. The residue was taken up with DCM, the insoluble solid was filtered off, and the organic solution was washed twice with aq. $Na_2CO_3$ and then brine, dried over $Na_2SO_4$ and evaporated. The crude was purified by flash chromatography (DCM/MeOH=95/5 to 93/7) to obtain (R)-quinuclidin-3-yl 2-(tert-butoxycarbonylamino)-2-(4-methoxyphenyl)acetate (630 mg; 33% yield).

Preparation of (3R)-3-(2-(tert-butoxycarbonylamino)-2-(4-methoxyphenyl)acetoxy)-1-(2-oxo-2-phenylethyl)-1-azoniabicyclo[2.2.2]octane bromide (C45)

2-Bromo-1-phenylethanone (39.3 mg, 0.20 mmol) is added to a solution of (R)-quinuclidin-3-yl 2-(tert-butoxycarbonylamino)-2-(4-methoxyphenyl)acetate (C44) (70.0 mg, 0.18 mmol) in EtOAc (2 ml) and acetonitrile (2 ml). The reaction was stirred at RT for 15 hours, and then the solvent was evaporated and the resulting colorless oil was triturated first with $i\text{-}Pr_2O$/EtOAc (10/1) and then with $i\text{-}Pr_2O$ to obtain (3R)-3-(2-(tert-butoxycarbonylamino)-2-(4-methoxyphenyl)acetoxy)-1-(2-oxo-2-phenylethyl)-1-azoniabicyclo[2.2.2]octane bromide (60.9 mg; 58% yield).

$^1H$ NMR (300 MHz, DMSO-$d_6$) δ ppm 7.88-8.05 (m, 2H), 7.71-7.84 (m, 2H), 7.54-7.66 (m, 2H), 7.27-7.44 (m, 2H), 6.80-7.02 (m, 2H), 5.18-5.26 (m, 2H), 5.16 (s, 2H), 4.02-4.20 (m, 1H), 3.76 (s, 3H), 3.47-3.72 (m, 5H), 2.33-2.44 (m, 1H), 1.78-2.17 (m, 4H), 1.41 (s, 9H);

LC-MS (ESI POS): 509.15 (M+).

Example 17

Preparation of (3R)-3-(2-(tert-butoxycarbonylamino)-2-(4-chlorophenyl)acetoxy)-1-(2-oxo-2-phenylethyl)-1-azoniabicyclo[2.2.2]octane bromide (C48)

Scheme 18

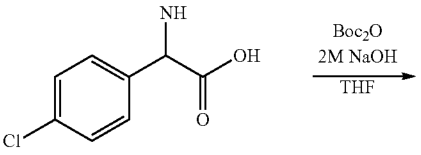

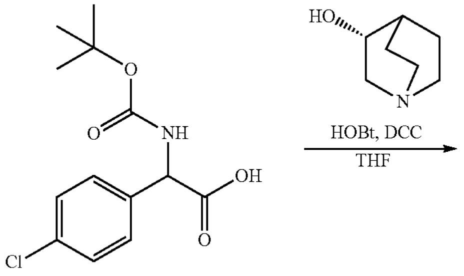

I46

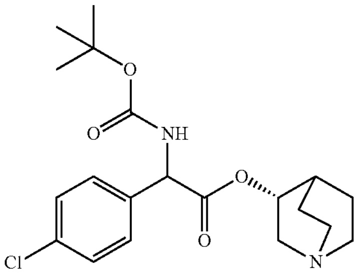

C47

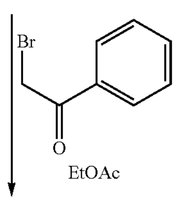

-continued

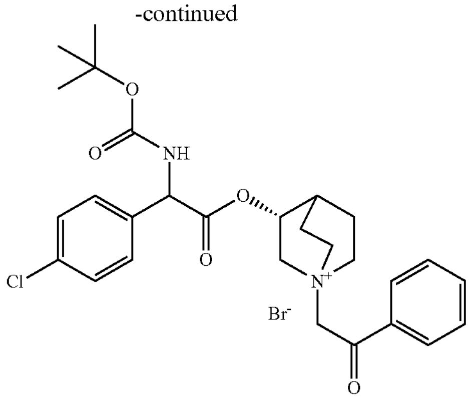

C48

Preparation of 2-(tert-butoxycarbonylamino)-2-(4-chlorophenyl)acetic acid (I46)

To a suspension of 2-amino-2-(4-chlorophenyl)acetic acid (1.50 g, 8.08 mmol) in THF (30 ml) and water (30 ml), were added 2N sodium hydroxide (40.4 ml, 81.0 mmol) and di-tert-butyl dicarbonate (3.53 g, 16.2 mmol). The reaction was stirred at RT for 15 hours. THF was evaporated, and the remaining aqueous phase was cooled and acidified with 37% HCl until pH 1. The desired compound was extracted with EtOAc, and the organic phase was washed with brine, dried over $Na_2SO_4$ and evaporated to afford 2-(tert-butoxycarbonylamino)-2-(4-chlorophenyl)acetic acid (2.17 g; 94% yield).

Preparation of (R)-quinuclidin-3-yl 2-(tert-butoxycarbonylamino)-2-(4-chlorophenyl)acetate (C47)

To a solution of 2-(tert-butoxycarbonylamino)-2-(4-chlorophenyl)acetic acid (I46) (2.17 g, 7.58 mmol) in dry THF (70 ml), were added N,N'-methanediylidenedicyclohexanamine (1.88 g, 9.10 mmol), 1H-benzo[d][1,2,3]triazol-1-ol (1.23 g, 9.10 mmol), and (R)-quinuclidin-3-ol (1.16 g, 9.10 mmol). The reaction was stirred at RT for 15 hours, and the solvent was evaporated. The residue was taken up with DCM, the insoluble solid was filtered off, and the organic solution was washed twice with aq. $Na_2CO_3$ and then brine, dried over $Na_2SO_4$ and evaporated. The crude was purified by flash chromatography (EtOAc/MeOH=8/2 to 85/15) to obtain (R)-quinuclidin-3-yl 2-(tert-butoxycarbonylamino)-2-(4-chlorophenyl)acetate (1.33 g; 44% yield).

Preparation of (3R)-3-(2-(tert-butoxycarbonylamino)-2-(4-chlorophenyl)acetoxy)-1-(2-oxo-2-phenylethyl)-1-azoniabicyclo[2.2.2]octane bromide (C48)

2-Bromo-1-phenylethanone (55.4 mg, 0.28 mmol) was added to a solution of (R)-quinuclidin-3-yl 2-(tert-butoxycarbonylamino)-2-(4-chlorophenyl)acetate (C47) (100 mg, 0.25 mmol) in EtOAc (3 ml). The reaction was stirred at RT for 36 hours, and then a second portion of 2-bromo-1-phenylethanone (50.4 mg, 0.25 mmol) was added, and the reaction was stirred at RT for additional 48 hours. The organic phase was washed with aq. $Na_2CO_3$, dried over $Na_2SO_4$ and evaporated. The crude was dissolved in acetonitrile (3 ml), and 2-bromo-1-phenylethanone (60.0 mg, 0.30 mmol) was added. The reaction was heated under microwave irradiation at 100° C. for 45 minutes. The solvent was evaporated and the crude was purified by flash chromatography (DCM/MeOH=95/5 to 9/1) to obtain (3R)-3-(2-(tert-butoxycarbonylamino)-2-(4-chlorophenyl)acetoxy)-1-(2-oxo-2-phenylethyl)-1-azoniabicyclo[2.2.2]octane bromide (62.5 mg; 42% yield).

$^1$H NMR (300 MHz, DMSO-$d_6$) δ ppm 7.86-8.03 (m, 3H), 7.69-7.82 (m, 1H), 7.55-7.67 (m, 2H), 7.37-7.55 (m, 4H), 5.34 (d, 1H), 5.16-5.25 (m, 1H), 5.05-5.16 (m, 1H), 3.96-4.16 (m, 1H), 3.43-3.81 (m, 5H), 2.32-2.42 (m, 1H), 1.79-2.15 (m, 4H), 1.41 (s, 9H);

LC-MS (ESI POS): 513.16 (M+).

Example 18

Preparation of (3R)-3-(2-(tert-butoxycarbonylamino)-2-(4-fluorophenyl)acetoxy)-1-(2-oxo-2-phenylethyl)-1-azoniabicyclo[2.2.2]octane bromide (C51)

Scheme 19

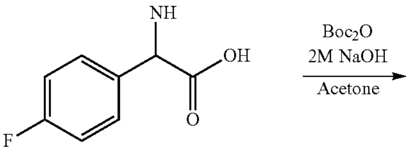

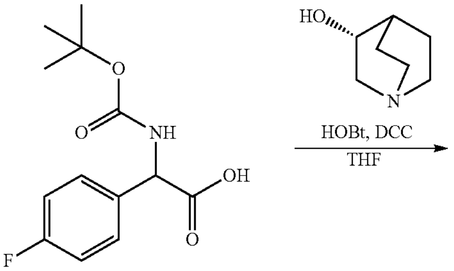

I49

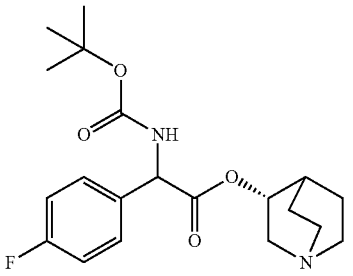

C50

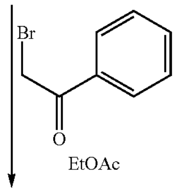

-continued

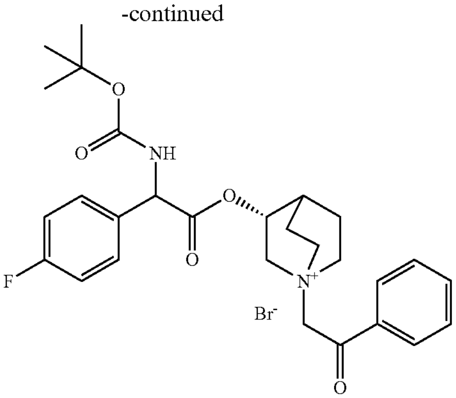

C51

Preparation of 2-(tert-butoxycarbonylamino)-2-(4-fluorophenyl)acetic acid (I49)

To a solution of 2-amino-2-(4-fluorophenyl)acetic acid (1.00 g, 5.91 mmol) in acetone (50 ml) and 2N sodium hydroxide (50 ml, 100 mmol), was added di-tert-butyl dicarbonate (1.29 g, 5.91 mmol), and the reaction was stirred at RT for 3 hours. Acetone was evaporated, the aqueous phase was acidified with 37% HCl until pH 1. The product was extracted with EtOAc, and the organic phase was washed with water and brine, dried over $Na_2SO_4$ and evaporated. The resulting oil was triturated with petroleum ether to give 2-(tert-butoxycarbonylamino)-2-(4-fluorophenyl)acetic acid (725 mg; 45% yield).

Preparation of (R)-quinuclidin-3-yl 2-(tert-butoxycarbonylamino)-2-(4-fluorophenyl)acetate (C50)

To a solution of 2-(tert-butoxycarbonylamino)-2-(4-fluorophenyl)acetic acid (I49) (725 mg, 2.69 mmol) in THF (20 ml), were added N,N'-methanediylidenedicyclohexanamine (667 mg, 3.23 mmol), 1H-benzo[d][1,2,3]triazol-1-ol (437 mg, 3.23 mmol), and (R)-quinuclidin-3-ol (411 mg, 3.23 mmol). The reaction was stirred at RT for 15 hours, and the solvent was evaporated. The residue was taken up with DCM, the insoluble solid was filtered off, and the organic solution was washed twice with aq. $Na_2CO_3$ and then brine, dried over $Na_2SO_4$ and evaporated. The crude was purified by flash chromatography (DCM/MeOH=95/5 to 93/7) to obtain (R)-quinuclidin-3-yl 2-(tert-butoxycarbonylamino)-2-(4-fluorophenyl)acetate (410 mg; 40% yield).

Preparation of (3R)-3-(2-(tert-butoxycarbonylamino)-2-(4-fluorophenyl)acetoxy)-1-(2-oxo-2-phenylethyl)-1-azoniabicyclo[2.2.2]-octane bromide (C51)

2-Bromo-1-phenylethanone (34.7 mg, 0.17 mmol) is added to a solution of (R)-quinuclidin-3-yl 2-(tert-butoxycarbonylamino)-2-(4-fluorophenyl)-acetate (C50) (60.0 mg, 0.16 mmol) in EtOAc (2 ml) and acetonitrile (2 ml). The reaction was stirred at RT for 15 hours, and then the solvent was evaporated. The resulting residue was triturated with i-$Pr_2O$/EtOAc (10/1) and then i-$Pr_2O$ to obtain (3R)-3-(2-(tert-butoxycarbonyl-amino)-2-(4-fluorophenyl)acetoxy)-1-(2-oxo-2-phenylethyl)-1-azoniabicyclo-[2.2.2]octane bromide (46.1 mg; 50% yield).

$^1H$ NMR (300 MHz, DMSO-$d_6$) δ ppm 7.93-8.02 (m, 2H), 7.91 (d, 1H), 7.69-7.80 (m, 1H), 7.57-7.67 (m, 2H), 7.47-7.57 (m, 2H), 7.17-7.31 (m, 2H), 5.33 (d, 1H), 5.17-5.26 (m, 1H), 5.15 (s, 2H), 4.07 (ddd, 1H), 3.44-3.79 (m, 5H), 2.37 (br. s., 1H), 1.74-2.23 (m, 4H), 1.41 (s, 9H);

LC-MS (ESI POS): 497.14 (M+).

Example 19

Preparation of (3R)-3-(2-(tert-butoxycarbonylamino)-2-(3-fluorophenyl)acetoxy)-1-(2-oxo-2-phenylethyl)-1-azoniabicyclo[2.2.2]octane bromide (C54)

Scheme 20

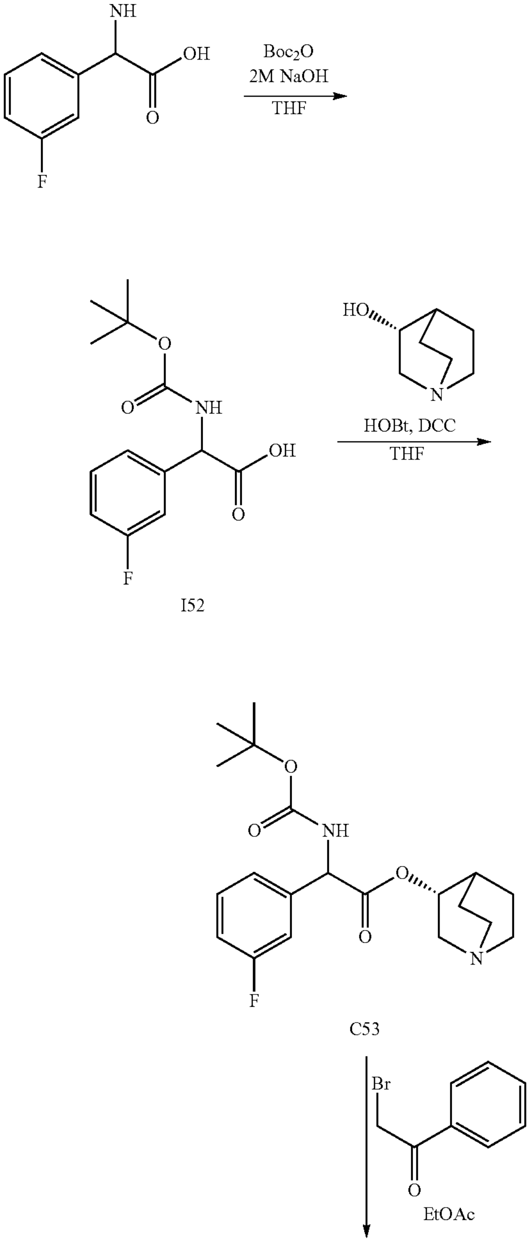

I52

C53

-continued

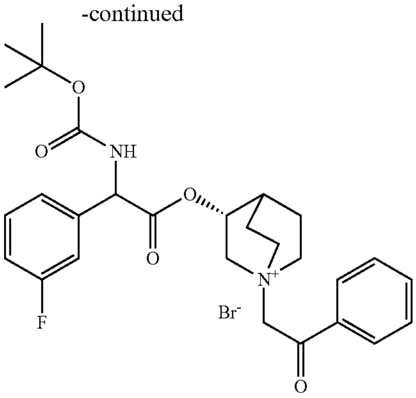

C54

Preparation of 2-(tert-butoxycarbonylamino)-2-(3-fluorophenyl)acetic acid (I52)

To a suspension of 2-amino-2-(3-fluorophenyl)acetic acid (1.00 g, 5.91 mmol) in THF (30 ml) and water (30 ml), were added 2N sodium hydroxide (29.6 ml, 59.1 mmol) and di-tert-butyl dicarbonate (2.58 g, 11.8 mmol), and the reaction was stirred at RT for 15 hours. THF was evaporated, and the aqueous phase was cooled and acidified with 37% HCl until pH 1. The desired compound was extracted with EtOAc, and the organic phase was washed with brine, dried over $Na_2SO_4$ and evaporated to obtain 2-(tert-butoxycarbonylamino)-2-(3-fluorophenyl)acetic acid (1.10 g; 69% yield).

Preparation of (R)-quinuclidin-3-yl 2-(tert-butoxycarbonylamino)-2-(3-fluorophenyl)acetate (C53)

To a solution of 2-(tert-butoxycarbonylamino)-2-(3-fluorophenyl)acetic acid (I52) (1.10 g, 4.09 mmol) in THF (50 ml), were added N,N'-methanediylidenedicyclohexanamine (1.01 g, 4.90 mmol), 1H-benzo[d][1,2,3]triazol-1-ol (0.66 g, 4.90 mmol), and (R)-quinuclidin-3-ol (0.62 g, 4.90 mmol). The reaction was stirred at RT for hours, and the solvent was evaporated. The residue was taken up with DCM, the insoluble solid was filtered off, and the organic solution was washed twice with aq. $Na_2CO_3$ and then brine, dried over $Na_2SO_4$ and evaporated to obtain (R)-quinuclidin-3-yl 2-(tert-butoxycarbonylamino)-2-(3-fluorophenyl)acetate (1.55 g; quantitative yield).

Preparation of (3R)-3-(2-(tert-butoxycarbonylamino)-2-(3-fluorophenyl)acetoxy)-1-(2-oxo-2-phenylethyl)-1-azoniabicyclo[2.2.2]-octane bromide (C54)

2-Bromo-1-phenylethanone (63.1 mg, 0.32 mmol) was added to a solution of (R)-quinuclidin-3-yl 2-(tert-butoxycarbonylamino)-2-(3-fluorophenyl)acetate (C53) (100 mg, 0.26 mmol) in EtOAc (3 ml) and acetonitrile (3 ml). The reaction was stirred at RT for 15 hours, and then the solvent was evaporated. The crude was purified by flash chromatography (DCM/MeOH=94/6) to obtain (3R)-3-(2-(tert-butoxycarbonylamino)-2-(3-fluorophenyl)acetoxy)-1-(2-oxo-2-phenylethyl)-1-azoniabicyclo[2.2.2]octane bromide (70.7 mg; 46% yield).

$^1H$ NMR (300 MHz, DMSO-$d_6$) δ ppm 7.87-8.07 (m, 3H), 7.70-7.83 (m, 1H), 7.55-7.69 (m, 2H), 7.38-7.50 (m, 1H), 7.27-7.38 (m, 2H), 7.08-7.27 (m, 1H), 5.32-5.49 (m, 1H), 5.19-5.27 (m, 1H), 5.09-5.19 (m, 1H), 3.93-4.23 (m, 1H), 3.42-3.90 (m, 5H), 2.15-2.26 and 2.32-2.42 (m, 1H), 1.59-2.13 (m, 4H), 1.41 (s, 9H);

LC-MS (ESI POS): 497.22 (M+).

Example 20

Preparation of (3R)-3-(2-(tert-butoxycarbonylamino)-2-(2-fluorophenyl)acetoxy)-1-(2-oxo-2-phenylethyl)-1-azoniabicyclo[2.2.2]octane bromide (C57)

Scheme 21

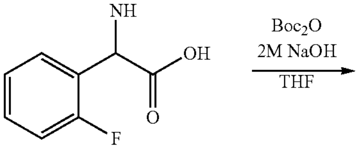

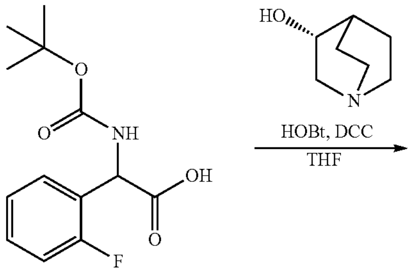

I55

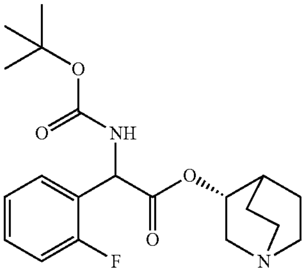

C56

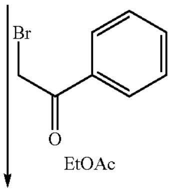

-continued

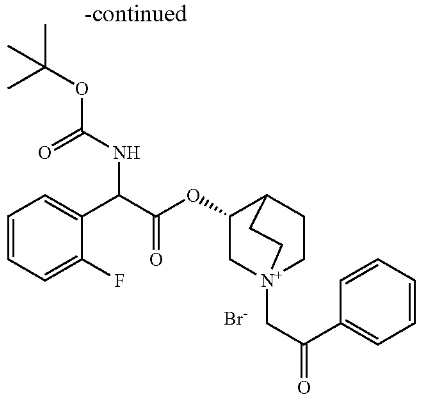

C57

Preparation of 2-(tert-butoxycarbonylamino)-2-(2-fluorophenyl)acetic acid (I55)

To a suspension of 2-amino-2-(2-fluorophenyl)acetic acid (1.00 g, 5.91 mmol) in THF (30 ml) and water (30 ml), were added 2N sodium hydroxide (29.6 ml, 59.1 mmol) and di-tert-butyl dicarbonate (2.58 g, 11.8 mmol). The reaction was stirred at RT for 15 hours. THF was evaporated, and the aqueous phase was cooled to 0° C. and acidified with 37% HCl until pH 1. The desired compound was extracted with EtOAc, and the organic phase was washed with brine, dried over $Na_2SO_4$ and evaporated to obtain 2-(tert-butoxycarbonylamino)-2-(2-fluorophenyl)acetic acid (1.11 g; 70% yield).

Preparation of (R)-quinuclidin-3-yl 2-(tert-butoxycarbonylamino)-2-(2-fluorophenyl)acetate (C56)

To a solution of 2-(tert-butoxycarbonylamino)-2-(2-fluorophenyl)acetic acid (I55) (1.11 g, 4.12 mmol) in THF (50 ml), were added N,N'-methanediylidenedicyclohexanamine (1.02 g, 4.95 mmol), 1H-benzo[d][1,2,3]triazol-1-ol (0.67 g, 4.95 mmol), and (R)-quinuclidin-3-ol (0.63 g, 4.95 mmol). The reaction was stirred at RT for hours, and the solvent was evaporated. The residue was taken up with DCM, the insoluble solid was filtered off, and the organic solution was washed twice with aq. $Na_2CO_3$ and then brine, dried over $Na_2SO_4$ and evaporated to obtain (R)-quinuclidin-3-yl 2-(tert-butoxycarbonylamino)-2-(2-fluorophenyl)acetate (1.56 g; quantitative yield).

Preparation of (3R)-3-(2-(tert-butoxycarbonylamino)-2-(2-fluorophenyl)acetoxy)-1-(2-oxo-2-phenylethyl)-1-azoniabicyclo[2.2.2]octane bromide (C57)

2-Bromo-1-phenylethanone (57.9 mg, 0.29 mmol) was added to a solution of (R)-quinuclidin-3-yl 2-(tert-butoxycarbonylamino)-2-(2-fluorophenyl)acetate (C56) (100 mg, 0.26 mmol) in EtOAc (3 ml) and acetonitrile (3 ml). The reaction was stirred at RT for 15 hours, and then the solvent was evaporated. The crude was purified by flash chromatography (DCM/MeOH=94/6) to obtain (3R)-3-(2-(tert-butoxycarbonylamino)-2-(2-fluorophenyl)acetoxy)-1-(2-oxo-2-phenylethyl)-1-azoniabicyclo[2.2.2]octane bromide (95.1 mg; 62% yield).

$^1H$ NMR (300 MHz, DMSO-$d_6$) δ ppm 7.90-8.10 (m, 3H), 7.70-7.81 (m, 1H), 7.61 (td, 2H), 7.47-7.56 (m, 1H), 7.37-7.47 (m, 1H), 7.15-7.30 (m, 2H), 5.49-5.68 (m, 1H), 5.20-5.37 (m, 1H), 5.04-5.20 (m, 1H), 3.99-4.28 (m, 1H), 3.39-3.89 (m, 5H), 2.32-2.43 (m, 1H), 1.48-2.15 and 2.15-2.25 (m, 4H), 1.41 (s, 9H);

LC-MS (ESI POS): 497.18 (M+).

Example 21

Preparation of 3-(2-(tert-butoxycarbonylamino)-2-phenylacetoxy)-8-methyl-8-(2-oxo-2-phenylethyl)-8-azoniabicyclo[3.2.1]octane bromide (C59)

Scheme 22

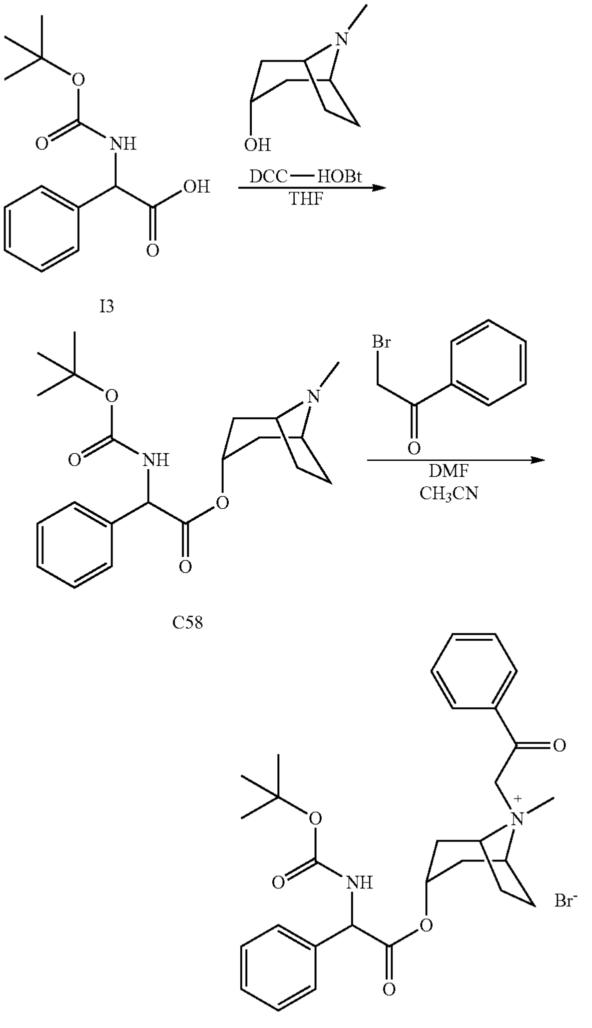

I3

C58

C59

Preparation of 8-methyl-8-azabicyclo[3.2.1]octan-3-yl 2-(tert-butoxycarbonylamino)-2-phenylacetate (C58)

To a solution of 2-(tert-butoxycarbonylamino)-2-phenylacetic acid (400 mg, 1.59 mmol) in THF (20 ml), were added N,N'-methanediylidenedicyclohexanamine (394 mg, 1.91 mmol), 1H-benzo[d][1,2,3]triazol-1-ol (258 mg, 1.91 mmol) and 8-methyl-8-azabicyclo[3.2.1]octan-3-ol (270 mg, 1.91 mmol). The reaction was stirred at RT for 15 hours, and then the solvent was evaporated. The residue was taken up with DCM, the insoluble was filtered off, and the clear solution was washed twice with aq. $Na_2CO_3$ and brine, dried over $Na_2SO_4$ and evaporated to give 8-methyl-8-azabicyclo[3.2.1]octan-3-yl 2-(tert-butoxycarbonylamino)-2-phenylacetate (460 mg; 77% yield). The product was used in the next step without any further purification.

Preparation of 3-(2-(tert-butoxycarbonylamino)-2-phenylacetoxy)-8-methyl-8-(2-oxo-2-phenylethyl)-8-azoniabicyclo[3.2.1]octane bromide (C59)

To a solution of 8-methyl-8-azabicyclo[3.2.1]octan-3-yl 2-(tert-butoxycarbonylamino)-2-phenylacetate (C58) (230 mg, 0.61 mmol) in DMF (15 ml) and acetonitrile (5 ml), was added 2-bromo-1-phenylethanone (134 mg, 0.68 mmol). The reaction was stirred at RT for 15 hours, and then the solvent was evaporated. The crude was first triturated with i-$Pr_2O$ and then purified by flash chromatography (DCM/MeOH=94/6) to obtain 3-(2-(tert-butoxycarbonylamino)-2-phenylacetoxy)-8-methyl-8-(2-oxo-2-phenylethyl)-8-azoniabicyclo[3.2.1]octane bromide (196 mg; 56% yield).

$^1$H NMR (300 MHz, DMSO-$d_6$) δ ppm 7.96-8.05 (m, 2H) 7.88 (d, 1H) 7.67-7.79 (m, 1H) 7.52-7.66 (m, 2H) 7.29-7.51 (m, 5H) 5.29 (d, 1H) 5.09 (s, 2H) 5.00-5.07 (m, 1H) 4.27-4.42 (m, 1H) 4.15-4.27 (m, 1H) 3.26 (s, 3H) 2.57-2.76 (m, 2H) 2.04-2.42 (m, 3H) 1.87-2.02 (m, 1H) 1.48-1.80 (m, 2H) 1.40 (s, 9H);

LC-MS (ESI POS): 493.30 (M+).

Example 22

Preparation of 3-(2-(tert-butoxycarbonylamino)-2-phenylacetoxy)-8,8-dimethyl-8-azoniabicyclo[3.2.1]octane iodide (C60)

Scheme 23

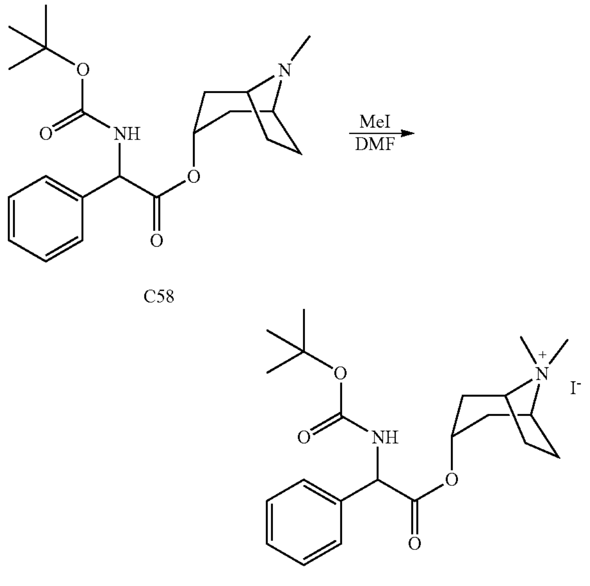

C58

C60

To a solution of 8-methyl-8-azabicyclo[3.2.1]octan-3-yl 2-(tert-butoxycarbonyl-amino)-2-phenylacetate (C58) (230 mg, 0.61 mmol) in DMF (15 ml), was added iodomethane (42.1 µl, 0.68 mmol). The reaction was stirred at RT for 15 hours, and then the solvent was evaporated. The crude was triturated with i-$Pr_2O$ and then purified by flash chromatography (DCM/MeOH=95/5 to 9/1) to obtain 3-(2-(tert-butoxycarbonylamino)-2-phenylacetoxy)-8,8-dimethyl-8-azoniabicyclo[3.2.1]octane iodide (88.2 mg: 28% yield).

$^1$H NMR (300 MHz, DMSO-$d_6$) δ ppm 7.85 (d, 1H) 7.22-7.62 (m, 5H) 5.26 (d, 1H) 4.98 (t, 1H) 3.76-3.87 (m, 1H) 3.65-3.76 (m, 1H) 3.06 (s, 3H) 2.96 (s, 3H) 2.57-2.65 (m, 2H) 1.95-2.23 (m, 3H) 1.87 (d, 1H) 1.46-1.67 (m, 2H) 1.40 (s, 9H);

LC-MS (ESI POS): 389.25 (M+).

Example 23

Preparation of (3R)-3-(2-(tert-butoxycarbonylamino)-2-phenylacetoxy)-1-methyl-1-(2-oxo-2-phenylethyl)pyrrolidinium bromide (C62)

Scheme 24

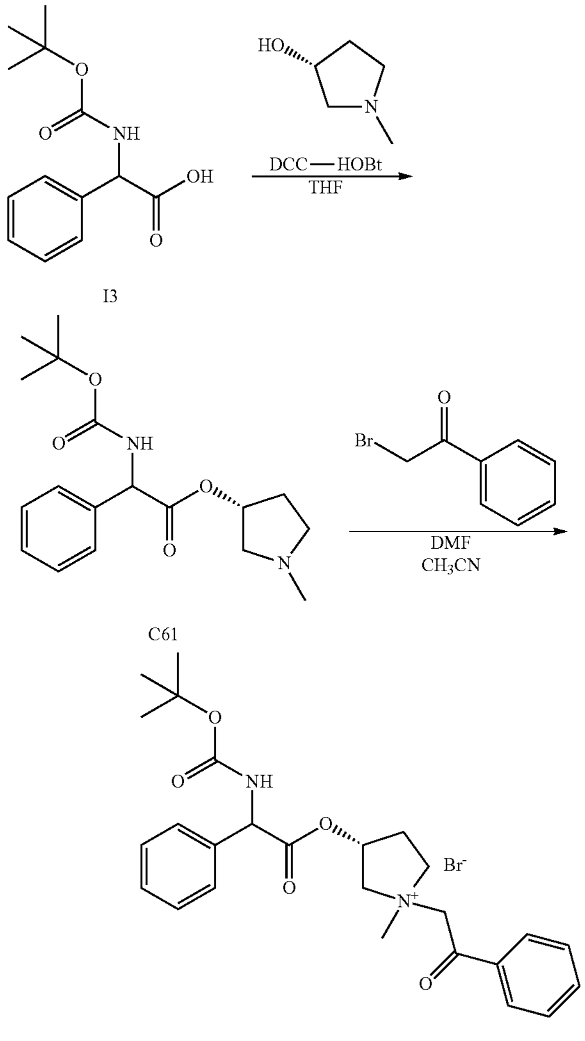

I3

C61

C62

Preparation of (R)-1-methylpyrrolidin-3-yl 2-(tert-butoxycarbonylamino)-2-phenylacetate (C61)

To a solution of 2-(tert-butoxycarbonylamino)-2-phenylacetic acid (I3) (400 mg, 1.59 mmol) in THF (20 ml), were added (R)-1-methylpyrrolidin-3-ol (193 mg, 1.91 mmol), N,N'-methanediylidenedicyclohexanamine (394 mg, 1.91 mmol), and 1H-benzo[d][1,2,3]triazol-1-ol (258 mg, 1.91 mmol). The reaction was stirred at RT for 15, hours, and then the solvent was evaporated. The residue was taken up with DCM, the insoluble was filtered off, and the clear solution was washed twice with aq. $Na_2CO_3$ and brine, dried over $Na_2SO_4$ and evaporated to obtain (R)-1-methylpyrrolidin-3-yl 2-(tert-butoxycarbonylamino)-2-phenylacetate (340 mg; 64% yield).

Preparation of (3R)-3-(2-(tert-butoxycarbonylamino)-2-phenylacetoxy)-1-methyl-1-(2-oxo-2-phenylethyl)pyrrolidinium bromide (C62)

To a solution of (R)-1-methylpyrrolidin-3-yl 2-(tert-butoxycarbonylamino)-2-phenylacetate (C61) (170 mg, 0.51 mmol) in DMF (5 ml) and acetonitrile (3 ml), was added 2-bromo-1-phenylethanone (111 mg, 0.56 mmol). The reaction was stirred at RT for 15 hours, and the solvent was evaporated. The crude was purified by flash chromatography (DCM/MeOH=9/1) to obtain (3R)-3-(2-(tert-butoxycarbonylamino)-2-phenylacetoxy)-1-methyl-1-(2-oxo-2-phenylethyl)pyrrolidinium bromide (152 mg; 56% yield).

$^1$H NMR (300 MHz, DMSO-$d_6$) δ ppm 7.69-8.06 (m, 4H), 7.54-7.69 (m, 2H), 7.20-7.53 (m, 5H), 5.14-5.56 (m, 4H), 3.63-4.26 (m, 4H), 3.11 and 3.30 (s, 3H), 2.56-2.71 (m, 1H), 1.93-2.40 (m, 1H), 1.32 and 1.42 (s, 9H);

LC-MS (ESI POS): 453.28 (M+).

Example 24

Preparation of (3R)-3-(2-(tert-butoxycarbonylamino)-2-phenylacetoxy)-1-methyl-1-(2-oxo-2-(thiophen-2-yl)ethyl)pyrrolidinium bromide (C63)

Scheme 25

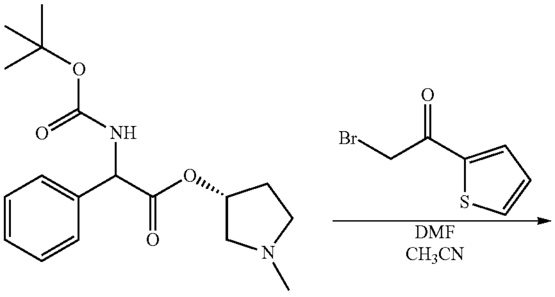

C61

-continued

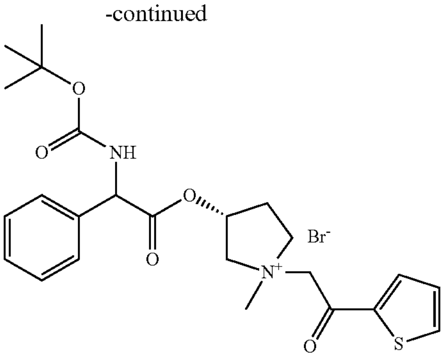

C63

To a solution of (R)-1-methylpyrrolidin-3-yl 2-(tert-butoxycarbonylamino)-2-phenylacetate (C61) (170 mg, 0.51 mmol) in DMF (5 ml) and acetonitrile (3 ml), was added 2-bromo-1-(thiophen-2-yl)ethanone (115 mg, 0.56 mmol) and the reaction was stirred at RT for 15 hours. The solvent was evaporated, and the crude was purified by flash chromatography (DCM/MeOH=9/1) to obtain (3R)-3-(2-(tert-butoxycarbonylamino)-2-phenylacetoxy)-1-methyl-1-(2-oxo-2-(thiophen-2-yl)ethyl)pyrrolidinium bromide (132 mg; 48% yield).

$^1$H NMR (300 MHz, DMSO-$d_6$) δ ppm 8.13-8.32 (m, 1H), 7.98-8.08 (m, 1H), 7.83 and 7.90 (d, 1H), 7.13-7.53 (m, 6H), 5.37-5.56 (m, 1H), 5.03-5.37 (m, 3H), 3.61-4.19 (m, 4H), 3.10 and 3.24 (s, 3H), 2.55-2.71 (m, 1H), 1.91-2.38 (m, 1H), 1.34 and 1.41 (s, 9H);

LC-MS (ESI POS): 459.23 (M+).

Example 25

Preparation of (3R)-1-(2-oxo-2-phenylethyl)-3-(2-phenyl-2-(phenylsulfonamido)acetoxy)-1-azoniabicyclo[2.2.2]octane chloride (C65)

Scheme 26

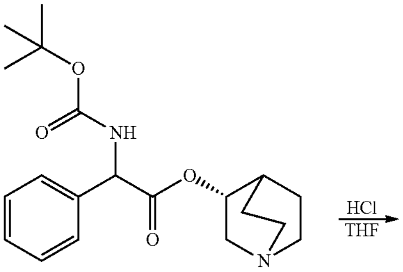

C1

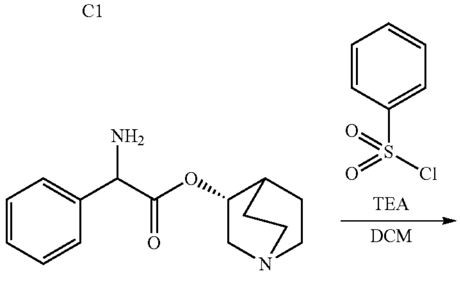

I30

-continued

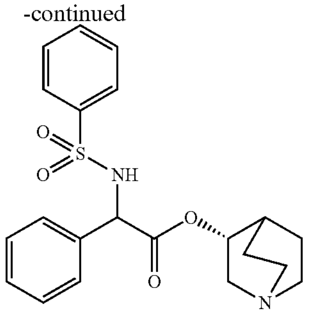

C64

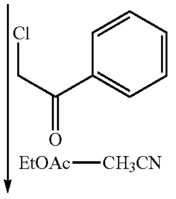

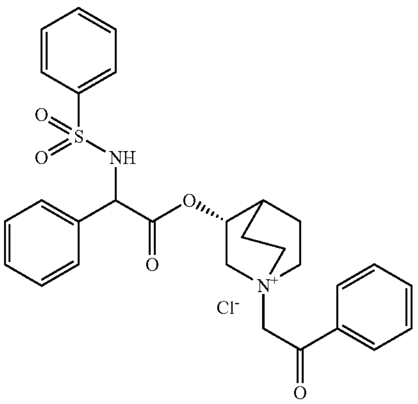

C65

Preparation of (R)-quinuclidin-3-yl 2-amino-2-phenylacetate (I30)

(R)-quinuclidin-3-yl 2-(tert-butoxycarbonylamino)-2-phenylacetate (C1) (5.17 g, 14.3 mmol) was dissolved in THF (47.8 ml) and, while stirring at RT, 37% HCl (4.71 ml, 57.4 mmol) was added dropwise. The reaction was stirred at RT for 15 hours overnight. The solvent was evaporated, and the residue was dissolved in DCM/MeOH (9/1; 10 ml) and about 3 g of SiO2 was added. The solvent was evaporated, and the solid was loaded on a silica gel column and eluted with DCM/MeOH/$NH_4OH$ (9/1/0.1) to obtain (R)-quinuclidin-3-yl 2-amino-2-phenylacetate (2.23 g; 60% yield).

Preparation of (R)-quinuclidin-3-yl 2-phenyl-2-(phenylsulfonamido)acetate (C64)

(R)-quinuclidin-3-yl 2-amino-2-phenylacetate (I30) (100 mg, 0.38 mmol) was dissolved in DCM (4 ml) and TEA (0.11 ml, 0.77 mmol). Benzenesulfonyl chloride (59 μl, 0.46 mmol) was added and the solution was stirred at RT for 1 hour. The volatiles were evaporated and the residue was purified by flash chromatography (DCM/MeOH/$NH_4OH$=95/5/0.3) to obtain (R)-quinuclidin-3-yl 2-phenyl-2-(phenylsulfonamido)acetate (101 mg; 66% yield).

Preparation of (3R)-1-(2-oxo-2-phenylethyl)-3-(2-phenyl-2-(phenylsulfonamido)acetoxy)-1-azoniabicyclo[2.2.2]octane chloride (C65)

To a solution of (R)-quinuclidin-3-yl 2-phenyl-2-(phenylsulfonamido)acetate (C64) (96 mg, 0.24 mmol) in EtOAc (1.6 ml) and acetonitrile (0.8 ml), was added 2-chloro-1-phenylethanone (40.8 mg, 0.26 mmol). The solution was stirred at RT overnight. The solution was concentrated under vacuum and the crude was purified by flash chromatography (DCM/MeOH=95/5 to 9/1) to obtain (3R)-1-(2-oxo-2-phenylethyl)-3-(2-phenyl-2-(phenylsulfonamido)acetoxy)-1-azoniabicyclo[2.2.2]octane chloride (99 mg; 74% yield).

$^1H$ NMR (300 MHz, DMSO-$d_6$) δ ppm 9.06 (br. s., 1H) 7.94-8.04 (m, 2H) 7.71-7.83 (m, 3H) 7.45-7.66 (m, 5H) 7.24-7.41 (m, 5H) 5.26 (d, 1H) 5.22 (d, 1H) 5.13-5.21 (m, 1H) 4.95-5.11 (m, 1H) 3.94-4.17 (m, 1H) 3.47-3.79 (m, 5H) 2.10-2.26 (m, 1H) 1.69-2.08 (m, 4H);

LC-MS (ESI POS): 519.27 (M+).

Example 26

Preparation of (3R)-1-(2-oxo-2-(thiazol-2-yl)ethyl)-3-(2-phenyl-2-(phenylsulfonamido)acetoxy)-1-azoniabicyclo[2.2.2]octane 2,2,2-trifluoroacetate (C66)

Scheme 27

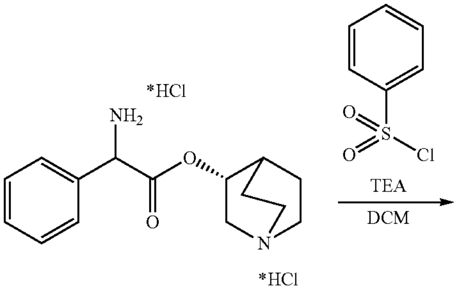

I25

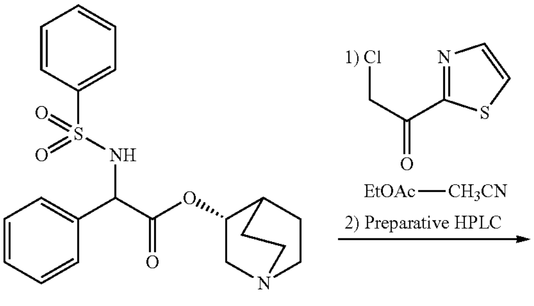

C64

-continued

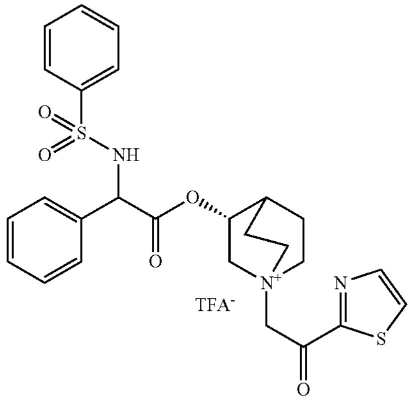

C66

Preparation of (R)-quinuclidin-3-yl 2-phenyl-2-(phenylsulfonamido)acetate (C64)

To a suspension of (R)-quinuclidin-3-yl 2-amino-2-phenylacetate dihydrochloride (I25) (0.67 g, 2.01 mmol) in DCM (25 ml), were sequentially added triethylamine (0.84 ml, 6.04 mmol) and benzenesulfonyl chloride (0.31 ml, 2.42 mmol). The reaction was stirred at RT for 4 hours, and then the solvent was evaporated. The residue was taken up with EtOAc, and washed with water and brine, dried over $Na_2SO_4$ and evaporated to obtain (R)-quinuclidin-3-yl 2-phenyl-2-(phenylsulfonamido)acetate (370 mg; 46% yield).

Preparation of (3R)-1-(2-oxo-2-(thiazol-2-yl)ethyl)-3-(2-phenyl-2-(phenylsulfonamido)acetoxy)-1-azoniabicyclo[2.2.2]octane 2,2,2-trifluoroacetate (C66)

To a solution of (R)-quinuclidin-3-yl 2-phenyl-2-(phenylsulfonamido)acetate (C64) (90.0 mg, 0.22 mmol) in EtOAc (2 ml) and acetonitrile (5 ml), was added 2-bromo-1-(thiazol-2-yl)ethanone (50.9 mg, 0.25 mmol). The reaction was stirred at RT for 39 hours, and then a second portion of 2-bromo-1-(thiazol-2-yl)ethanone (46.3 mg, 0.22 mmol) was added and the reaction is stirred at 60° C. for 15 hours. The solvent was removed under reduced pressure, and the resulting solid is first purified by flash chromatography (Hexane/EtOAc=9/1) and then by preparative HPLC to obtain (3R)-1-(2-oxo-2-(thiazol-2-yl)ethyl)-3-(2-phenyl-2-(phenylsulfonamido)acetoxy)-1-azoniabicyclo[2.2.2]octane 2,2,2-trifluoroacetate (13.6 mg; 10% yield).

$^1H$ NMR (300 MHz, DMSO-$d_6$) δ ppm 8.99 (d, 1H) 8.39 (t, 1H) 8.24 (d, 1H) 7.71-7.83 (m, 2H) 7.44-7.64 (m, 3H) 7.22-7.40 (m, 5H) 5.10-5.22 (m, 3H) 4.94-5.10 (m, 1H) 3.97-4.14 (m, 1H) 3.53-3.76 (m, 5H) 2.12-2.23 (m, 1H) 1.47-2.11 (m, 4H);

LC-MS (ESI POS): 526.13 (M+).

Example 27

Preparation of (3R)-1-(2-oxo-2-(thiophen-2-yl)ethyl)-3-(2-phenyl-2-(phenylsulfonamido)acetoxy)-1-azoniabicyclo[2.2.2]octane 2,2,2-trifluoroacetate (C67)

Scheme 28

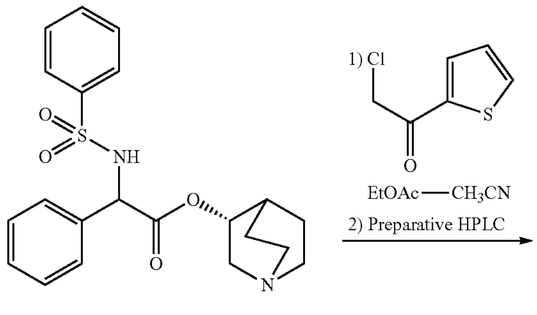

C64

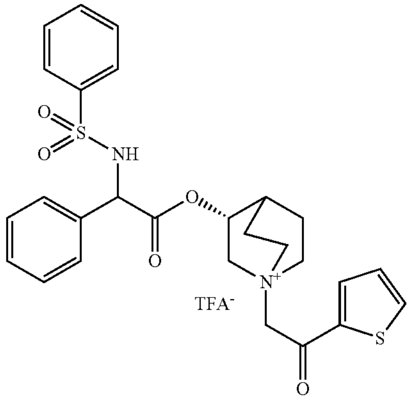

C67

To a solution of (R)-quinuclidin-3-yl 2-phenyl-2-(phenylsulfonamido)acetate (C64) (90.0 mg, 0.22 mmol) in EtOAc (2 ml) and acetonitrile (5 ml), was added 2-chloro-1-(thiophen-2-yl)ethanone (39.7 mg, 0.25 mmol), and the reaction was stirred at RT for hours. Then 2-chloro-1-(thiophen-2-yl)ethanone (36.1 mg, 0.22 mmol) was added again, and the reaction was heated at 60° C. for 15 hours. The solvent was removed, and the crude was purified by flash chromatography (Hexane/EtOAc=9/1) and then by preparative HPLC to obtain (3R)-1-(2-oxo-2-(thiophen-2-yl)ethyl)-3-(2-phenyl-2-(phenylsulfonamido)acetoxy)-1-azoniabicyclo[2.2.2]octane 2,2,2-trifluoroacetate (11.9 mg; 8% yield).

$^1H$ NMR (300 MHz, DMSO-$d_6$) δ ppm 8.99 (d, 1H), 8.20 and 8.21 (dd, 1H), 8.05 and 8.07 (dd, 1H), 7.70-7.85 (m, 2H), 7.43-7.66 (m, 3H), 7.22-7.39 (m, 6H), 5.12-5.21 (m, 1H), 5.04-5.09 (m, 1H), 4.99 and 5.02 (s, 2H), 3.93-4.13 (m, 1H), 3.29-3.56 (m, 5H), 2.11-2.23 (m, 1H), 1.44-2.10 (m, 4H);

LC-MS (ESI POS): 525.11 (M+).

Example 28

Preparation of (3R)-3-(2-(4-methoxyphenylsulfonamido)-2-phenylacetoxy)-1-(2-oxo-2-phenylethyl)-1-azoniabicyclo[2.2.2]octane bromide (C69)

Scheme 29

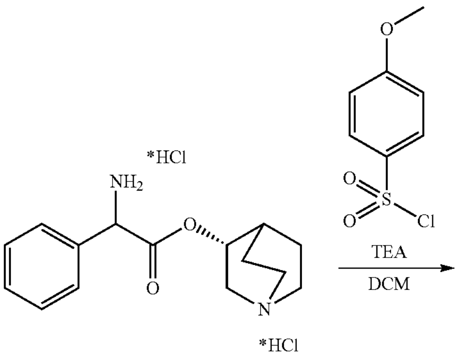

I25

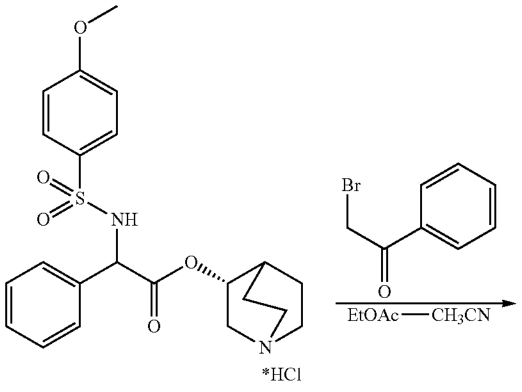

C68

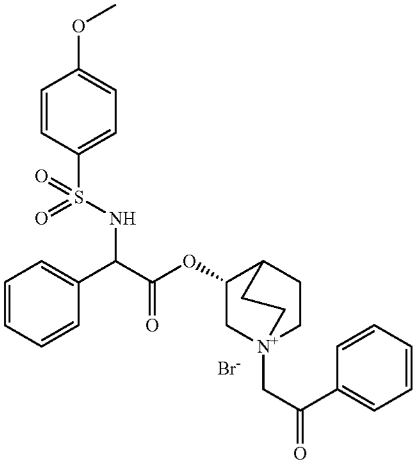

C69

Preparation of (R)-quinuclidin-3-yl 2-(4-methoxyphenylsulfonamido)-2-phenylacetate hydrochloride (C68)

(R)-quinuclidin-3-yl 2-amino-2-phenylacetate dihydrochloride (I25) (150 mg, 0.45 mmol) was suspended in DCM (6 ml) and treated with triethylamine (99 μl, 1.35 mmol). Then 4-methoxybenzene-1-sulfonyl chloride (112 mg, 0.54 mmol) was added, and the reaction was stirred at RT for 3 hours. Solvent was evaporated, and the crude was dissolved in EtOAc and washed with water and brine. The organic phase was dried over $Na_2SO_4$, filtered and evaporated. The crude was triturated with $Et_2O$ to obtain (R)-quinuclidin-3-yl 2-(4-methoxyphenylsulfonamido)-2-phenylacetate hydrochloride (105 mg; 50% yield).

Preparation of (3R)-3-(2-(4-methoxyphenylsulfonamido)-2-phenylacetoxy)-1-(2-oxo-2-phenylethyl)-1-azoniabicyclo[2.2.2]octane bromide (C69)

(R)-quinuclidin-3-yl 2-(4-methoxyphenylsulfonamido)-2-phenylacetate hydrochloride (C68) (96 mg, 0.22 mmol) was dissolved in DCM and washed with 1M $K_2CO_3$. The organic phase was dried over $Na_2SO_4$, filtered and evaporated. The resulting solid was dissolved in EtOAc (2 ml) and 2-bromo-1-phenylethanone (49.2 mg, 0.25 mmol) was added. The reaction was stirred at RT for 3 hours, and then it was washed with aq. $K_2CO_3$, dried over $Na_2SO_4$, filtered and evaporated to obtain (3R)-3-(2-(4-methoxyphenylsulfonamido)-2-phenylacetoxy)-1-(2-oxo-2-phenylethyl)-1-azoniabicyclo[2.2.2]octane bromide (75 mg; 53% yield).

$^1H$ NMR (300 MHz, DMSO-$d_6$) δ ppm 8.84 (d, 1H), 7.88-8.04 (m, 2H), 7.66-7.82 (m, 3H), 7.53-7.66 (m, 2H), 7.25-7.44 (m, 5H), 6.97-7.11 (m, 2H), 5.12-5.19 (m, 1H), 4.95-5.12 (m, 2H), 3.96-4.15 (m, 1H), 3.81 (s, 3H), 3.38-3.76 (m, 5H), 2.13-2.24 (m, 1H), 1.74-2.13 (m, 4H);

LC-MS (ESI POS): 549.19 (M+).

Example 29

Preparation of (3R)-3-(2-(4-chlorophenylsulfonamido)-2-phenylacetoxy)-1-(2-oxo-2-phenylethyl)-1-azoniabicyclo[2.2.2]octane bromide (C71)

Scheme 30

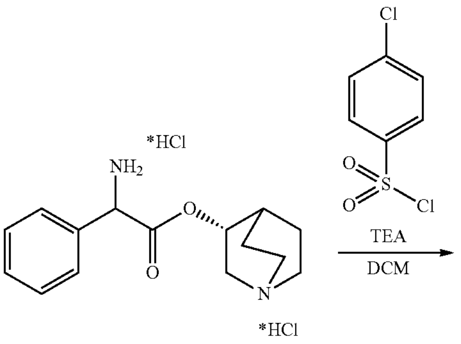

I25

-continued

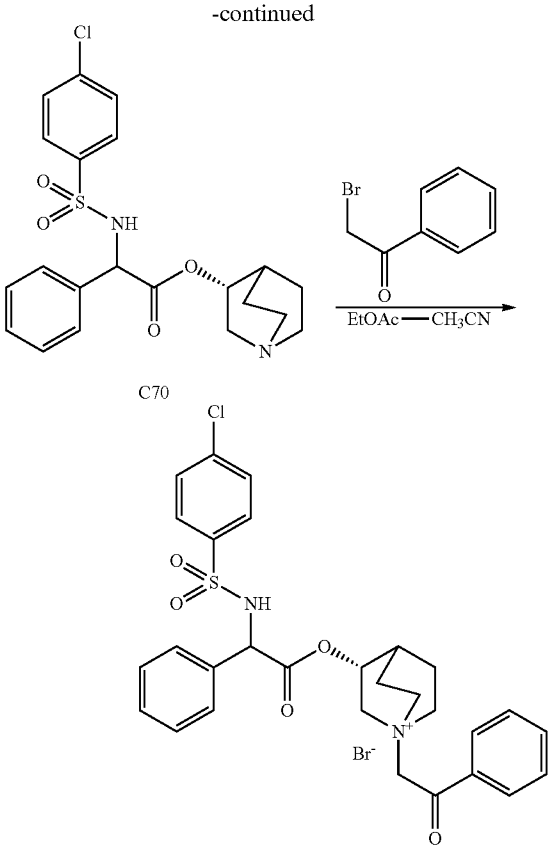

C70

C71

Preparation of (R)-quinuclidin-3-yl 2-(4-chlorophenylsulfonamido)-2-phenylacetate (C70)

To a solution of (R)-quinuclidin-3-yl 2-amino-2-phenylacetate dihydrochloride (I25) (150 mg, 0.45 mmol) in DCM (5 ml) and triethylamine (190 ul, 1.35 mmol), was added 4-chlorobenzene-1-sulfonyl chloride (114 mg, 0.54 mmol). The reaction was stirred at RT for 3 hours, and then the solvent was evaporated. The crude was taken up with EtOAc and washed with water, brine and then with $K_2CO_3$. The organic phase was dried over $Na_2SO_4$, filtered and evaporated to dryness to obtain (R)-quinuclidin-3-yl 2-(4-chlorophenylsulfonamido)-2-phenylacetate (62 mg; 32% yield), which was used as such in the next step.

Preparation of (3R)-3-(2-(4-chlorophenylsulfonamido)-2-phenylacetoxy)-1-(2-oxo-2-phenylethyl)-1-azoniabicyclo[2.2.2]octane bromide (C71)

To a solution of (R)-quinuclidin-3-yl 2-(4-chlorophenylsulfonamido)-2-phenylacetate (C70) (62 mg, 0.14 mmol) in EtOAc (2.5 ml), was added 2-bromo-1-phenylethanone (31.2 mg, 0.16 mmol), and the reaction was stirred at RT for 3 hours. Then the solvent was evaporated, and the crude was triturated with $Et_2O$ to obtain (3R)-3-(2-(4-chlorophenylsulfonamido)-2-phenylacetoxy)-1-(2-oxo-2-phenylethyl)-1-azoniabicyclo[2.2.2]octane bromide (38 mg; 42% yield).

$^1H$ NMR (300 MHz, DMSO-$d_6$) δ ppm 9.11 (d, 1H), 7.88-8.07 (m, 2H), 7.69-7.85 (m, 3H), 7.51-7.69 (m, 4H), 7.20-7.44 (m, 5H), 5.17-5.26 (m, 1H), 4.92-5.17 (m, 2H), 3.95-4.19 (m, 1H), 3.39-3.79 (m, 5H), 2.15-2.25 (m, 1H), 1.76-2.15 (m, 4H);

LC-MS (ESI POS): 553.13 (M+).

Example 30

Preparation of (3R)-3-(2-(3,4-difluorophenylsulfonamido)-2-phenylacetoxy)-1-(2-oxo-2-phenylethyl)-1-azoniabicyclo[2.2.2]octane 2,2,2-trifluoroacetate (C73)

Scheme 31

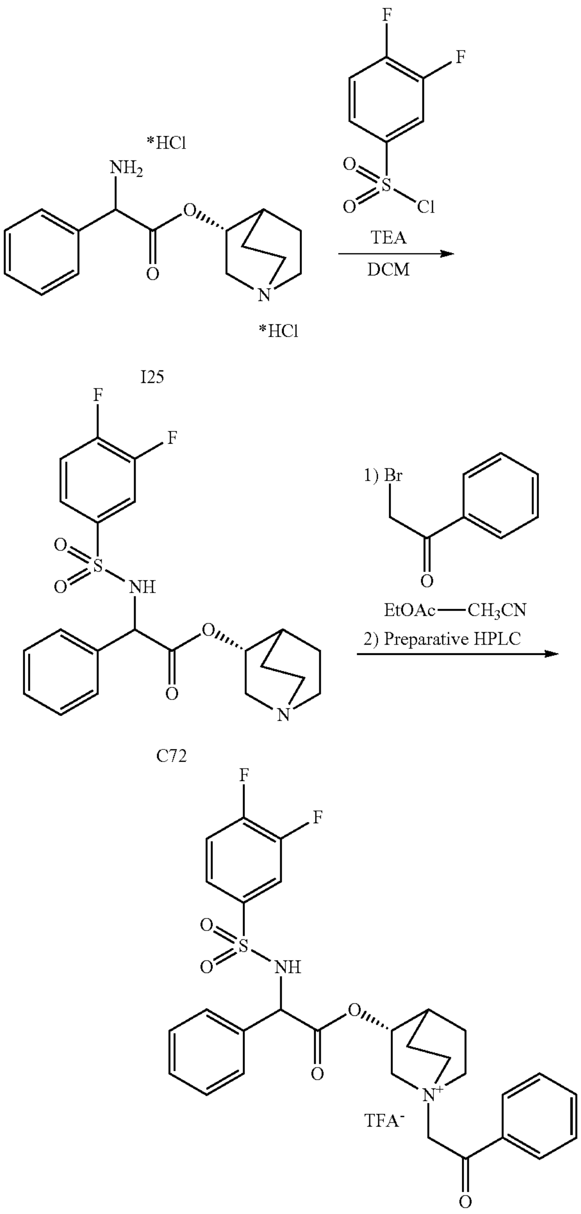

I25

C72

C73

Preparation of (R)-quinuclidin-3-yl 2-(3,4-difluorophenylsulfonamido)-2-phenylacetate (C72)

(R)-quinuclidin-3-yl 2-amino-2-phenylacetate dihydrochloride (I25) (110 mg, 0.33 mmol) was suspended in DCM (4 ml), and triethylamine (121 μl, 1.65 mmol) was added obtaining a solution. 3,4-difluorobenzene-1-sulfonyl chloride (53.1 μl, 0.40 mmol) was added, and the reaction was stirred at RT for 3 hours. The reaction was diluted with DCM and washed with water and brine. The organic phase was dried over $Na_2SO_4$, filtered and evaporated to dryness. The residue was triturated with $Et_2O$ to obtain (R)-quinuclidin-3-yl 2-(3,4-difluorophenylsulfonamido)-2-phenylacetate (40 mg; 28% yield), which was used as such in the next step.

Preparation of (3R)-3-(2-(3,4-difluorophenylsulfonamido)-2-phenylacetoxy)-1-(2-oxo-2-phenylethyl)-1-azoniabicyclo[2.2.2]octane 2,2,2-trifluoroacetate (C73)

To a solution of (R)-quinuclidin-3-yl 2-(3,4-difluorophenylsulfonamido)-2-phenylacetate (C72) (40 mg, 0.09 mmol) in EtOAc (3 ml), was added 2-bromo-1-phenylethanone (20.1 mg, 0.10 mmol), and reaction was stirred at RT for 2 hours. Then the solvent was evaporated, and the crude was first triturated with petroleum ether and then purified by preparative HPLC to obtain (3R)-3-(2-(3,4-difluorophenylsulfonamido)-2-phenylacetoxy)-1-(2-oxo-2-phenylethyl)-1-azoniabicyclo[2.2.2]octane 2,2,2-trifluoroacetate (13 mg; 21% yield).

$^1H$ NMR (300 MHz, Acetone) δ ppm 8.89 and 8.96 (d, 1H), 8.00-8.16 (m, 2H), 7.18-7.91 (m, 11H), 5.52 and 5.58 (d, 1H), 5.44 and 5.51 (d, 1H), 5.28 and 5.35 (d, 1H), 5.18-5.29 (m, 1H), 4.29-4.49 (m, 2H), 3.75-4.28 (m, 4H), 2.39-2.53 (m, 1H), 2.11-2.36 (m, 3H), 1.69-2.03 (m, 1H);

LC-MS (ESI POS): 555.12 (M+).

Example 31

Preparation of (3R)-3-(2-(2,4-dimethylthiazole-5-sulfonamido)-2-phenylacetoxy)-1-(2-oxo-2-phenylethyl)-1-azoniabicyclo[2.2.2]octane 2,2,2-trifluoroacetate (C75)

Scheme 32

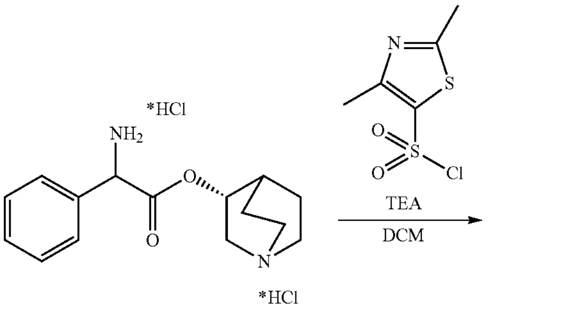

I25

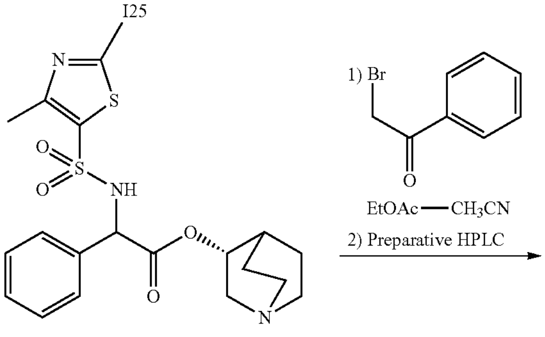

C74

-continued

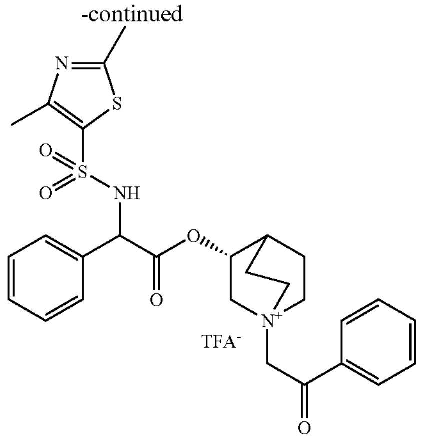

C75

Preparation of (R)-quinuclidin-3-yl 2-(2,4-dimethylthiazole-5-sulfonamido)-2-phenylacetate (C74)

(R)-quinuclidin-3-yl 2-amino-2-phenylacetate dihydrochloride (I25) (116 mg, 0.35 mmol) was suspended in DCM (6 ml), and triethylamine (102 μl, 1.39 mmol) was added obtaining a clear solution. 2,4-Dimethylthiazole-5-sulfonyl chloride (88.0 mg, 0.42 mmol) was added, and the reaction was stirred at RT for 3 hours. The reaction was diluted with DCM and washed with water and brine. The organic phase was dried with $Na_2SO_4$, filtered and evaporated to dryness. The crude was purified by flash chromatography (DCM/MeOH=85/15) to obtain (R)-quinuclidin-3-yl 2-(2,4-dimethylthiazole-5-sulfonamido)-2-phenylacetate (67 mg; 44.2% yield).

Preparation of (3R)-3-(2-(2,4-dimethylthiazole-5-sulfonamido)-2-phenylacetoxy)-1-(2-oxo-2-phenylethyl)-1-azoniabicyclo[2.2.2]octane 2,2,2-trifluoroacetate (C75)

To a solution of (R)-quinuclidin-3-yl 2-(2,4-dimethylthiazole-5-sulfonamido)-2-phenylacetate (C74) (67.0 mg, 0.15 mmol) in EtOAc (2 ml), was added 2-bromo-1-phenylethanone (33.7 mg, 0.17 mmol). The reaction was stirred at RT for 2 hours. The solvent was evaporated, and the crude was purified by preparative HPLC obtaining (3R)-3-(2-(2,4-dimethylthiazole-5-sulfonamido)-2-phenylacetoxy)-1-(2-oxo-2-phenylethyl)-1-azoniabicyclo[2.2.2]octane 2,2,2-trifluoroacetate (18 mg; 18% yield).

$^1H$ NMR (300 MHz, DMSO-$d_6$) δ ppm 9.43 and 9.44 (d, 1H), 7.89-8.05 (m, 2H), 7.70-7.82 (m, 1H), 7.56-7.69 (m, 2H), 7.24-7.46 (m, 5H), 5.15-5.26 (m, 2H), 5.13 (s, 2H), 3.94-4.21 (m, 1H), 3.43-3.62 (m, 5H), 2.55 and 2.58 (s, 3H), 2.39 and 2.42 (s, 3H), 2.06-2.20 and 2.20-2.30 (m, 1H), 1.47-2.05 (m, 4H);

LC-MS (ESI POS): 553.13 (M+).

Example 32

Preparation of (3R)-3-(2-(methylsulfonamido)-2-phenylacetoxy)-1-(2-oxo-2-phenylethyl)-1-azoniabicyclo[2.2.2]octane bromide (C77)

Scheme 33

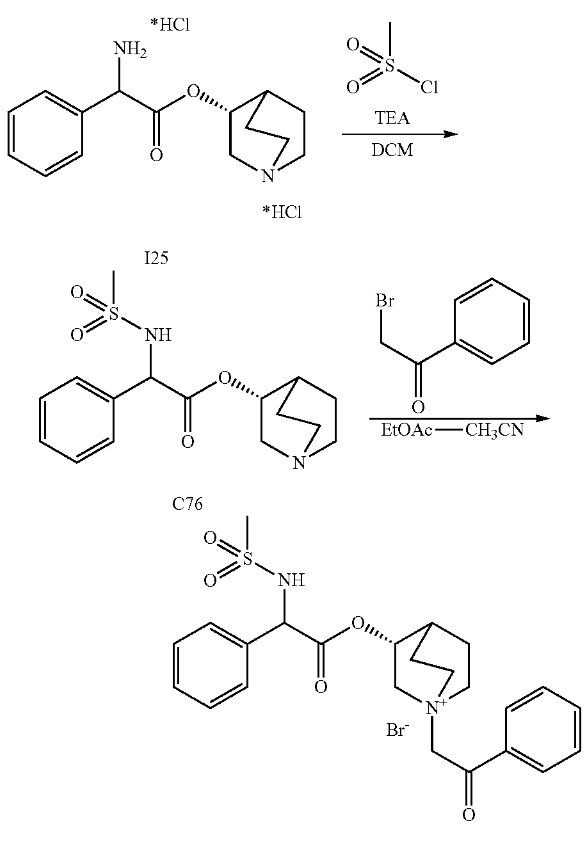

I25

C76

C77

Preparation of (R)-quinuclidin-3-yl 2-(methylsulfonamido)-2-phenylacetate (C76)

To a suspension of (R)-quinuclidin-3-yl 2-amino-2-phenylacetate dihydrochloride (I25) (120 mg, 0.36 mmol) in DCM (6 ml), were sequentially added triethylamine (79 μl, 1.08 mmol) and methanesulfonyl chloride (33.4 μl, 0.43 mmol). The reaction was stirred at RT for 3 hours, and then the volatiles were evaporated. The crude was taken up with EtOAc and washed with water and brine. The organic layer was dried over $Na_2SO_4$, filtered and evaporated to dryness. The crude was triturated with $Et_2O$ to obtain (R)-quinuclidin-3-yl 2-(methylsulfonamido)-2-phenylacetate (38.9 mg; 32% yield).

Preparation of (3R)-3-(2-(methylsulfonamido)-2-phenylacetoxy)-1-(2-oxo-2-phenylethyl)-1-azoniabicyclo[2.2.2]octane bromide (C77)

To a solution of (R)-quinuclidin-3-yl 2-(methylsulfonamido)-2-phenylacetate (C76) (38.9 mg, 0.11 mmol) in EtOAc (1 ml) and acetonitrile (0.5 ml), was added 2-bromo-1-phenylethanone (25.2 mg, 0.13 mmol). The mixture was stirred at RT for 2 hours, and then the solvent was evaporated. The crude was triturated with $Et_2O$ to obtain (3R)-3-(2-(methylsulfonamido)-2-phenylacetoxy)-1-(2-oxo-2-phenylethyl)-1-azoniabicyclo[2.2.2]octane bromide (40 mg; 64.7% yield).

$^1$H NMR (300 MHz, DMSO-$d_6$) δ ppm 8.37 (d, 1H), 7.90-8.05 (m, 2H), 7.69-7.83 (m, 1H), 7.55-7.67 (m, 2H), 7.29-7.55 (m, 5H), 5.27-5.34 (m, 1H), 5.20-5.27 (m, 1H), 5.10-5.20 (m, 2H), 4.00-4.23 (m, 1H), 3.46-3.81 (m, 5H), 2.89 and 2.93 (s, 3H), 2.22 and 2.39 (m, 1H), 1.50-2.15 (m, 4H);

LC-MS (ESI POS): 457.17 (M+).

Example 33

Preparation of (3R)-1-(2-oxo-2-phenylethyl)-3-(2-phenyl-2-(2,2,2-trifluoroethylsulfonamido)acetoxy)-1-azoniabicyclo[2.2.2]octane bromide (C79)

Scheme 34

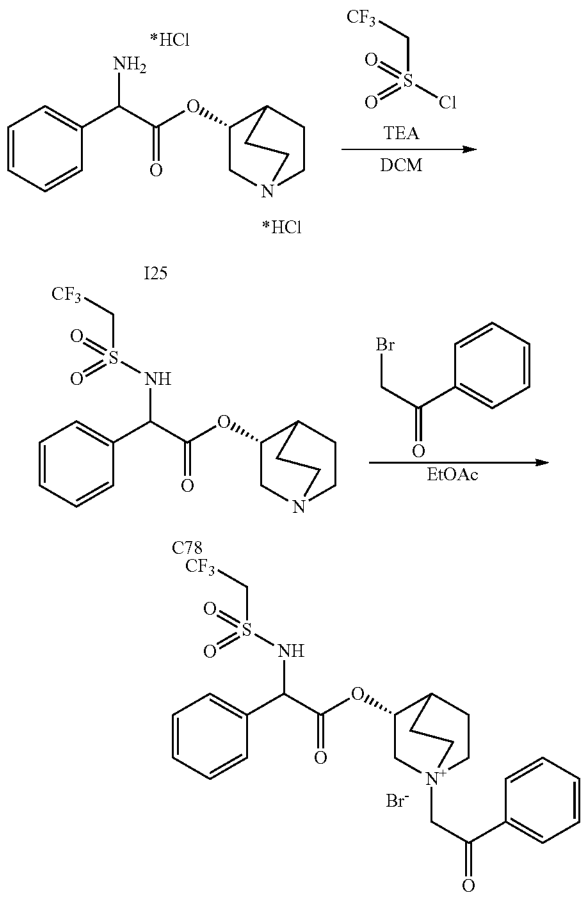

I25

C78

C79

Preparation of (R)-quinuclidin-3-yl 2-phenyl-2-(2,2,2-trifluoroethylsulfonamido)acetate (C78)

To a solution of (R)-quinuclidin-3-yl 2-amino-2-phenylacetate dihydrochloride (I25) (120 mg, 0.36 mmol) in DCM (4 ml) and triethylamine (105 μl, 1.44 mmol), was added 2,2,2-trifluoroethanesulfonyl chloride (47.5 μl, 0.43 mmol). The reaction was stirred at RT for 3 hours, and then it was diluted with DCM and washed with water, brine and 1M $K_2CO_3$. The organic phase was dried with $Na_2SO_4$, filtered, and evaporated. The crude was purified with flash chromatography (DCM/MeOH=9/1) to obtain (R)-quinuclidin-3-yl 2-phenyl-2-(2,2,2-trifluoroethylsulfonamido)acetate (60 mg; 41% yield).

Preparation of (3R)-1-(2-oxo-2-phenylethyl)-3-(2-phenyl-2-(2,2,2-trifluoroethylsulfonamido)acetoxy)-1-azoniabicyclo[2.2.2]octane bromide (C79)

To a solution of (R)-quinuclidin-3-yl 2-phenyl-2-(2,2,2-trifluoroethyl-sulfonamido)acetate (C78) (60 mg, 0.15 mmol) in EtOAc (2 ml), was added 2-bromo-1-phenylethanone (35.3 mg, 0.18 mmol). The reaction was stirred at RT for 16 hours. Then the solvent was evaporated, and the crude was purified by flash chromatography (DCM/MeOH=9/1) to obtain (3R)-1-(2-oxo-2-phenylethyl)-3-(2-phenyl-2-(2,2,2-trifluoroethylsulfonamido)acetoxy)-1-azoniabicyclo[2.2.2]octane bromide (5 mg; 6% yield).

$^1$H NMR (300 MHz, Acetonitrile-$d_3$) δ ppm 7.91-8.06 (m, 2H), 7.71-7.83 (m, 1H), 7.67 (d, 1H), 7.56-7.64 (m, 2H), 7.37-7.56 (m, 5H), 5.36 and 5.37 (d, 1H), 5.16-5.31 (m, 1H), 4.91 and 4.98 (d, 1H), 4.84 and 4.91 (d, 1H), 3.94-4.33 (m, 3H), 3.50-3.93 (m, 5H), 2.32-2.42 and 2.42-2.55 (m, 1H), 2.00-2.23 (m, 3H), 1.79-1.92 (m, 1H);

LC-MS (ESI POS): 525.10 (M+).

Example 34

Preparation of ((3R)-1-(2-oxo-2-phenylethyl)-3-(2-phenyl-2-(phenylmethylsulfonamido)acetoxy)-1-azoniabicyclo[2.2.2]octane bromide (C81)

Scheme 35

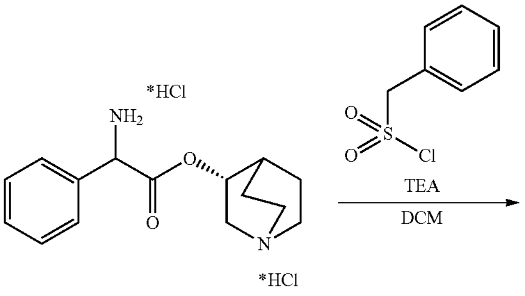

I25

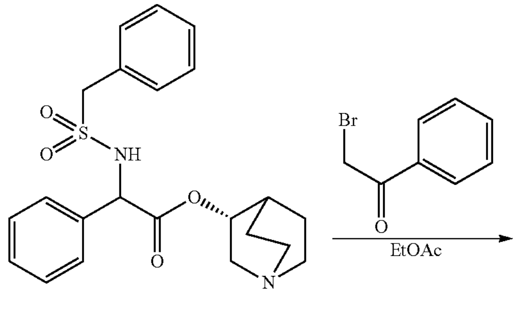

C80

-continued

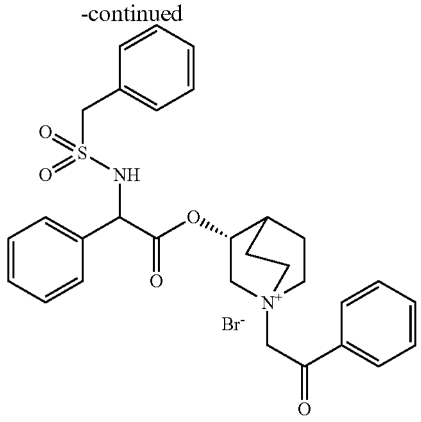

C81

Preparation of (R)-quinuclidin-3-yl 2-phenyl-2-(phenylmethylsulfonamido)acetate (C80)

To a solution of (R)-quinuclidin-3-yl 2-amino-2-phenylacetate dihydrochloride (I25) (100 mg, 0.30 mmol) in DCM (4 ml) and triethylamine (65.8 μl, 0.90 mmol), was added phenylmethanesulfonyl chloride (68.6 mg, 0.36 mmol). The reaction was stirred at RT for 13 hours. DCM was evaporated, and the crude was taken up with EtOAc and washed 1M $Na_2CO_3$, water and brine. The organic phase was dried over $Na_2SO_4$, filtered and evaporated to obtain (R)-quinuclidin-3-yl 2-phenyl-2-(phenylmethylsulfonamido)-acetate (74 mg; 59.5% yield).

Preparation of (3R)-1-(2-oxo-2-phenylethyl)-3-(2-phenyl-2-(phenylmethylsulfonamido)acetoxy)-1-azoniabicyclo[2.2.2]octane bromide (C81)

To a solution of (R)-quinuclidin-3-yl 2-phenyl-2-(phenylmethylsulfonamido)-acetate (C80) (41 mg, 0.10 mmol) in EtOAc (2 ml), was added 2-bromo-1-phenylethanone (21.7 mg, 0.11 mmol), and the reaction was stirred at RT for 1 hour. The solvent was evaporated, and the crude was triturated with $Et_2O$ to obtain (3R)-1-(2-oxo-2-phenylethyl)-3-(2-phenyl-2-(phenylmethylsulfonamido)acetoxy)-1-azoniabicyclo[2.2.2]octane bromide (50 mg; 82% yield).

$^1$H NMR (300 MHz, DMSO-$d_6$) δ ppm 8.42 (d, 1H), 7.88-8.07 (m, 2H), 7.69-7.81 (m, 1H), 7.53-7.67 (m, 2H), 7.24-7.52 (m, 10H), 5.18-5.33 (m, 1H), 5.08-5.14 (m, 1H), 5.13 (d, 1H), 4.44 (d, 1H), 4.37 (d, 1H), 4.02-4.21 (m, 1H), 3.45-3.84 (m, 5H), 2.32-2.42 (m, 1H), 1.43-2.15 (m, 4H);

LC-MS (ESI POS): 533.23 (M+).

Example 35

Preparation of (3R)-3-(2-(4-fluorophenyl)-2-(phenylsulfonamido)acetoxy)-1-(2-oxo-2-phenylethyl)-1-azoniabicyclo[2.2.2]octane 2,2,2-trifluoroacetate (C84)

Scheme 36

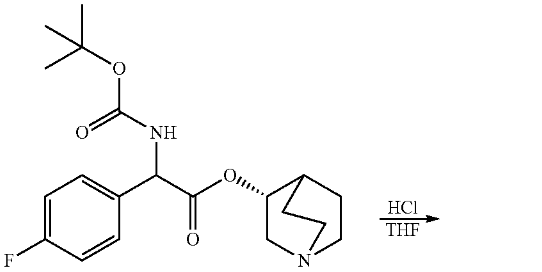

C50

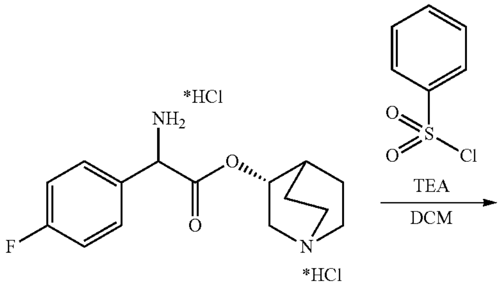

I82

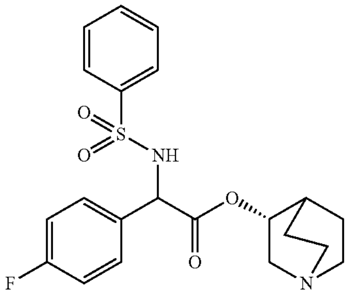

C83

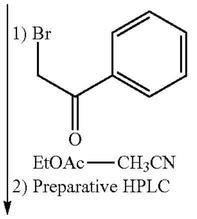

-continued

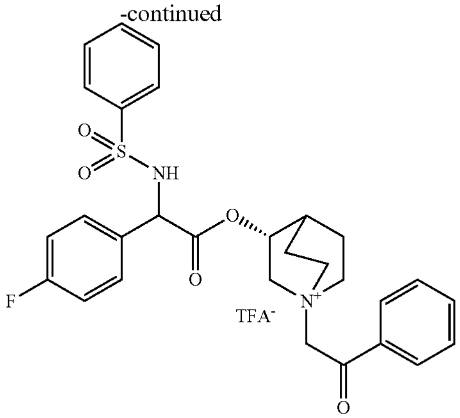

C84

Preparation of (R)-quinuclidin-3-yl 2-amino-2-(4-fluorophenyl)acetate dihydrochloride (I82)

To a solution of (R)-quinuclidin-3-yl 2-(tert-butoxycarbonylamino)-2-(4-fluorophenyl)acetate (C50) (350 mg, 0.92 mmol) in THF (20 ml), was added 37% hydrogen chloride (1.0 ml, 12.2 mmol), and the reaction was stirred at RT for 15 hours. Then a second portion of 37% hydrogen chloride (1.0 ml, 12.2 mmol) was added again, and the reaction was further stirred at RT for 24 hours. Then the volatiles were evaporated under vacuum to obtain (R)-quinuclidin-3-yl 2-amino-2-(4-fluorophenyl)acetate dihydrochloride (325 mg; quantitative yield).

Preparation of (R)-quinuclidin-3-yl 2-(4-fluorophenyl)-2-(phenylsulfonamido)acetate (C83)

To a suspension of (R)-quinuclidin-3-yl 2-amino-2-(4-fluorophenyl)acetate dihydrochloride (I82) (325 mg, 0.92 mmol) in DCM (10 ml), were added triethylamine (386 μl, 2.78 mmol) and benzenesulfonyl chloride (142 μl, 1.11 mmol). The reaction was stirred at RT for 4 hours, and then the solvent was evaporated. The residue was taken up with EtOAc and washed with 1M $Na_2CO_3$, water and then brine, dried over $Na_2SO_4$ and evaporated to dryness to obtain (R)-quinuclidin-3-yl 2-(4-fluorophenyl)-2-(phenylsulfonamido)acetate (150 mg; 39% yield).

Preparation of (3R)-3-(2-(4-fluorophenyl)-2-(phenylsulfonamido)acetoxy)-1-(2-oxo-2-phenylethyl)-1-azoniabicyclo[2.2.2]octane 2,2,2-trifluoroacetate (C84)

To a solution of (R)-quinuclidin-3-yl 2-(4-fluorophenyl)-2-(phenylsulfonamido)-acetate (C83) (150 mg, 0.36 mmol) in EtOAc (2 ml) and acetonitrile (2 ml), was added 2-bromo-1-phenylethanone (78 mg, 0.39 mmol). The reaction was stirred at RT for 15 hours. The solvent was evaporated, and the crude was purified by preparative HPLC to obtain (3R)-3-(2-(4-fluorophenyl)-2-(phenylsulfonamido)acetoxy)-1-(2-oxo-2-phenylethyl)-1-azoniabicyclo[2.2.2]octane 2,2,2-trifluoroacetate (97.9 mg; 42% yield).

$^1H$ NMR (300 MHz, DMSO-$d_6$) δ ppm 9.02 (d, 1H), 7.89-8.09 (m, 2H), 7.66-7.81 (m, 3H), 7.32-7.68 (m, 7H), 7.02-7.21 (m, 2H), 5.20-5.30 (m, 1H), 5.11 and 5.14 (s, 2H), 4.94-5.10 (m, 1H), 3.94-4.14 (m, 1H), 3.38-3.66 (m, 5H), 2.14-2.25 (m, 1H), 1.53-2.09 (m, 4H);

LC-MS (ESI POS): 537.18 (M+).

Example 36

Preparation of (3R)-3-(2-benzamido-2-phenylacetoxy)-1-(2-oxo-2-phenylethyl)-1-azoniabicyclo[2.2.2]octane chloride (C86)

Scheme 37

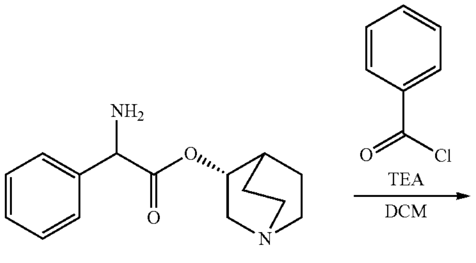

I30

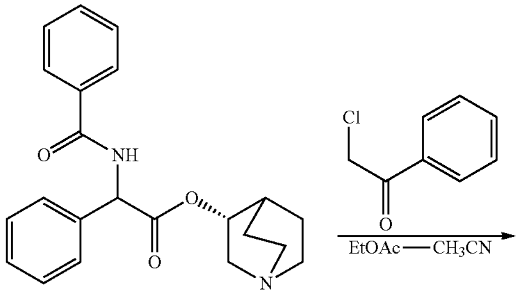

C85

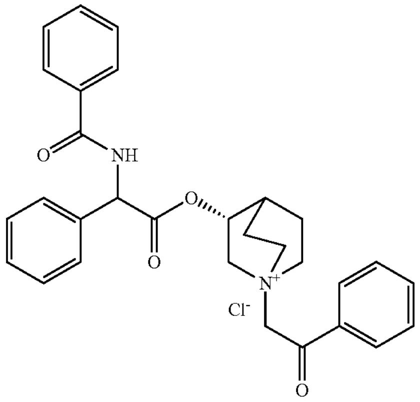

C86

Preparation of (R)-quinuclidin-3-yl 2-benzamido-2-phenylacetate (C85)

To a solution of (R)-quinuclidin-3-yl 2-amino-2-phenylacetate (I30) (100 mg, 0.38 mmol) in DCM (4 ml) and triethylamine (0.08 ml, 0.58 mmol), was added benzoyl chloride (58.0 μl, 0.50 mmol). The reaction was stirred at RT for 1.5 hours, and then the volatiles were evaporated. The crude was purified by flash chromatography (DCM/MeOH/$NH_4OH$=95/5/0.3) to obtain (R)-quinuclidin-3-yl 2-benzamido-2-phenylacetate (70 mg; 50% yield).

Preparation of (3R)-3-(2-benzamido-2-phenylacetoxy)-1-(2-oxo-2-phenylethyl)-1-azoniabicyclo[2.2.2]octane chloride (C86)

To a solution of (R)-quinuclidin-3-yl 2-benzamido-2-phenylacetate (C85) (70 mg, 0.19 mmol) in EtOAc (1 ml) and acetonitrile (1 ml), was added 2-chloro-1-phenylethanone (32.7 mg, 0.21 mmol). The reaction was stirred at RT for 24 hours, and then the solvents were evaporated and the residue was triturated with EtOAc (8 ml) to obtain (3R)-3-(2-benzamido-2-phenylacetoxy)-1-(2-oxo-2-phenylethyl)-1-azoniabicyclo[2.2.2]octane chloride (72 mg; 72% yield).

$^1$H NMR (300 MHz, DMSO-$d_6$) δ ppm 9.38 (d, J=7.04 Hz, 1H), 7.88-8.11 (m, 4H), 7.69-7.87 (m, 1H), 7.12-7.68 (m, 10H), 5.78 (d, J=7.04 Hz, 1H), 5.26 (s, 2H), 5.15-5.24 (m, 1H), 4.05-4.27 (m, 1H), 3.81-3.94 (m, 1H), 3.54-3.81 (m, 4H), 2.19-2.31 (m, 1H), 1.91-2.14 (m, 2H), 1.74-1.91 (m, 1H), 1.61-1.74 (m, 1H);

LC-MS (ESI POS): 483.02 (M+).

Example 37

Preparation of (3R)-3-(2-benzamido-2-phenylacetoxy)-1-(2-(4-fluorophenyl)-2-oxoethyl)-1-azoniabicyclo[2.2.2]octane 2,2,2-trifluoroacetate (C87)

Scheme 38

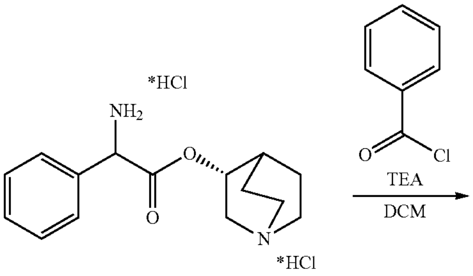

I25

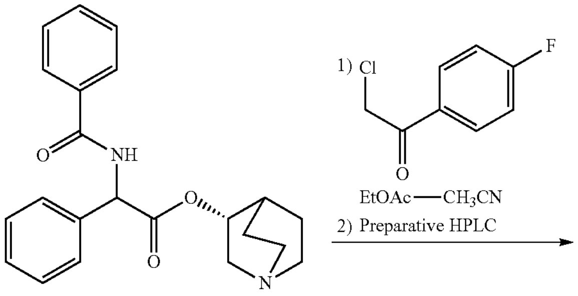

C85

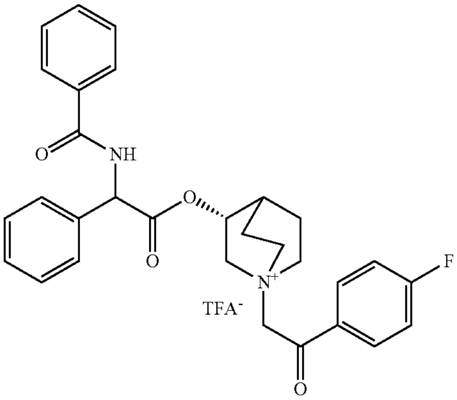

C87

Preparation of (R)-quinuclidin-3-yl 2-benzamido-2-phenylacetate (C85)

To a suspension of (R)-quinuclidin-3-yl 2-amino-2-phenylacetate dihydrochloride (I25) (0.67 g, 2.01 mmol) in DCM (25 ml), were sequentially added triethylamine (0.84 ml, 6.04 mmol) and benzoyl chloride (0.28 ml, 2.42 mmol). The reaction was stirred at RT for 4 hours, and then the solvent was evaporated. The crude was taken up with EtOAc and washed with water and brine, dried over $Na_2SO_4$ and evaporated to obtain (R)-quinuclidin-3-yl 2-benzamido-2-phenylacetate (310 mg; 42% yield).

Preparation of (3R)-3-(2-benzamido-2-phenylacetoxy)-1-(2-(4-fluorophenyl)-2-oxoethyl)-1-azoniabicyclo[2.2.2]octane 2,2,2-trifluoroacetate (C87)

To a solution of (R)-quinuclidin-3-yl 2-benzamido-2-phenylacetate (C85) (77.5 mg, 0.21 mmol) in EtOAc (1 ml) and acetonitrile (5 ml), is added 2-chloro-1-(4-fluorophenyl)ethanone (40.4 mg, 0.23 mmol). The reaction was stirred at RT for 15 hours, and then the solvent was evaporated. The crude was triturated with i-$Pr_2O$/EtOAc (5/1) and then purified by preparative HPLC to obtain (3R)-3-(2-benzamido-2-phenylacetoxy)-1-(2-(4-fluorophenyl)-2-oxoethyl)-1-azoniabicyclo[2.2.2]octane 2,2,2-trifluoroacetate (50.8 mg; 39% yield).

$^1$H NMR (300 MHz, DMSO-$d_6$) δ ppm 9.27 (d, 1H), 7.99-8.16 (m, 2H), 7.84-7.99 (m, 2H), 7.28-7.67 (m, 10H), 5.66-5.84 (m, 1H), 5.26 (m, 1H), 5.14 and 5.15 (s, 2H), 3.97-4.30 (m, 1H), 3.36-3.73 (m, 5H), 2.18-2.26 and 2.38-2.46 (m, 1H), 1.57-2.17 (m, 4H);

LC-MS (ESI POS): 501.08 (M+).

The compounds listed in Table 5 were obtained as previously described for C87, starting from compound C85 and the suitable commercially available alkylating agents.

TABLE 5

| Compound | Structure | Yield and appearance | Analytical |
|---|---|---|---|
| C88 | 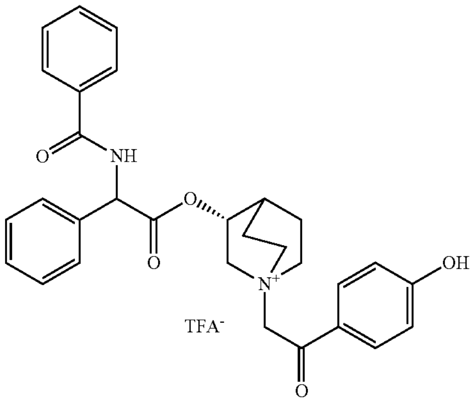 [SMILES: O=C(C[N+]12CCC(CC1)[C@@H](OC(=O)C(NC(=O)c1ccccc1)c1ccccc1)C2)c1ccc(O)cc1 ; "TFA-"] Mixture of diastereoisomers | 35% yield | LC-MS (ESI POS): 499.06 ($M^+$) $^1$H NMR (300 MHz, DMSO-$d_6$) δ ppm 10.72 (br. s., 1 H), 9.25 and 9.26 (d, 1 H), 7.90-8.05 (m, 2 H), 7.80-7.90 (m, 2 H), 7.30-7.65 (m, 8 H), 6.82-6.99 (m, 2 H), 5.65-5.78 (m, 1 H), 5.17-5.33 (m, 1 H), 5.03 and 5.05 (br. s., 2 H), 4.02-4.26 (m, 1 H), 3.60-3.86 (m, 5 H), 2.17-2.26 and 2.34-2.46 (m, 1 H), 1.51-2.15 (m, 4 H) |
| C89 | 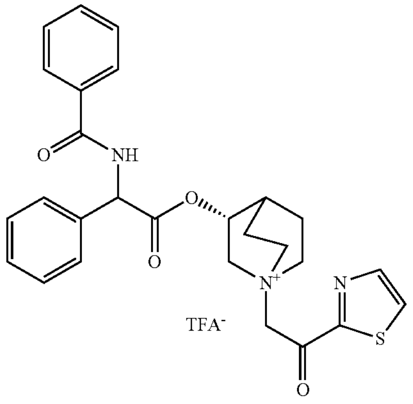 [SMILES: O=C(NC(C(=O)O[C@H]1C[N+]2(CC(=O)c3nccs3)CCC1CC2)c1ccccc1)c1ccccc1 ; "TFA-"] Mixture of diastereoisomers | 42% yield | LC-MS (ESI POS): 490.15 ($M^+$) $^1$H NMR (300 MHz, DMSO-$d_6$) δ ppm 9.25 and 9.27 (d, 1 H), 8.38 (d, 1 H), 8.24 (d, 1 H), 7.87-7.99 (m, 2 H), 7.33-7.60 (m, 8 H), 5.67-5.73 and 5.74-5.78 (m, 1 H), 5.22-5.32 (m, 1 H), 5.18 and 5.20 (s, 2 H), 4.03-4.29 (m, 1 H), 3.56-3.89 (m, 5 H), 2.18-2.25 and 2.37-2.47 (m, 1 H), 1.34-2.15 (m, 4 H) |

TABLE 5-continued

| Compound | Structure | Yield and appearance | Analytical |
|---|---|---|---|
| C90 | 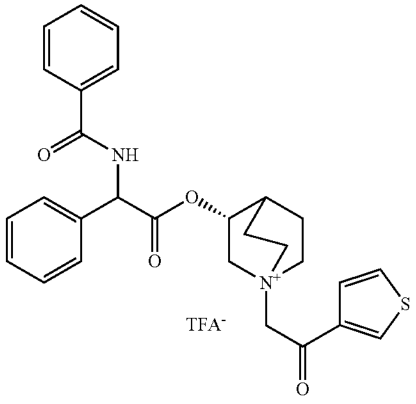 [SMILES: O=C(C[N+]12CCC(CC1)[C@@H](OC(=O)C(NC(=O)c1ccccc1)c1ccccc1)C2)c1ccsc1 ; "TFA-"]<br>Mixture of diastereoisomers | 45% yield | LC-MS (ESI POS): 489.16 ($M^+$)<br>$^1$H NMR (300 MHz, DMSO-$d_6$) δ ppm 9.26 (dd, 1 H) 8.61 (ddd, 1 H) 7.86-8.03 (m, 2 H) 7.68-7.81 (m, 1 H) 7.31-7.64 (m, 9 H) 5.65-5.82 (m, 1 H) 5.18-5.33 (m, 1 H) 5.02 (d, 2 H) 4.03-4.24 (m, 1 H) 3.73-3.85 (m, 4 H) 2.18-2.46 (m, 1 H) 1.74-2.14 (m, 4 H) 1.52-1.74 (m, 1 H) |
| C91 | 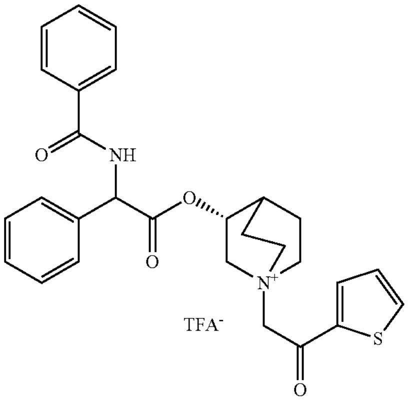 [SMILES: O=C(NC(C(=O)O[C@H]1C[N+]2(CC(=O)c3cccs3)CCC1CC2)c1ccccc1)c1ccccc1 ; "TFA-"]<br>Mixture of diastereoisomers | 31% yield | LC-MS (ESI POS): 489.02 ($M^+$)<br>$^1$H NMR (300 MHz, DMSO-$d_6$) δ ppm 9.37 and 9.45 (d, 1 H), 8.18-8.30 (m, 1 H), 8.12 and 8.14 (dd, 1 H), 7.89-8.02 (m, 2 H), 7.17-7.69 (m, 9 H), 5.74 and 5.80 (d, 1 H), 5.19-5.29 (m, 1 H), 5.16 and 5.17 (s, 2 H), 4.07-4.30 (m, 1 H), 3.50-4.02 (m, 5 H), 2.17-2.30 and 2.35-2.42 (m, 1 H), 1.50-2.14 (m, 4 H) |

Example 38

Preparation of (3R)-3-(2-acetamido-2-phenylacetoxy)-1-(2-oxo-2-phenylethyl)-1-azoniabicyclo[2.2.2]octane 2,2,2-trifluoroacetate (C93)

Scheme 39

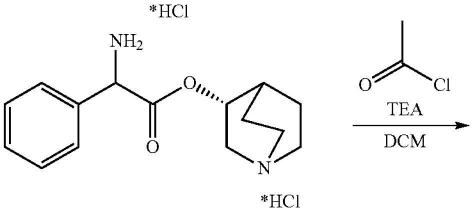

I25

-continued

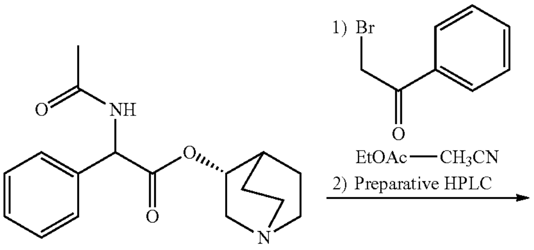

C92

-continued

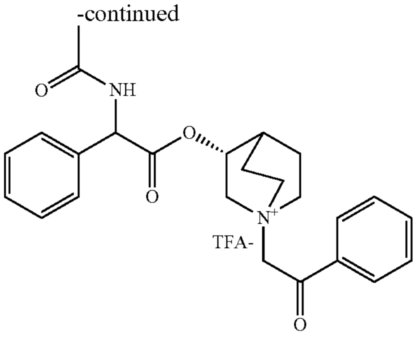

C93

Preparation of (R)-quinuclidin-3-yl 2-acetamido-2-phenylacetate (C92)

To a suspension of (R)-quinuclidin-3-yl 2-amino-2-phenylacetate dihydrochloride (I25) (140 mg, 0.42 mmol) in DCM (10 ml), were sequentially added triethylamine (175 μl, 1.26 mmol) and acetyl chloride (35.8 μl, 0.50 mmol). The reaction was stirred at RT for 2 hours, and then the solvent was evaporated. The residue was taken up with little EtOAc, and the insoluble was filtered off. The organic phase was evaporated to dryness achieving (R)-quinuclidin-3-yl 2-acetamido-2-phenylacetate (127 mg; quantitative yield).

Preparation of (3R)-3-(2-acetamido-2-phenylacetoxy)-1-(2-oxo-2-phenylethyl)-1-azoniabicyclo[2.2.2]octane 2,2,2-trifluoroacetate (C93)

To a solution of (R)-quinuclidin-3-yl 2-acetamido-2-phenylacetate (C92) (127 mg, 0.42 mmol) in EtOAc (2 ml) and acetonitrile (5 ml), was added 2-bromo-1-phenylethanone (92 mg, 0.46 mmol), and the reaction was stirred at RT for 72 hours. The solvent was evaporated, and the crude was purified by preparative HPLC to obtain (3R)-3-(2-acetamido-2-phenylacetoxy)-1-(2-oxo-2-phenylethyl)-1-azoniabicyclo[2.2.2]octane 2,2,2-trifluoroacetate (20.5 mg; 9% yield).

$^1$H NMR (300 MHz, DMSO-$d_6$) δ ppm 8.77 and 8.79 (d, 1H), 7.89-8.04 (m, 2H), 7.70-7.82 (m, 1H), 7.55-7.69 (m, 2H), 7.29-7.54 (m, 5H), 5.44 and 5.48 (d, 1H), 5.18-5.27 (m, 1H), 5.15 and 5.18 (s, 2H), 3.98-4.21 (m, 1H), 3.52-3.81 (m, 5H), 1.94 (s, 3H), 1.58-2.45 (m, 5H);

LC-MS (ESI POS): 421.16 (M+).

Example 39

Preparation of (3R)-1-(2-oxo-2-phenylethyl)-3-(2-phenyl-2-pivalamidoacetoxy)-1-azoniabicyclo[2.2.2]octane 2,2,2-trifluoroacetate (C95)

Scheme 40

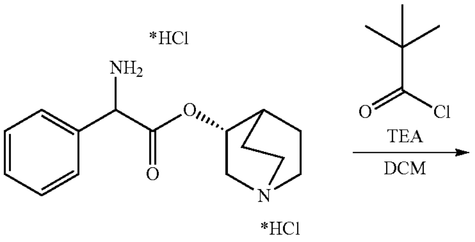

I25

-continued

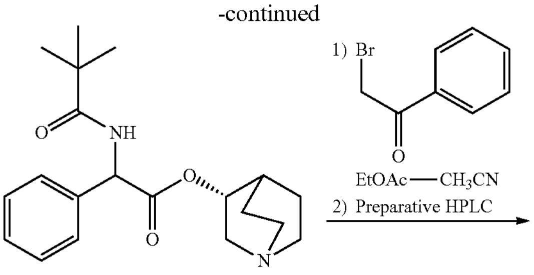

C94

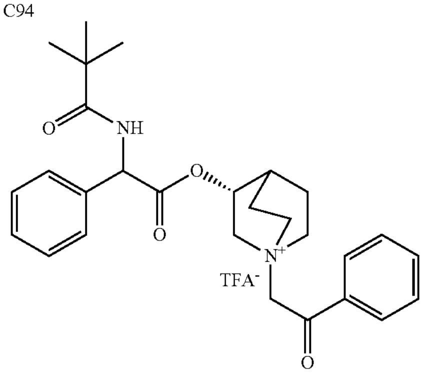

C95

Preparation of (R)-quinuclidin-3-yl 2-phenyl-2-pivalamidoacetate (C94)

To a suspension of (R)-quinuclidin-3-yl 2-amino-2-phenylacetate dihydrochloride (I25) (140 mg, 0.42 mmol) in DCM (5 ml), were sequentially added triethylamine (175 μl, 1.26 mmol) and pivaloyl chloride (62.1 μl, 0.50 mmol). The reaction was stirred at RT for 2 hours, and then the solvent was evaporated. The residue was taken up with EtOAc and washed with $Na_2CO_3$, water and brine, dried over $Na_2SO_4$, filtered and evaporated to obtain (R)-quinuclidin-3-yl 2-phenyl-2-pivalamidoacetate (95 mg; 66% yield).

Preparation of (3R)-1-(2-oxo-2-phenylethyl)-3-(2-phenyl-2-pivalamidoacetoxy)-1-azoniabicyclo[2.2.2]octane 2,2,2-trifluoroacetate (C95)

To a solution of (R)-quinuclidin-3-yl 2-phenyl-2-pivalamidoacetate (C94) (95 mg, 0.28 mmol) in EtOAc (2 ml) and acetonitrile (2 ml), was added 2-bromo-1-phenylethanone (60.4 mg, 0.30 mmol), and the reaction was stirred at RT for 15 hours. The solvent was evaporated, and the crude was purified by preparative HPLC to obtain (3R)-1-(2-oxo-2-phenylethyl)-3-(2-phenyl-2-pivalamidoacetoxy)-1-azoniabicyclo[2.2.2]octane 2,2,2-trifluoroacetate (118.6 mg; 75% yield).

$^1$H NMR (300 MHz, DMSO-$d_6$) δ ppm 8.21 (t, 1H) 7.91-8.05 (m, 2H) 7.69-7.83 (m, 1H) 7.55-7.69 (m, 2H) 7.26-7.54 (m, 5H) 5.40-5.54 (m, 1H) 5.16 (d, 2H) 5.08-5.34 (m, 1H) 4.01-4.34 (m, 3H) 3.43-3.79 (m, 3H) 2.32-2.45 (m, 1H) 1.87-2.16 (m, 3H) 1.74 (s, 1H) 1.17 (s, 9H);

LC-MS (ESI POS): 463.19 (M+).

The compounds listed in Table 6 were obtained as previously described for C95, treating intermediate I25 with the suitable commercially available acyl halides, followed by quaternization with 2-bromo-1-phenylethanone and purification by preparative HPLC.

TABLE 6

| Compound | Structure | Yield and appearance | Analytical |
|---|---|---|---|
| C96 | 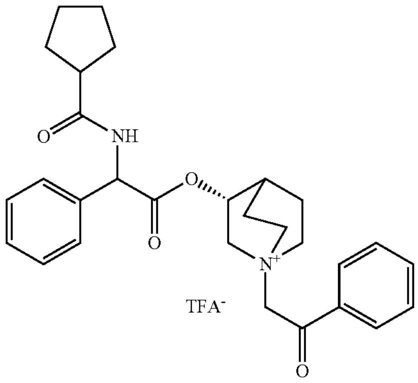 [SMILES: O=C(C[N+]12CCC(CC1)[C@@H](OC(=O)C(NC(=O)C1CCCC1)c1ccccc1)C2)c1ccccc1 ; "TFA-"] Mixture of diastereoisomers | 34% yield (Over two steps) | LC-MS (ESI POS): 475.15 ($M^+$) $^1H$ NMR (300 MHz, DMSO-$d_6$) δ ppm 8.68 (t, 1 H) 7.88-8.10 (m, 2 H) 7.69-7.83 (m, 1 H) 7.54-7.69 (m, 2 H) 7.30-7.53 (m, 5 H) 5.37-5.54 (m, 1 H) 5.16 (d, 2 H) 5.05-5.31 (m, 1 H) 3.98-4.22 (m, 1 H) 3.61-3.85 (m, 5 H) 2.70-2.86 (m, 2 H) 2.34-2.43 (m, 1 H) 1.88-2.15 (m, 3 H) 1.47-1.86 (m, 8 H) |
| C97 | 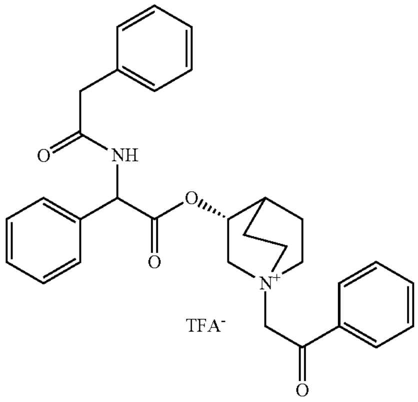 [SMILES: O=C(Cc1ccccc1)NC(C(=O)O[C@H]1C[N+]2(CC(=O)c3ccccc3)CCC1CC2)c1ccccc1 ; "TFA-"] Mixture of diastereoisomers | 51% yield (Over two steps) | LC-MS (ESI POS): 497.16 ($M^+$) $^1H$ NMR (300 MHz, DMSO-$d_6$) δ ppm 9.01 and 9.04 (d, 1 H), 7.90-8.08 (m, 2 H), 7.69-7.81 (m, 1 H), 7.56-7.69 (m, 2 H), 7.36-7.56 (m, 5 H), 7.11-7.35 (m, 5 H), 5.43 and 5.47 (d, 1 H), 5.17-5.28 (m, 1 H), 5.01-5.17 (m, 2 H), 3.94-4.22 (m, 1 H), 3.37-3.76 (m, 7 H), 2.09-2.19 and 2.31-2.41 (m, 1 H), 1.30-2.09 (m, 4 H) |
| C98 | 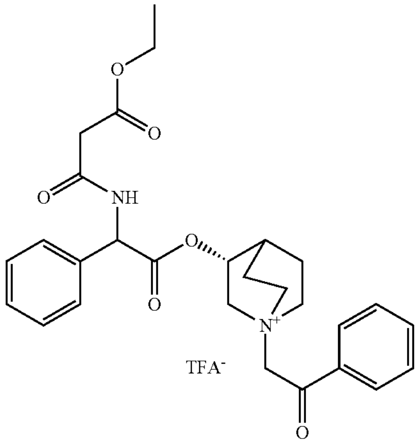 [SMILES: CCOC(=O)CC(=O)NC(C(=O)O[C@H]1C[N+]2(CC(=O)c3ccccc3)CCC1CC2)c1ccccc1 ; "TFA-"] Mixture of diastereoisomers | 43% yield (Over two steps) | LC-MS (ESI POS): 493.19 ($M^+$) $^1H$ NMR (300 MHz, DMSO-$d_6$) δ ppm 9.05 (dd, 1 H) 7.90-8.05 (m, 2 H) 7.70-7.83 (m, 1 H) 7.55-7.68 (m, 2 H) 7.33-7.53 (m, 5 H) 5.50 (dd, 1 H) 5.09-5.30 (m, 1 H) 5.17 (d, 2 H) 4.12-4.23 (m, 1 H) 4.08 (q, 2 H) 3.53-3.76 (m, 5 H) 3.32-3.48 (m, 2 H) 2.36-2.44 (m, 1 H) 1.88-2.18 (m, 3 H) 1.53-1.88 (m, 1 H) 1.17 (t, 3 H) |

TABLE 6-continued

| Compound | Structure | Yield and appearance | Analytical |
|---|---|---|---|
| C99 | 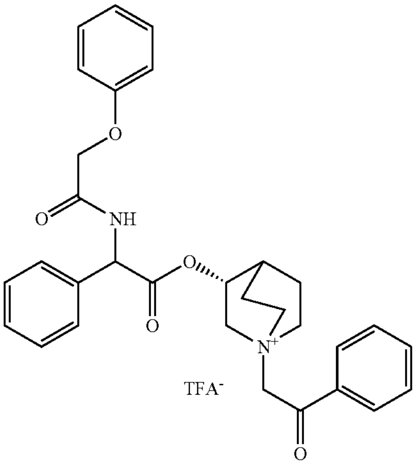 [SMILES: O=C(COc1ccccc1)NC(C(=O)O[C@H]1C[N+]2(CC(=O)c3ccccc3)CCC1CC2)c1ccccc1 ; "TFA-"] Mixture of diastereoisomers | 45% yield (Over two steps) | LC-MS (ESI POS): 513.25 ($M^+$)<br>$^1$H NMR (300 MHz, DMSO-$d_6$) δ ppm 8.98 (dd, 1 H) 7.88-8.07 (m, 2 H) 7.70-7.84 (m, 1 H) 7.55-7.68 (m, 2 H) 7.34-7.55 (m, 5 H) 7.20-7.34 (m, 2 H) 6.87-7.06 (m, 3 H) 5.59 (t, 1 H) 5.18-5.31 (m, 1 H) 5.15 (d, 2 H) 4.65 (s, 2 H) 4.01-4.23 (m, 1 H) 3.60-3.84 (m, 4 H) 2.33-2.44 (m, 1 H) 1.58-2.14 (m, 5 H) |
| C100 | 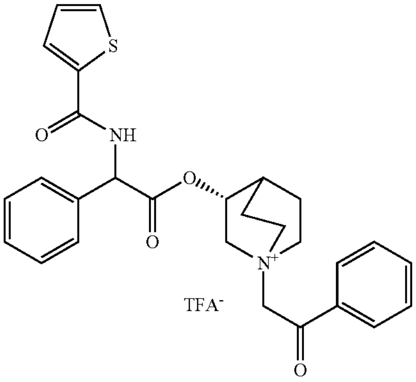 [SMILES: O=C(C[N+]12CCC(CC1)[C@@H](OC(=O)C(NC(=O)c1cccs1)c1ccccc1)C2)c1ccccc1 ; "TFA-"] Mixture of diastereoisomers | 21% yield (Over two steps) | LC-MS (ESI POS): 489.22 ($M^+$)<br>$^1$H NMR (300 MHz, DMSO-$d_6$) δ ppm 9.26 and 9.28 (d, 1 H) 7.89-8.11 (m, 3 H) 7.70-7.89 (m, 2 H) 7.37-7.66 (m, 7 H) 7.15-7.21 (m, 1 H) 5.68 and 5.71 (d, 1 H) 5.21-5.37 (m, 1 H) 5.16 and 5.17 (br. s., 2 H) 4.01-4.27 (m, 1 H) 3.71-3.89 (m, 5 H) 2.17-2.25 and 2.36-2.46 (m, 1 H) 1.50-2.15 (m, 4 H) |
| C101 | 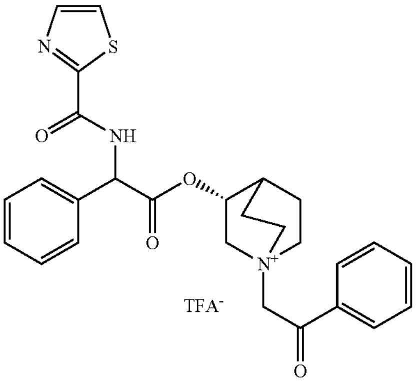 [SMILES: O=C(C[N+]12CCC(CC1)[C@@H](OC(=O)C(NC(=O)c1nccs1)c1ccccc1)C2)c1ccccc1 ; "TFA-"] Mixture of diastereoisomers | 16% yield (Over two steps) | LC-MS (ESI POS): 490.16 ($M^+$)<br>$^1$H NMR (300 MHz, DMSO-$d_6$) δ ppm 9.42 and 9.45 (d, 1 H) 8.03-8.21 (m, 2 H) 7.92-8.03 (m, 2 H) 7.70-7.84 (m, 1 H) 7.48-7.68 (m, 4 H) 7.30-7.48 (m, 3 H) 5.79 and 5.82 (d, 1 H) 5.21-5.35 (m, 1 H) 5.15 (s, 2 H) 4.04-4.23 (m, 1 H) 3.38-3.89 (m, 5 H) 2.20-2.27 and 2.34-2.44 (m, 1 H) 1.52-2.14 (m, 4 H) |

TABLE 6-continued

| Compound | Structure | Yield and appearance | Analytical |
|---|---|---|---|
| C102 | 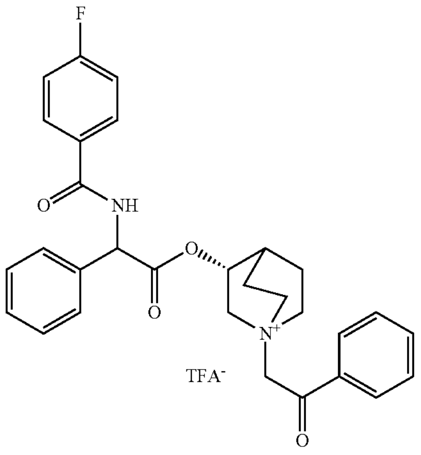 [SMILES: O=C(C[N+]12CCC(CC1)[C@@H](OC(=O)C(NC(=O)c1ccc(F)cc1)c1ccccc1)C2)c1ccccc1 ; "TFA-"]<br>Mixture of diastereoisomers | 33% yield (Over two steps) | LC-MS (ESI POS): 501.24 ($M^+$)<br>$^1H$ NMR (300 MHz, DMSO-$d_6$) δ ppm 9.28 and 9.30 (d, 1 H) 7.87-8.13 (m, 4 H) 7.69-7.85 (m, 1 H) 7.50-7.69 (m, 4 H) 7.37-7.50 (m, 3 H) 7.24-7.36 (m, 2 H) 5.70 and 5.74 (d, 1 H) 5.16 and 5.18 (s, 2 H) 5.05-5.37 (m, 1 H) 4.00-4.27 (m, 1 H) 3.50-3.85 (m, 5 H) 2.17-2.25 and 2.36-2.47 (m, 1 H) 1.57-2.14 (m, 4 H) |
| C103 | 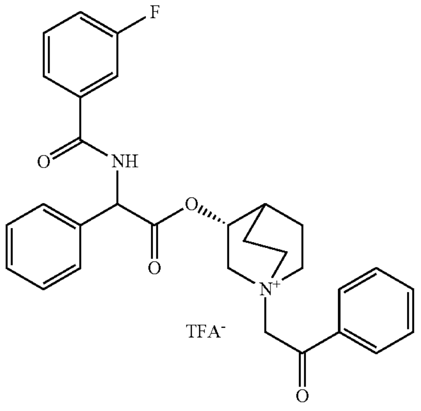 [SMILES: O=C(C[N+]12CCC(CC1)[C@@H](OC(=O)C(NC(=O)c1cccc(F)c1)c1ccccc1)C2)c1ccccc1 ; "TFA-"]<br>Mixture of diastereoisomers | 35% yield (Over two steps) | LC-MS (ESI POS): 501.23 ($M^+$)<br>$^1H$ NMR (300 MHz, DMSO-$d_6$) δ ppm 9.36 and 9.38 (d, 1 H) 7.90-8.06 (m, 2 H) 7.68-7.88 (m, 3 H) 7.50-7.68 (m, 5 H) 7.34-7.50 (m, 4 H) 5.71 and 5.74 (d, 1 H) 5.21-5.44 (m, 1 H) 5.16 and 5.18 (s, 2 H) 3.99-4.25 (m, 1 H) 3.48-3.87 (m, 5 H) 2.20-2.27 and 2.39-2.46 (m, 1 H) 1.57-2.15 (m, 4 H) |
| C104 | 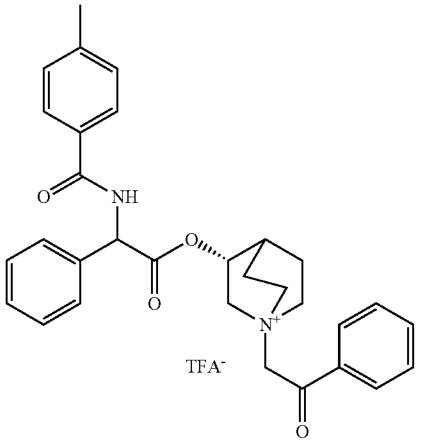 [SMILES: Cc1ccc(C(=O)NC(C(=O)O[C@H]2C[N+]3(CC(=O)c4ccccc4)CCC2CC3)c2ccccc2)cc1 ; "TFA-"]<br>Mixture of diastereoisomers | 21% yield (Over two steps) | LC-MS (ESI POS): 497.22 ($M^+$)<br>$^1H$ NMR (300 MHz, DMSO-$d_6$) δ ppm 9.18 (d, 1 H) 7.96-8.01 (m, 2 H) 7.82-7.90 (m, 2 H) 7.72-7.80 (m, 1 H) 7.60-7.67 (m, 2 H) 7.52-7.60 (m, 2 H) 7.34-7.48 (m, 3 H) 7.21-7.32 (m, 2 H) 5.73 (d, 1 H) 5.21-5.32 (m, 1 H) 5.18 (s, 2 H) 4.06-4.27 (m, 1 H) 3.73-3.85 (m, 1 H) 3.51-3.73 (m, 4 H) 2.36 (s, 3 H) 2.16-2.26 (m, 1 H) 1.49-2.11 (m, 4 H) |

TABLE 6-continued
| Compound | Structure | Yield and appearance | Analytical |
|---|---|---|---|
| C105 | 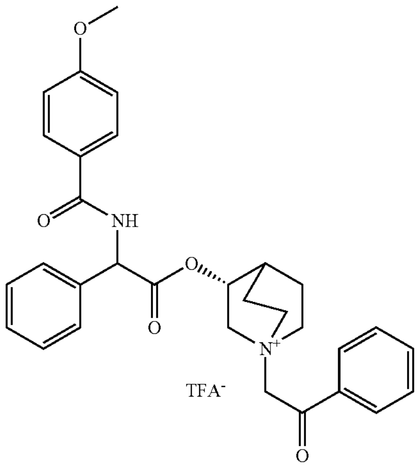 [SMILES: COc1ccc(C(=O)NC(C(=O)O[C@H]2C[N+]3(CC(=O)c4ccccc4)CCC2CC3)c2ccccc2)cc1 ; "TFA-"] Mixture of diastereoisomers | 46% yield (Over two steps) | LC-MS (ESI POS): 513.26 ($M^+$) $^1$H NMR (300 MHz, DMSO-$d_6$) δ ppm 9.08 and 9.10 (d, 1 H) 7.85-8.08 (m, 4 H) 7.69-7.83 (m, 1 H) 7.50-7.68 (m, 4 H) 7.29-7.50 (m, 3 H) 6.88-7.10 (m, 2 H) 5.68 and 5.72 (d, 1 H) 5.16 and 5.17 (s, 2 H) 5.06-5.37 (m, 1 H) 4.05-4.24 (m, 1 H) 3.82 (s, 3 H) 3.45-3.77 (m, 5 H) 2.20-2.26 and 2.37-2.46 (m, 1 H) 1.58-2.14 (m, 4 H) |
Example 40
Preparation of (3R)-3-(2-benzamido-2-(4-methoxyphenyl)acetoxy)-1-(2-oxo-2-phenylethyl)-1-azoniabicyclo[2.2.2]octane 2,2,2-trifluoroacetate (C108)
Scheme 41
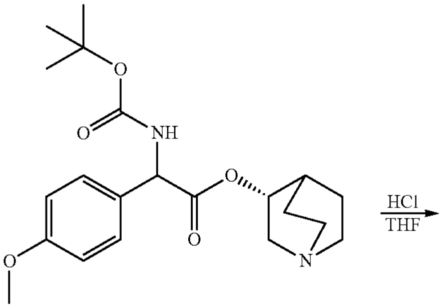
C44
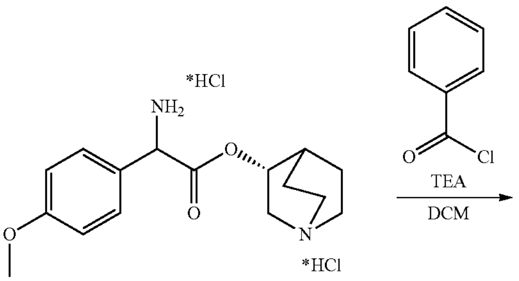
I106
-continued
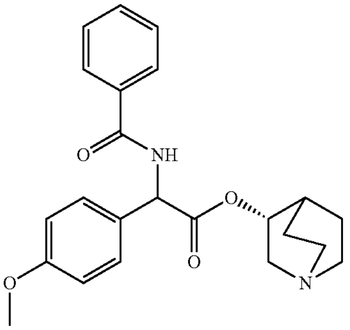
C107
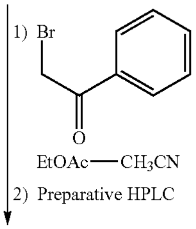

-continued

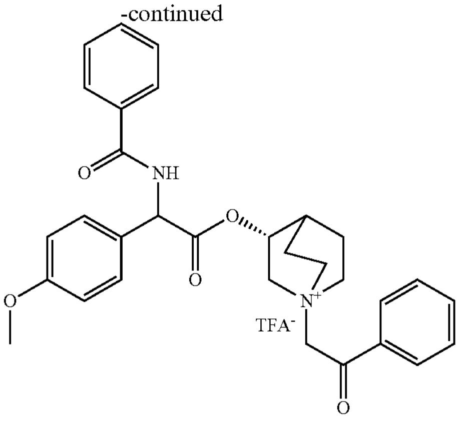

C108

Preparation of (R)-quinuclidin-3-yl 2-amino-2-(4-methoxyphenyl)acetate dihydrochloride (I106)

To a solution of (R)-quinuclidin-3-yl 2-(tert-butoxycarbonylamino)-2-(4-methoxyphenyl)acetate (C44) (560 mg, 1.43 mmol) in THF (20 ml), was added 37% hydrogen chloride (1.0 ml, 12.2 mmol). The reaction was stirred at RT for 15 hours. Then a second portion of 37% hydrogen chloride (1.0 ml, 12.2 mmol) was added, and the reaction was stirred at RT for additional 48 hours. The solvent was evaporated to obtain (R)-quinuclidin-3-yl 2-amino-2-(4-methoxyphenyl)acetate dihydrochloride (521 mg; quantitative yield).

Preparation of (R)-quinuclidin-3-yl 2-benzamido-2-(4-methoxyphenyl)acetate (C107)

To a suspension of (R)-quinuclidin-3-yl 2-amino-2-(4-methoxyphenyl)acetate dihydrochloride (I106) (325 mg, 0.89 mmol) in DCM (10 ml), were added triethylamine (374 μl, 2.68 mmol) and benzoyl chloride (125 μl, 1.07 mmol). The reaction was stirred at RT for 4 hours, and then the solvent was evaporated. The residue was taken up with EtOAc and washed with $Na_2CO_3$, water and brine. The organic phase was dried over $Na_2SO_4$, filtered and evaporated to obtain (R)-quinuclidin-3-yl 2-benzamido-2-(4-methoxyphenyl)acetate (145 mg; 41% yield). The product was used in the next step without any further purification.

Preparation of (3R)-3-(2-benzamido-2-(4-methoxyphenyl)acetoxy)-1-(2-oxo-2-phenylethyl)-1-azoniabicyclo[2.2.2]octane 2,2,2-trifluoroacetate (C108)

To a solution of (R)-quinuclidin-3-yl 2-benzamido-2-(4-methoxyphenyl)acetate (C107) (145 mg, 0.37 mmol) in EtOAc (2 ml) and acetonitrile (2 ml), was added 2-bromo-1-phenylethanone (80 mg, 0.40 mmol), and the reaction was stirred at RT for 15 hours. The solvent was evaporated, and the crude was purified by preparative HPLC to obtain (3R)-3-(2-benzamido-2-(4-methoxyphenyl)acetoxy)-1-(2-oxo-2-phenylethyl)-1-azoniabicyclo[2.2.2]octane 2,2,2-trifluoroacetate (52.4 mg; 23% yield).

$^1H$ NMR (300 MHz, DMSO-$d_6$) δ ppm 9.16 (d, 1H), 7.87-8.07 (m, 4H), 7.69-7.82 (m, 1H), 7.53-7.69 (m, 3H), 7.38-7.53 (m, 4H), 6.89-7.10 (m, 2H), 5.50-5.69 (m, 1H), 5.19-5.29 (m, 1H), 5.16 (s, 2H), 4.02-4.26 (m, 1H), 3.78 (s, 3H), 3.50-3.75 (m, 5H), 2.36-2.47 (m, 1H), 1.66-2.23 (m, 4H);

LC-MS (ESI POS): 513.12 (M+).

Example 41

Preparation of (3R)-3-(2-benzamido-2-p-tolylacetoxy)-1-(2-oxo-2-phenylethyl)-1-azoniabicyclo[2.2.2]octane 2,2,2-trifluoroacetate (C111)

Scheme 42

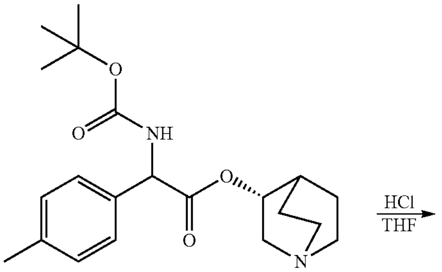

C41

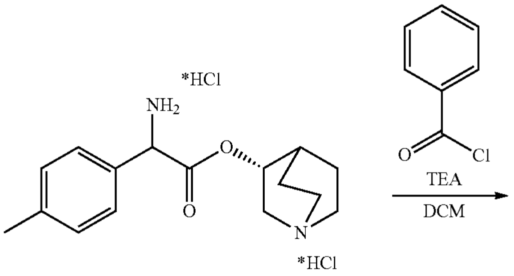

I109

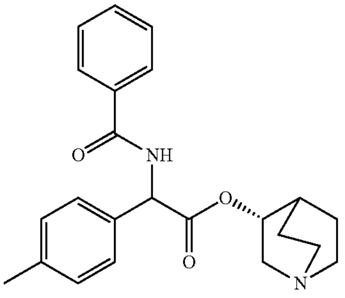

C110

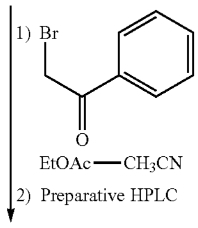

-continued

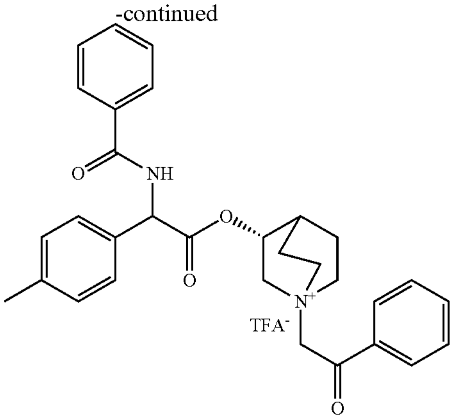

C111

Preparation of (R)-quinuclidin-3-yl 2-amino-2-p-tolylacetate dihydrochloride (I109)

To a solution of (R)-quinuclidin-3-yl 2-(tert-butoxycarbonylamino)-2-p-tolylacetate (C41) (250 mg, 0.67 mmol) in THF (50 ml), was added 37% hydrogen chloride (1.0 ml, 12.2 mmol), and the reaction was stirred at RT for 15 hours. The solvent was evaporated to obtain (R)-quinuclidin-3-yl 2-amino-2-p-tolylacetate dihydrochloride (232 mg; quantitative yield).

Preparation of (R)-quinuclidin-3-yl 2-benzamido-2-p-tolylacetate (C110)

To a suspension of (R)-quinuclidin-3-yl 2-amino-2-p-tolylacetate dihydrochloride (I109) (116 mg, 0.33 mmol) in DCM (5 ml), were added triethylamine (139 μl, 1.00 mmol) and benzoyl chloride (46.5 μl, 0.40 mmol). The reaction was stirred at RT for 3 hours, and then the solvent was evaporated. The residue was taken up with EtOAc and washed with $Na_2CO_3$, water and brine. The organic phase was dried over $Na_2SO_4$, filtered and evaporated to obtain (R)-quinuclidin-3-yl 2-benzamido-2-p-tolylacetate (70.0 mg; 55% yield). The product was used in the next step without any further purification.

Preparation of (3R)-3-(2-benzamido-2-p-tolylacetoxy)-1-(2-oxo-2-phenylethyl)-1-azoniabicyclo[2.2.2]octane 2,2,2-trifluoroacetate (C111)

2-Bromo-1-phenylethanone (40.5 mg, 0.20 mmol) was added to a solution of (R)-quinuclidin-3-yl 2-benzamido-2-p-tolylacetate (C110) (70.0 mg, 0.18 mmol) in EtOAc (3 ml). The reaction was stirred at RT for 15 hours, and then 2-bromo-1-phenylethanone (36.8 mg, 0.18 mmol) was added again and the reaction was stirred at RT for 6 hours. The solvent was evaporated and the crude was purified by preparative HPLC to obtain (3R)-3-(2-benzamido-2-p-tolylacetoxy)-1-(2-oxo-2-phenylethyl)-1-azoniabicyclo[2.2.2]octane 2,2,2-trifluoroacetate (54.8 mg; 48% yield).

$^1$H NMR (300 MHz, DMSO-$d_6$) δ ppm 9.19 and 9.20 (d, 1H), 7.86-8.05 (m, 4H), 7.71-7.84 (m, 1H), 7.52-7.71 (m, 3H), 7.39-7.52 (m, 4H), 7.17-7.33 (m, 2H), 5.65 and 5.69 (d, 1H), 5.21-5.31 (m, 1H), 5.16 and 5.18 (s, 2H), 4.00-4.26 (m, 1H), 3.38-3.89 (m, 5H), 2.19-2.27 and 2.38-2.46 (m, 1H), 2.33 (s, 3H), 1.48-2.17 (m, 4H);

LC-MS (ESI POS): 497.12 (M+).

Example 42

Preparation of (3R)-3-(2-benzamido-2-(4-chlorophenyl)acetoxy)-1-(2-oxo-2-phenylethyl)-1-azoniabicyclo[2.2.2]octane 2,2,2-trifluoroacetate (C114)

Scheme 43

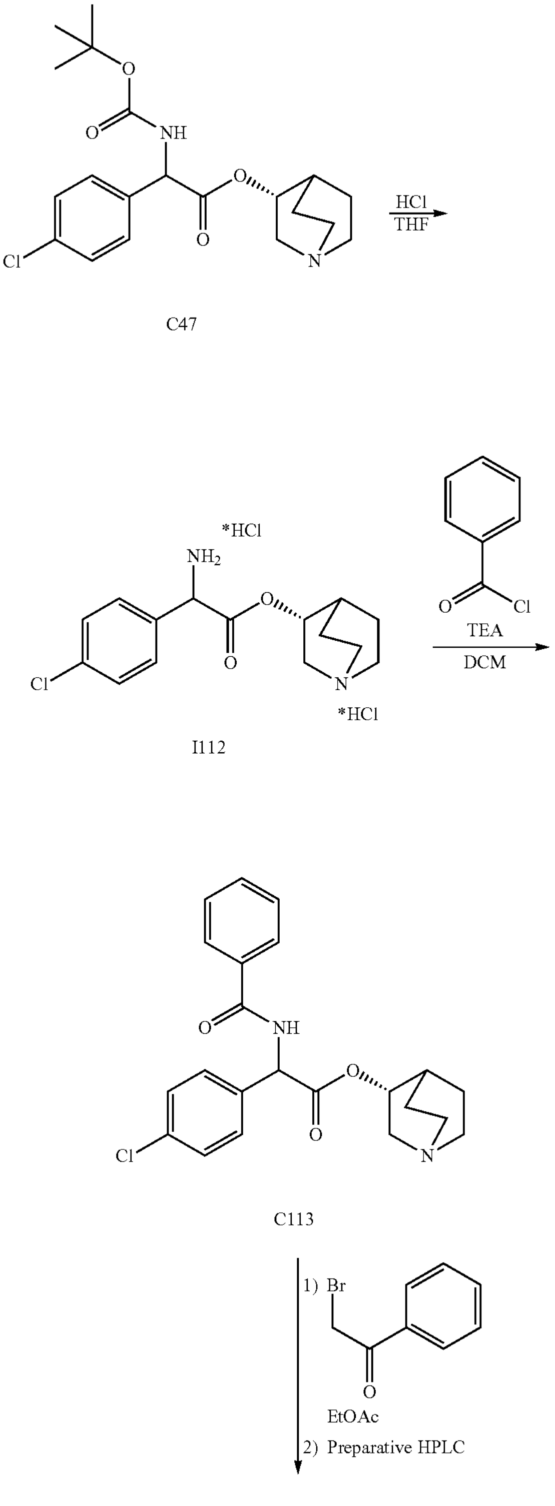

C47

I112

C113

-continued

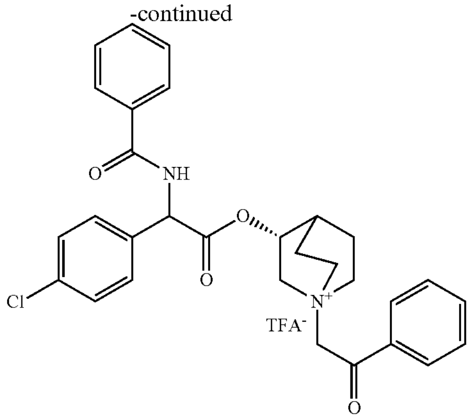

C114

Preparation of (R)-quinuclidin-3-yl 2-amino-2-(4-chlorophenyl)acetate dihydrochloride (I112)

To a solution of (R)-quinuclidin-3-yl 2-(tert-butoxycarbonylamino)-2-(4-chlorophenyl)acetate (C47) (250 mg, 0.63 mmol) in THF (5 ml), was added 37% hydrogen chloride (1.0 ml, 12.2 mmol). The reaction was stirred at RT for 15 hours. The solvent was evaporated to obtain (R)-quinuclidin-3-yl 2-amino-2-(4-chlorophenyl)acetate dihydrochloride (233 mg; quantitative yield).

Preparation of (R)-quinuclidin-3-yl 2-benzamido-2-(4-chlorophenyl)acetate (C113)

To a suspension of (R)-quinuclidin-3-yl 2-amino-2-(4-chlorophenyl)acetate dihydrochloride (I112) (0.12 g, 0.32 mmol) in DCM (5 ml), were added triethylamine (0.13 ml, 0.95 mmol) and benzoyl chloride (44.0 μl, 0.38 mmol), and the reaction was stirred at RT for 3 hours. Then the solvent was evaporated, and the residue was taken up with EtOAc and washed with $Na_2CO_3$, water and brine. The organic layer was dried over $Na_2SO_4$, filtered and evaporated to obtain (R)-quinuclidin-3-yl 2-benzamido-2-(4-chlorophenyl)acetate (0.126 g; quantitative yield).

Preparation of (3R)-3-(2-benzamido-2-(4-chlorophenyl)acetoxy)-1-(2-oxo-2-phenylethyl)-1-azoniabicyclo[2.2.2]octane 2,2,2-trifluoroacetate (C114)

To a solution of (R)-quinuclidin-3-yl 2-benzamido-2-(4-chlorophenyl)acetate (C113) (126 mg, 0.32 mmol) in EtOAc (3 ml), was added 2-bromo-1-phenylethanone (69.2 mg, 0.35 mmol). The reaction was stirred at RT for 15 hours, and then a second portion of 2-bromo-1-phenylethanone (62.9 mg, 0.32 mmol) was added, and the reaction was stirred for additional 6 hours. The solvent was evaporated and the crude was purified by preparative HPLC to obtain (3R)-3-(2-benzamido-2-(4-chlorophenyl)acetoxy)-1-(2-oxo-2-phenylethyl)-1-azoniabicyclo[2.2.2]octane 2,2,2-trifluoroacetate (46.0 mg; 23% yield).

$^1H$ NMR (300 MHz, DMSO-$d_6$) δ ppm 9.29 and 9.31 (d, 1H), 7.87-8.07 (m, 4H), 7.71-7.82 (m, 1H), 7.54-7.68 (m, 5H), 7.44-7.54 (m, 4H), 5.76 and 5.78 (d, 1H), 5.21-5.31 (m, 1H), 5.16 and 5.17 (br. s., 2H), 3.97-4.25 (m, 1H), 3.43-3.93 (m, 5H), 2.20-2.31 and 2.33-2.46 (m, 1H), 1.58-2.18 (m, 4H);

LC-MS (ESI POS): 517.12 (M+).

Example 43

Preparation of (3R)-3-(2-(tert-butoxycarbonylamino)-2-(thiophen-2-yl)acetoxy)-1-(2-oxo-2-phenylethyl)-1-azoniabicyclo[2.2.2]octane chloride (C116)

Scheme 44

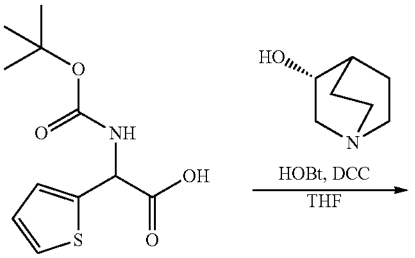

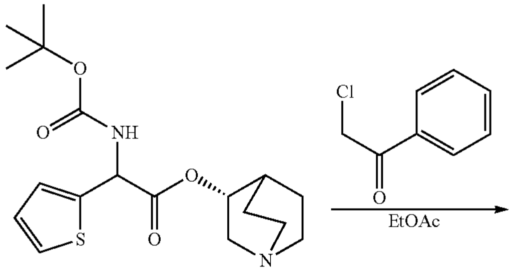

C115

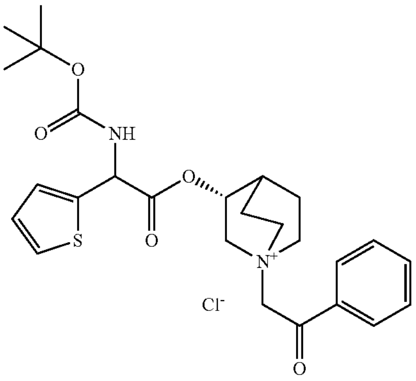

C116

Preparation of (R)-quinuclidin-3-yl 2-(tert-butoxycarbonylamino)-2-(thiophen-2-yl)acetate (C115)

A mixture of 2-(tert-butoxycarbonylamino)-2-(thiophen-2-yl)acetic acid (710 mg, 2.76 mmol), (R)-quinuclidin-3-ol (421 mg, 3.31 mmol), DCC (683 mg, 3.31 mmol), HOBT (507 mg, 3.31 mmol) in THF (20 ml) was stirred at RT overnight. THF was evaporated, and the crude was portioned between EtOAc and 1M $K_2CO_3$. The organic phase was dried over $Na_2SO_4$, filtered and evaporated to dryness. The crude was purified by flash chromatography (DCM/MeOH=98/2) to obtain (R)-quinuclidin-3-yl 2-(tert-butoxycarbonylamino)-2-(thiophen-2-yl)acetate (509 mg, 50.3% yield).

Preparation of (3R)-3-(2-(tert-butoxycarbonylamino)-2-(thiophen-2-yl)acetoxy)-1-(2-oxo-2-phenylethyl)-1-azoniabicyclo[2.2.2]octane chloride (C116)

2-Chloro-1-phenylethanone (43.0 mg, 0.28 mmol) was added to a solution of (R)-quinuclidin-3-yl 2-(tert-butoxycarbonylamino)-2-(thiophen-2-yl)acetate (102 mg, 0.28 mmol) in EtOAc (3 ml). The reaction was stirred at RT for 20 hours. The solvent was evaporated, and the crude was triturated with $Et_2O$ (2 ml) and dried under vacuum to obtain (3R)-3-(2-(tert-butoxycarbonylamino)-2-(thiophen-2-yl)acetoxy)-1-(2-oxo-2-phenylethyl)-1-azoniabicyclo[2.2.2]octane chloride (70 mg, 48.3% yield).

$^1$H NMR (300 MHz, DMSO-d6) δ ppm 8.02-8.07 (m, 1H), 7.87-8.02 (m, 2H), 7.68-7.84 (m, 1H), 7.56-7.68 (m, 2H), 7.52 (dd, 1H), 7.12-7.26 (m, 1H), 7.03 (dd, 1H), 5.42-5.65 (m, 1H), 5.17-5.33 (m, 1H), 5.21 (s, 2H), 4.07-4.29 (m, 1H), 3.47-3.85 (m, 5H), 2.21-2.33 and 2.35-2.45 (m, 1H), 1.97-2.19 (m, 2H), 1.66-1.97 (m, 2H), 1.42 (s, 9H);

LC-MS (ESI POS): 485.09 (M+).

Example 44

Preparation of (3R)-3-(2-(tert-butoxycarbonylamino)-3-(1H-indol-3-yl)propanoyloxy)-1-(2-oxo-2-phenylethyl)-1-azoniabicyclo[2.2.2]octane bromide (C118)

Scheme 45

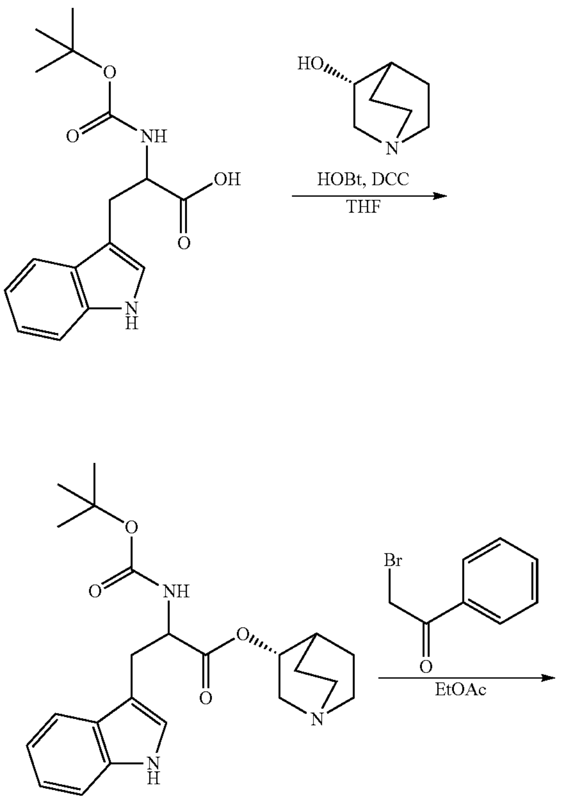

C117

-continued

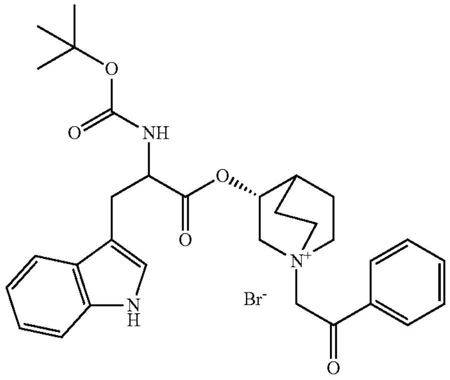

C118

Preparation of (R)-quinuclidin-3-yl 2-(tert-butoxycarbonylamino)-3-(1H-indol-3-yl)propanoate (C117)

A solution of 2-(tert-butoxycarbonylamino)-3-(1H-indol-3-yl)propanoic acid (100 mg, 0.33 mmol), (R)-quinuclidin-3-ol (50.1 mg, 0.39 mmol), HOBT (53.3 mg, 0.39 mmol) and EDC (76 mg, 0.39 mmol) in DMF (2 ml) was heated at 90° C. for 1.5 hours under microwave irradiation. The solvent was evaporated. The residue was taken up with EtOAc and washed with 1N $Na_2CO_3$, water and brine. The organic phase was dried over $Na_2SO_4$, filtered and evaporated to obtain (R)-quinuclidin-3-yl 2-(tert-butoxycarbonylamino)-3-(1H-indol-3-yl)propanoate (95 mg, 69.9% yield), which was used as such in the next step.

Preparation of (3R)-3-(2-(tert-butoxycarbonylamino)-3-(1H-indol-3-yl)propanoyloxy)-1-(2-oxo-2-phenylethyl)-1-azoniabicyclo[2.2.2]octane bromide (C118)

To a solution of (R)-quinuclidin-3-yl 2-(tert-butoxycarbonylamino)-3-(1H-indol-3-yl)propanoate (95 mg, 0.23 mmol) in EtOAc (3 ml), was added 2-bromo-1-phenylethanone (54.9 mg, 0.28 mmol), and the reaction was stirred at RT for 15 hours. The solid was collected by filtration and purified by silica gel flash chromatography (DCM/MeOH=94/6) to obtain (3R)-3-(2-(tert-butoxycarbonylamino)-3-(1H-indol-3-yl)propanoyloxy)-1-(2-oxo-2-phenylethyl)-1-azoniabicyclo[2.2.2]octane bromide (31.0 mg, 22% yield).

$^1$H NMR (300 MHz, DMSO-d6) δ ppm 10.87 (br. s., 1H), 7.93-8.05 (m, 2H), 7.70-7.81 (m, 1H), 7.58-7.69 (m, 2H), 7.53 (d, 1H), 7.28-7.41 (m, 2H), 7.17-7.25 (m, 1H), 7.04-7.14 (m, 1H), 6.96-7.04 (m, 1H), 5.10 and 5.16 (s, 2H), 4.98-5.15 (m, 1H), 4.23-4.39 (m, 1H), 3.98-4.23 (m, 1H), 3.46-3.85 (m, 5H), 3.01-3.24 (m, 2H), 1.66-2.16 (m, 5H), 1.26 and 1.36 (s, 9H);

LC-MS (ESI POS): 532.32 (M+).

Example 45

Preparation of ((R)-3-((S)-3-(4-(benzyloxy)phenyl)-2-(tert-butoxycarbonylamino)propanoyloxy)-1-(2-oxo-2-phenylethyl)-1-azoniabicyclo[2.2.2]octane bromide (Diastereomer 1 of C120)

Scheme 46

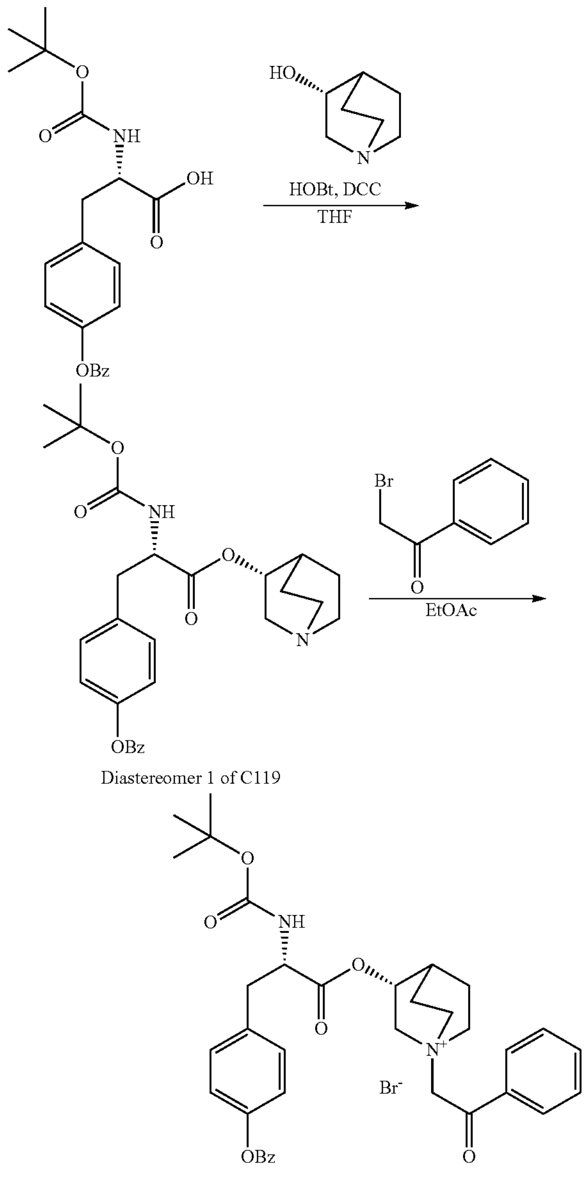

Diastereomer 1 of C119

Diastereomer 1 of C120

Bz stands for benzyl group

Preparation of (S)—((R)-quinuclidin-3-yl) 3-(4-(benzyloxy)phenyl)-2-(tert-butoxycarbonylamino) propanoate (Diastereomer 1 of C119)

A mixture of (S)-3-(4-(benzyloxy)phenyl)-2-(tert-butoxycarbonyl-amino)propanoic acid (500 mg, 1.35 mmol), DCC (333 mg, 1.61 mmol) and HOBT (247 mg, 1.61 mmol) in dry THF (10 ml) was stirred at RT under nitrogen atmosphere for 1 hour. (R)-quinuclidin-3-ol (205 mg, 1.61 mmol) was added, and the reaction was stirred for 16 hours. The solvent was evaporated, and the residue was portioned between saturated $NaHCO_3$ and EtOAc. The organic phase was washed with brine, dried over $Na_2SO_4$ filtered and evaporated to dryness. The residue was triturated with $Et_2O$ (30 ml), and the insoluble material was removed by filtration. The solution was evaporated to obtain (S)—((R)-quinuclidin-3-yl) 3-(4-(benzyloxy)phenyl)-2-(tert-butoxycarbonylamino)-propanoate (590 mg, 91% yield).

Preparation of (R)-3-((S)-3-(4-(benzyloxy)phenyl)-2-(tert-butoxycarbonylamino)-propanoyloxy)-1-(2-oxo-2-phenylethyl)-1-azoniabicyclo[2.2.2]octane bromide (Diastereomer 1 of C120)

To a solution of (S)—((R)-quinuclidin-3-yl) 3-(4-(benzyloxy)phenyl)-2-(tert-butoxycarbonylamino)propanoate (590 mg, 1.23 mmol) in EtOAc (15 ml), was added portionwise 2-bromo-1-phenylethanone (232 mg, 1.17 mmol). The reaction was stirred at RT for 16 hours. The solvent was evaporated, and the residue was triturated with $Et_2O$, filtered and dried under vacuum to obtain (R)-3-((S)-3-(4-(benzyloxy) phenyl)-2-(tert-butoxycarbonylamino)propanoyloxy)-1-(2-oxo-2-phenylethyl)-1-azoniabicyclo[2.2.2]octane bromide (720 mg, 86% yield).

$^1H$ NMR (300 MHz, DMSO-d6) δ ppm 7.88-8.11 (m, 2H), 7.70-7.84 (m, 1H), 7.56-7.69 (m, 2H), 7.26-7.50 (m, 6H), 7.18 (m, 2H), 6.94 (m, 2H), 5.19 (s, 2H), 5.15-5.26 (m, 1H), 5.07 (s, 2H), 4.06-4.32 (m, 2H), 3.50-3.83 (m, 5H), 2.79-3.09 (m, 2H), 2.19 (br. s., 1H), 1.96-2.13 (m, 2H), 1.74-1.96 (m, 2H), 1.35 (s, 9H);

LC-MS (ESI POS): 599.37 (M+);

$[\alpha]_D$=−22.52 (c=0.5, MeOH).

Example 46

Preparation of (R)-3-((S)-2-(tert-butoxycarbonylamino)-3-(4-hydroxyphenyl)propanoyloxy)-1-(2-oxo-2-phenylethyl)-1-azoniabicyclo[2.2.2]octane bromide (Diastereomer 1 of C122)

Scheme 47

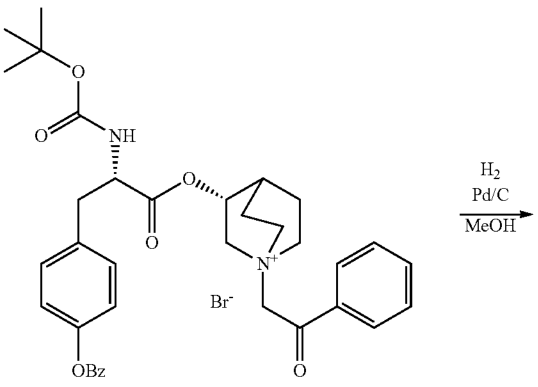

Diastereomer 1 of C120

-continued

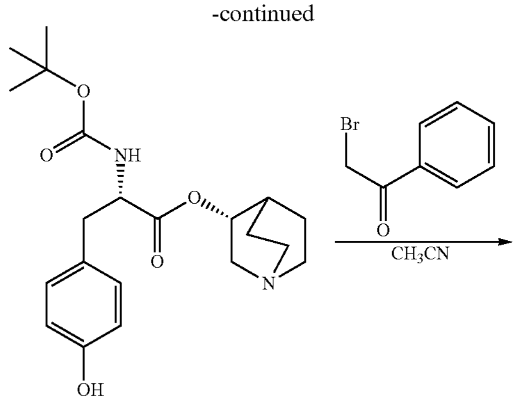

Diastereomer 1 of C121

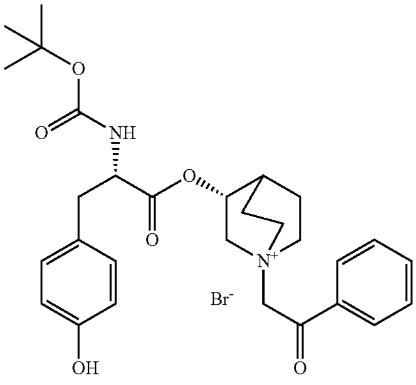

Diastereomer 1 of C122

Preparation of (S)—((R)-quinuclidin-3-yl) 2-(tert-butoxycarbonylamino)-3-(4-hydroxyphenyl)propanoate (Diastereomer 1 of C121)

A mixture of (R)-3-((S)-3-(4-(benzyloxy)phenyl)-2-(tert-butoxycarbonylamino)-propanoyloxy)-1-(2-oxo-2-phenylethyl)-1-azoniabicyclo[2.2.2]octane bromide (720 mg, 1.06 mmol) and 10% Pd/C (100 mg, 0.09 mmol) in MeOH (30 ml) was hydrogenated at 25 psi for 2 hours. The catalyst was removed by filtration, and the solvent was evaporated to dryness. The residue was dissolved in DCM and filtered through a SCX cartridge. The solution was evaporated to obtain (S)—((R)-quinuclidin-3-yl) 2-(tert-butoxycarbonylamino)-3-(4-hydroxyphenyl)propanoate (260 mg, 62.9% yield).

Preparation of (R)-3-((S)-2-(tert-butoxycarbonylamino)-3-(4-hydroxyphenyl)-propanoyloxy)-1-(2-oxo-2-phenylethyl)-1-azoniabicyclo[2.2.2]octane bromide (Diastereomer 1 of C122)

To a solution of (S)—((R)-quinuclidin-3-yl) 2-(tert-butoxycarbonylamino)-3-(4-hydroxyphenyl)propanoate (260 mg, 0.67 mmol) in dry acetonitrile (10 ml), was added portionwise 2-bromo-1-phenylethanone (126 mg, 0.63 mmol). The reaction was stirred at RT for 3 hours. The solvent was evaporated, and the residue was purified by flash chromatography (DCM/MeOH=85/15), and the recovered product was triturated with i-PrOH to obtain (R)-3-((S)-2-(tert-butoxycarbonylamino)-3-(4-hydroxyphenyl)-propanoyloxy)-1-(2-oxo-2-phenylethyl)-1-azoniabicyclo[2.2.2]octane bromide (74 mg, 18.8% yield).

$^1$H NMR (300 MHz, DMSO-d6) δ ppm 9.22 (s, 1H), 7.85-8.05 (m, 2H), 7.76 (t, 1H), 7.62 (t, 2H), 7.33 (d, 1H), 7.05 (m, 2H), 6.69 (m, 2H), 5.20 (s, 2H), 4.31 (d, 1H), 4.01-4.25 (m, 2H), 3.47-3.78 (m, 5H), 2.75-3.02 (m, 2H), 2.20 (br. s., 1H), 1.76-2.13 (m, 4H), 1.36 (s, 9H);

LC-MS (ESI POS): 509.33 (M+);

$[\alpha]_D$=−15.48 (c=0.5, MeOH).

Example 47

Preparation of (R)-3-((S)-2-(tert-butoxycarbonylamino)-3-phenylpropanoyloxy)-1-(2-oxo-2-phenylethyl)-1-azoniabicyclo[2.2.2]octane bromide (Diastereomer 1 of C124)

Scheme 48

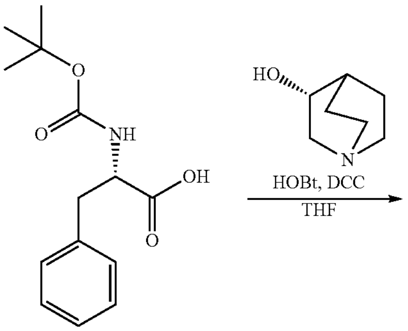

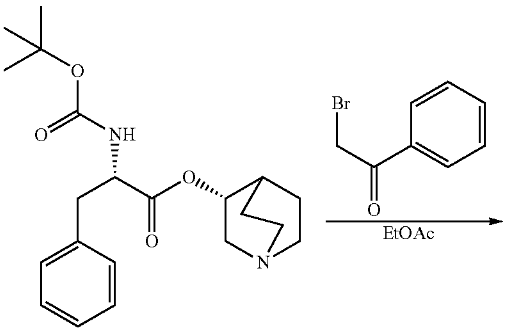

Diastereomer 1 of C123

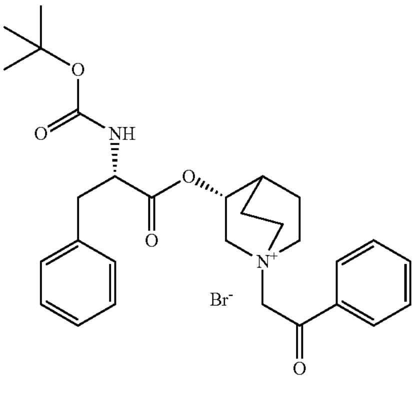

Diastereomer 1 of C124

Preparation of (S)—((R)-quinuclidin-3-yl) 2-(tert-butoxycarbonylamino)-3-phenylpropanoate (Diastereomer 1 of C123)

A mixture of (S)-2-(tert-butoxycarbonylamino)-3-phenylpropanoic acid (500 mg, 1.88 mmol), DCC (467 mg, 2.26 mmol), and HOBT (346 mg, 2.26 mmol) in dry THF (15 ml) was stirred for 30 minutes at RT. Then (R)-quinuclidin-3-ol (288 mg, 2.26 mmol) was added portionwise and the reaction was stirred at RT for 16 hours. The solvent was evaporated, the residue was dissolved in EtOAc, and the insoluble was removed by filtration. The organic phase was washed with saturated $NaHCO_3$ and brine, dried over $Na_2SO_4$, filtered and evaporated to obtain (S)—((R)-quinuclidin-3-yl) 2-(tert-butoxycarbonylamino)-3-phenylpropanoate (600 mg, 85% yield).

Preparation of (R)-3-((S)-2-(tert-butoxycarbonylamino)-3-phenylpropanoyloxy)-1-(2-oxo-2-phenylethyl)-1-azoniabicyclo[2.2.2]octane bromide (Diastereomer 1 of C124)

To a solution of (S)—((R)-quinuclidin-3-yl) 2-(tert-butoxycarbonylamino)-3-phenylpropanoate (600 mg, 1.60 mmol) in EtOAc (10 ml), was added portionwise 2-bromo-1-phenylethanone (303 mg, 1.52 mmol). The reaction was stirred at RT for three days. The precipitate was collected by filtration and dried under vacuum to obtain (R)-3-((S)-2-(tert-butoxycarbonylamino)-3-phenylpropanoyloxy)-1-(2-oxo-2-phenylethyl)-1-azoniabicyclo[2.2.2]octane bromide (740 mg, 81% yield).

$^1H$ NMR (300 MHz, DMSO-d6) δ ppm 7.94-8.05 (m, 2H), 7.69-7.81 (m, 1H), 7.54-7.69 (m, 2H), 7.41 (m, 1H), 7.17-7.36 (m, 5H), 5.20 (s, 2H), 5.07-5.31 (m, 1H), 4.21-4.38 (m, 1H), 4.15 (dd, 1H), 3.48-3.86 (m, 5H), 2.77-3.13 (m, 2H), 2.15-2.25 (m, 1H), 1.99-2.15 (m, 2H), 1.75-1.99 (m, 2H), 1.35 (s, 9H);

LC-MS (ESI POS): 493.45 (M+);

$[\alpha]_D$=−19.72 (c=0.5, MeOH).

Example 48

Preparation of (3R)-3-(2-(2-amino-2-phenylacetamido)-2-phenylacetoxy)-1-(2-oxo-2-phenylethyl)-1-azoniabicyclo[2.2.2]octane 2,2,2-trifluoroacetate 2,2,2-trifluoroacetic acid (C127)

Scheme 49

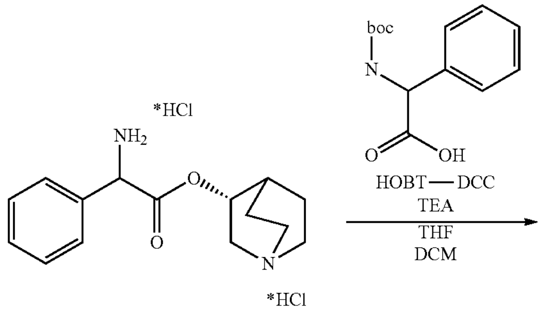

I25

-continued

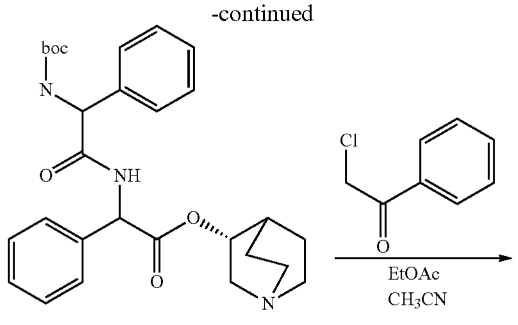

C125

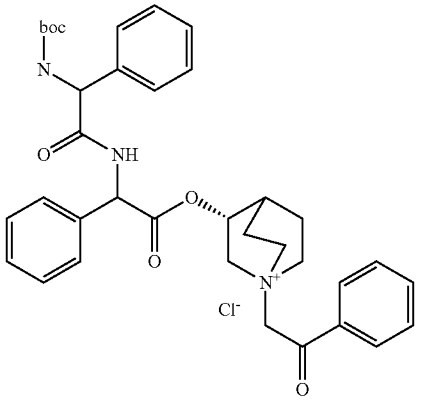

C126

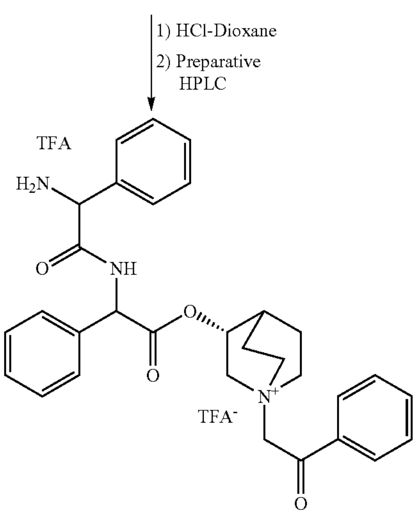

C127

Preparation of (R)-quinuclidin-3-yl 2-(2-(tert-butoxycarbonylamino)-2-phenylacetamido)-2-phenylacetate (C125)

To a suspension of (R)-quinuclidin-3-yl 2-amino-2-phenylacetate dihydrochloride (500 mg, 1.50 mmol) in THF (15 ml) and DCM (5 ml), was added triethylamine (591 μl, 4.25 mmol), and the reaction was stirred at RT for 10 minutes. Then DCC (309 mg, 1.50 mmol), HOBT (203 mg, 1.50 mmol), and 2-(tert-butoxycarbonylamino)-2-phenylacetic acid (314 mg, 1.25 mmol) were added, and the reaction was stirred at RT for 15 hours. The solvent was evaporated, the residue was taken up with DCM, and the insoluble was removed by filtration. The organic solution was washed twice with 1N $Na_2CO_3$ and brine, dried over $Na_2SO_4$ and evaporated. The crude was purified by flash chromatography (DCM/MeOH=95/5) to obtain (R)-quinuclidin-3-yl 2-(2-(tert-butoxycarbonylamino)-2-phenylacetamido)-2-phenylacetate (210 mg, 34% yield).

Preparation of (3R)-3-(2-(2-(tert-butoxycarbonylamino)-2-phenylacetamido)-2-phenylacetoxy)-1-(2-oxo-2-phenylethyl)-1-azoniabicyclo[2.2.2]octane chloride (C126)

To a solution of (R)-quinuclidin-3-yl 2-(2-(tert-butoxycarbonylamino)-2-phenylacetamido)-2-phenylacetate (210 mg, 0.42 mmol) in EtOAc (3 ml) and acetonitrile (3 ml), was added 2-chloro-1-phenylethanone (65.8 mg, 0.42 mmol), and the reaction was stirred at RT for 15 hours. More 2-chloro-1-phenylethanone (19.7 mg, 0.13 mmol) was added, and the reaction was stirred at RT for 24 hours. The solvent was evaporated, and the crude was purified by flash chromatography (DCM/MeOH=94/6 to 93/7) to obtain (3R)-3-(2-(2-(tert-butoxycarbonylamino)-2-phenylacetamido)-2-phenylacetoxy)-1-(2-oxo-2-phenylethyl)-1-azoniabicyclo[2.2.2]octane chloride (65.3 mg, 23.7% yield).

Preparation of (3R)-3-(2-(2-amino-2-phenylacetamido)-2-phenylacetoxy)-1-(2-oxo-2-phenylethyl)-1-azoniabicyclo[2.2.2]octane 2,2,2-trifluoroacetate 2,2,2-trifluoroacetic acid (C127)

To a solution cooled to 0° C. of (3R)-3-(2-(2-(tert-butoxycarbonylamino)-2-phenylacetamido)-2-phenylacetoxy)-1-(2-oxo-2-phenylethyl)-1-azoniabicyclo[2.2.2]octane chloride (50 mg, 0.08 mmol) in dioxane (4 ml), was added hydrogen chloride (4M solution in dioxane, 23 μl), and the reaction was stirred at RT for hours. Additional hydrogen chloride (4M solution in dioxane, 193 μl) was added, and the reaction was stirred at RT for 7 hours. Then 37% hydrogen chloride (0.5 ml, 6.09 mmol) was added, and the reaction was stirred at RT for 20 hours. The solvent was evaporated, and the resulting crude was purified by preparative HPLC to obtain (3R)-3-(2-(2-amino-2-phenylacetamido)-2-phenylacetoxy)-1-(2-oxo-2-phenylethyl)-1-azoniabicyclo[2.2.2]octane 2,2,2-trifluoroacetate 2,2,2-trifluoroacetic acid (14.8 mg, 25.9% yield).

$^1H$ NMR (300 MHz, DMSO-d6) δ 8.95-9.30 (m, 1H), 7.86-8.11 (m, 2H), 7.69-7.86 (m, 1H), 7.52-7.69 (m, 2H), 7.22-7.50 (m, 11H), 5.30-5.57 (m, 2H), 5.00-5.30 (m, 3H), 4.03-4.17 (m, 1H), 3.43-3.78 (m, 5H), 2.14-2.22 and 2.32-2.45 (m, 1H), 1.88-2.13 (m, 2H), 1.71-1.88 (m, 1H), 1.50-1.71 (m, 1H), 1.36 and 1.38 (s, 9H);

LC-MS (ESI POS): 612.53 (M+).

Example 49

Preparation of (3R)-3-(2-benzamido-3-methylbutanoyloxy)-1-(2-oxo-2-phenylethyl)-1-azoniabicyclo[2.2.2]octane 2,2,2-trifluoroacetate (C130)

Scheme 50

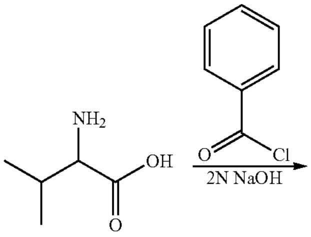

-continued

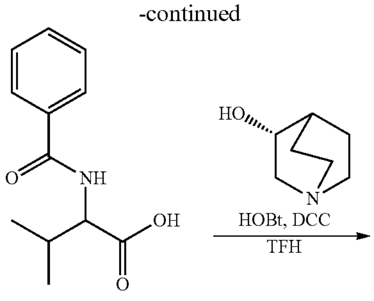

C128

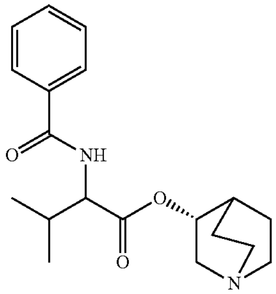

C129

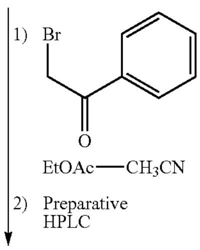

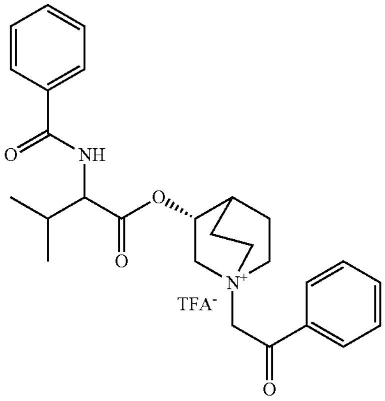

C130

Preparation of 2-benzamido-3-methylbutanoic acid (C128)

A solution of 2-amino-3-methylbutanoic acid (500 mg, 4.27 mmol) in 2N NaOH (2.35 ml, 4.69 mmol) was stirred at RT for 30 minutes, then the reaction mixture was cooled at 0° C., and benzoyl chloride (471 μl, 4.05 mmol) and 2N NaOH (2.35 ml, 4.69 mmol) were simultaneously added dropwise from two different syringes. The reaction was stirred at RT for 3 hours. Water was added, the aqueous phase was washed with $Et_2O$, then acidified with 1M HCl and back-extracted with $Et_2O$, dried over $Na_2SO_4$ and evaporated. The residue was triturated with i-$Pr_2O$ to obtain 2-benzamido-3-methylbutanoic acid (780 mg, 83% yield).

Preparation of (R)-quinuclidin-3-yl 2-benzamido-3-methylbutanoate (C129)

To a solution of 2-benzamido-3-methylbutanoic acid (780 mg, 3.53 mmol) in THF (25 ml), were added (R)-quinuclidin-3-ol (538 mg, 4.23 mmol), DCC (873 mg, 4.23 mmol) and HOBt (572 mg, 4.23 mmol), and the reaction was stirred at RT for 15 hours. The solvent was evaporated. EtOAc was added, and the insoluble was removed by filtration. The organic solution was washed twice with 1N $Na_2CO_3$ and brine, dried over $Na_2SO_4$ and evaporated to dryness. The crude was purified by flash chromatography (DCM/MeOH=99/1 to 8/2) to obtain (R)-quinuclidin-3-yl 2-benzamido-3-methylbutanoate (436 mg, 37.4% yield).

Preparation of (3R)-3-(2-benzamido-3-methylbutanoyloxy)-1-(2-oxo-2-phenylethyl)-1-azoniabicyclo[2.2.2]octane 2,2,2-trifluoroacetate (C130)

To a solution of (R)-quinuclidin-3-yl 2-benzamido-3-methylbutanoate (218 mg, 0.66 mmol) in EtOAc (2 ml) and acetonitrile (5 ml), was added 2-bromo-1-phenylethanone (158 mg, 0.79 mmol) and the reaction was stirred at RT for 15 hours. The solvent was evaporated, and the residue was triturated with acetonitrile. The crude was purified by preparative HPLC to obtain (3R)-3-(2-benzamido-3-methylbutanoyloxy)-1-(2-oxo-2-phenylethyl)-1-azoniabicyclo[2.2.2]octane 2,2,2-trifluoroacetate (15.5 mg, 4.2% yield)

$^1H$ NMR (300 MHz, DMSO-d6) δ 8.64 and 8.66 (d, 1H), 7.94-8.05 (m, 2H), 7.83-7.94 (m, 2H), 7.69-7.81 (m, 1H), 7.41-7.66 (m, 5H), 5.22-5.32 (m, 1H), 5.18 and 5.20 (s, 2H), 4.26-4.45 (m, 1H), 4.07-4.24 (m, 1H), 3.53-3.85 (m, 5H), 1.79-2.44 (m, 6H), 1.06 (d, 3H), 1.04 (d, 3H);

LC-MS (ESI POS): 449.24 (M+).

Example 50

Preparation of (3R)-3-(2-benzamido-3-methylbutanoyloxy)-1-(2-oxo-2-(thiophen-2-yl)ethyl)-1-azoniabicyclo[2.2.2]octane 2,2,2-trifluoroacetate (C131)

Scheme 51

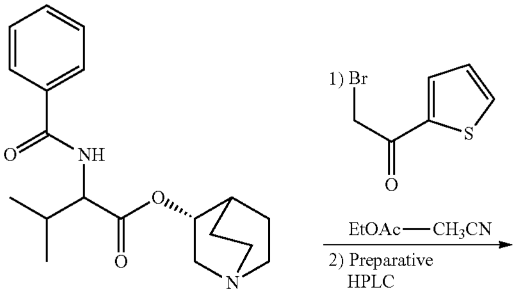

C129

-continued

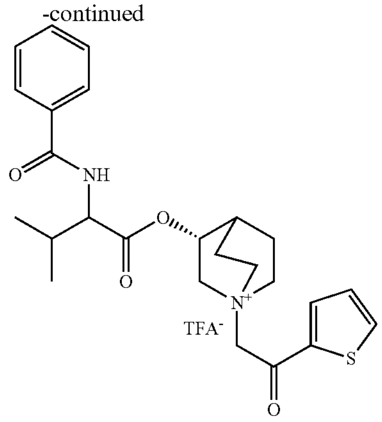

C131

To a solution of (R)-quinuclidin-3-yl 2-benzamido-3-methylbutanoate (218 mg, 0.66 mmol) in EtOAc (2 ml) and $CH_3CN$ (5 ml), was added 2-bromo-1-(thiophen-2-yl)ethanone (162 mg, 0.79 mmol), and the reaction was stirred at RT for 15 hours. The solvent was evaporated, and the crude was purified by flash chromatography (DCM/MeOH=98/2 to 85/15).

The product was triturated with i-$Pr_2O$ and further purified by preparative HPLC to obtain (3R)-3-(2-benzamido-3-methylbutanoyloxy)-1-(2-oxo-2-(thiophen-2-yl)ethyl)-1-azoniabicyclo[2.2.2]octane 2,2,2-trifluoroacetate (30.6 mg, 8.2% yield).

$^1H$ NMR (300 MHz, DMSO-d6) δ 8.66 (d, 1H), 8.21 (dd, 1H), 8.07 (dd, 1H), 7.82-7.94 (m, 2H), 7.53-7.63 (m, 1H), 7.43-7.53 (m, 2H), 7.31-7.39 (m, 1H), 5.18-5.31 (m, 1H), 4.93-5.17 (m, 2H), 4.32 and 4.39 (t, 1H), 4.08-4.23 (m, 1H), 3.58-3.86 (m, 5H), 1.72-2.43 (m, 6H), 0.93-1.16 (m, 6H);

LC-MS (ESI POS): 455.26 (M+).

Biological Characterisation.

Example 51

Examples of Radioligand Binding Assay for Cloned Human Muscarinic Receptors and for Human Beta Adrenergic Receptors CHO-K1 clone cells expressing the human M1-, M2-, M3-receptors (Euroscreen, Swissprot P11229, P08172, P20309, Genbank: J02960 respectively) were harvested in $Ca^{++}/Mg^{++}$ free phosphate-buffered saline and collected by centrifugation at 1500 rpm for 10 min, at 4° C. minutes. The pellets were resuspended in ice cold buffer A (15 mM Tris-HCl pH 7.4, 2 mM $MgCl_2$, 0.3 mM EDTA, 1 mM EGTA). Cloned cells expressing M1-, M2-, and M3-receptors were homogenized by a PBI politron (setting 5 for 15 seconds). The crude membrane fraction was collected by two consecutive centrifugation steps at 40000 g for 20 minutes at 4° C., separated by a washing step in buffer A.

The pellets obtained from the three cell lines were finally resuspended in buffer C (75 mM Tris HCl pH 7.4, 12.5 mM $MgCl_2$, 0.3 mM EDTA, 1 mM EGTA, 250 mM sucrose) and aliquots were stored at −80° C.

The day of experiment, M1-, M2-, and M3-receptor frozen membranes were resuspended in buffer D (50 mM Tris-HCl pH 7.4, 2.5 mM $MgCl_2$, 1 mM EDTA). The non-selective muscarinic radioligand [3H]-N-methyl scopolamine (*Mol. Pharmacol.,* 45:899-907, which is incorporated herein by reference in its entirety) was used to label the M1, M2, and M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 mL) were incubated at RT for 120 minutes for M1, 60 minutes for M2 and 90 minutes for M3 binding assay.

The reaction was terminated by rapid filtration through GF/B Unifilter plates and two washes (0.75 mL) with cold buffer using a Packard Filtermate Harvester. Radioactivity on the filters was measured by a microplate scintillation counter TopCount NXT (Canberra Packard).

In the present assays, Ki values for the tested compounds were determined from the observed IC50 values according to known methods. A lower Ki value indicates that the tested compound has a higher binding affinity for the receptor.

The Ki M2/Ki M3 ratio for representative compounds of general formula (I) in Scheme 1, are comprised between 30 and 157.

The interaction with M3 muscarinic receptors can be estimated by the results of in vitro studies which evaluated the potency of the test compounds and the offset of the inhibitory activity produced after washout of the antagonists in isolated guinea pig trachea and by the in vivo duration of action against acetylcholine-induced bronchospasm in the guinea pig.

Example 52

Plasma Stability

In order to demonstrate that the compounds are degraded, stability in human plasma at 1 and 5 hours was tested for the compound of the invention. Briefly 10 μl of a stock solution 250 μM of the compound in acetonitrile were added to 1 ml of human plasma, and samples were incubated at 37° C. Plasma (50 μL) was taken after 0, 1, and 5 hours of incubation and added to 140 μl of acetonitrile with addition of verapamil as internal standard (250 ng/ml). Samples were analysed by HPLC-MS/MS analysis.

Plasma stability is calculated as percentage remaining after 1 and 5 hours by dividing the peak area at 1 or 5 hours by the area of the peak at time 0.

After 5 hours of incubation, plasma stability values for representative compounds of general formula (I) in Scheme 1 are comprised between 0.6 and 13.1%, indicating that the compounds of the invention are very unstable in human plasma.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

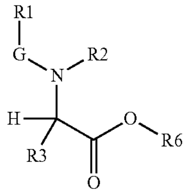

(I)

wherein:

R1 is —H, or linear or branched ($C_1$-$C_{10}$)alkyl, ($C_2$-$C_6$) alkenyl, aryl, ($C_3$-$C_8$)cycloalkyl, ($C_5$-$C_{10}$)heterocycloalkyl, aryl($C_1$-$C_6$)alkyl, or heteroaryl, each of which may be optionally substituted by one or more substituents selected from the group consisting of a halogen atom, —OH, oxo (=O), —SH, —$NO_2$, —N(R5)(R8), —CN, —CON$(R5)_2$, —NHCO(R5), —COR5, —$CO_2$R5, ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$) alkylcarboxyl, ($C_1$-$C_{10}$)alkoxy, aryl, aryloxy, and heteroaryl;

G is —OC(O)—, —$SO_2$—, or —C(O)—;

R2 is —H or ($C_1$-$C_{10}$)alkyl or aryl($C_1$-$C_6$)alkyl, each of which may be optionally substituted by one or more substituents selected from the group consisting of a halogen atom, —OH, oxo (=O), —SH, —$NO_2$, —N$(R5)_2$, —CN, —CON$(R5)_2$, —NHCO(R5), —CO(R5), —$CO_2$(R5), ($C_1$-$C_{10}$)alkylsulfanyl, ($C_1$-$C_{10}$) alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, and heteroaryl;

R3 is —H or ($C_1$-$C_{10}$)alkyl, aryl, ($C_3$-$C_8$)cycloalkyl, heteroaryl, aryl($C_1$-$C_6$)alkyl, or heteroaryl($C_1$-$C_6$)alkyl, each of which may be optionally substituted by one or more substituents selected from the group consisting of a halogen atom, —OH, oxo (=O), —SH, —$NO_2$, —N$(R5)_2$, —CN, —CON$(R5)_2$, —NHCO(R5), —CO(R5), —$CO_2$(R5), ($C_1$-$C_{10}$)alkylsulfanyl, ($C_1$-$C_{10}$) alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, aryl($C_1$-$C_{10}$)alkylenoxy, and heteroaryl;

R6 is a group of formula (i):

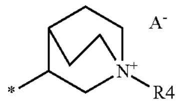

(i)

wherein $A^-$ is a physiologically acceptable anion;

R4 is a group of formula (Y):

$$—(CH_2)p\text{-}P—(CH_2)q\text{-}W \quad (Y)$$

wherein p is 0 or an integer from 1 to 4;

q is 0 or an integer from 1 to 4;

P is absent or is —O—, —S—, —SO—, —$SO_2$—, —C(O)—, —N(R5)-, —CH=CH—, —N(R5)($SO_2$)—, —N(R5)(COO)—, —N(R5)(C(O))—, —S($O_2$)N(R5)-, —CO(O)N(R5)-, or —C(O)N(R5)-;

W is —H, or linear or branched ($C_1$-$C_{10}$)alkyl, ($C_2$-$C_6$) alkenyl, aryl, ($C_3$-$C_8$)cycloalkyl, ($C_5$-$C_{10}$)heterocycloalkyl, aryl($C_1$-$C_6$)alkyl, or heteroaryl, each of which may be optionally substituted by one or more substituents selected from the group consisting of a halogen atom, —OH, oxo (═O), —SH, —$NO_2$, —N$(R5)_2$, —CN, —CON$(R5)_2$, —NH(COR5), —CO(R5), —$CO_2$(R5), ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$)alkylcarboxyl, ($C_1$-$C_{10}$)alkoxy, aryl, aryloxy, and heteroaryl;

R5 and R8 are each independently —H, or ($C_1$-$C_{10}$)alkyl, ($C_1$-$C_{10}$)alkoxy, ($C_2$-$C_6$)alkynyl, ($C_2$-$C_6$)alkenyl, ($C_3$-$C_7$)cycloalkyl, ($C_3$-$C_7$)cycloalkyl-($C_1$-$C_{10}$)alkyl, heteroaryl, ($C_1$-$C_{10}$)alkyl-heteroaryl, or aryl, each of which may be optionally substituted by one or more substituents selected from the group consisting of a halogen atom, —OH, oxo (═O), —SH, —$NO_2$, —CN, —$CONH_2$, ($C_1$-$C_{10}$)alkylsulfanyl, ($C_1$-$C_{10}$)alkylsulfinyl, ($C_1$-$C_{10}$)alkylsulfonyl, ($C_1$-$C_{10}$)alkyl, ($C_1$-$C_{10}$) alkylcarboxyl, ($C_1$-$C_{10}$)alkoxy, aryl, aryloxy, and heteroaryl;

or a pharmaceutically acceptable salt thereof.

2. A compound or salt according to claim 1, wherein G is selected from the group consisting of —OC(O)—, —$SO_2$—, and —C(O)—, R1 is selected from the group consisting of linear or branched ($C_1$-$C_{10}$)alkyl, aryl, ($C_3$-$C_8$)cycloalkyl, aryl($C_1$-$C_6$)alkyl, ($C_2$-$C_6$)alkenyl, ($C_5$-$C_{10}$)heterocycloalkyl, and heteroaryl, each of which may be optionally substituted by one or more substituents selected from a halogen atom, —N(R5)(R8), ($C_1$-$C_{10}$)alkyl, ($C_1$-$C_{10}$)alkylcarboxyl, ($C_1$-$C_{10}$)alkoxy, aryloxy, and heteroaryl, and R2 is H.

3. A compound or salt according to claim 2, wherein R1 is selected from the group consisting of methyl, ethyl, methoxyethoxyl, tert-butyl, ethenyl, cyclohexyl, phenyl, methoxyphenyl, chlorophenyl, difluorophenyl, dimethylthiazole, trifluoroethyl, phenylethyl, cyclopentyl, methylethoxyl, oxophenylethyl, thiophenyl, thiazolyl, fluorophenyl, aminophenyl, tert-butoxycarbonylamino-phenyl, and methylphenyl.

4. A compound or salt according to claim 1, wherein R3 is selected from the group consisting of ($C_1$-$C_{10}$)alkyl, aryl, and heteroaryl, each of which may be optionally substituted by one or more groups selected from a halogen atom, ($C_1$-$C_{10}$) alkyl, ($C_1$-$C_{10}$)alkoxy, and aryl($C_1$-$C_{10}$)alkylenoxy.

5. A compound or salt according to claim 1, wherein R6 is a residue of formula (i), R4 is a group of formula (Y) wherein p is 0, 1, and 3, P is CO, q is 0, and W is selected from the group consisting of ($C_1$-$C_{10}$)alkyl, aryl, heteroaryl, and ($C_5$-$C_{10}$)heterocycloalkyl, each of which may be optionally substituted by one or more substituents selected from the group consisting of a halogen atom, ($C_1$-$C_{10}$)alkyl, ($C_1$-$C_{10}$)alkoxy, —OH, and ($C_1$-$C_{10}$)alkylcarboxyl.

6. A compound or salt according to claim 5, wherein W is selected from the group consisting of phenyl, benzothioxol, thiophenyl and thiazolyl, each of which may be optionally substituted by one or more substituents selected from the group consisting of a halogen atom, —OH, methyl, and methylcarboxyl.

7. A pharmaceutical composition, comprising a compound or salt according to claim 1 and one or more pharmaceutically acceptable carriers and/or excipients.

8. A combination of a compound or salt according to claim 1 and one or more active ingredients selected from the group consisting of a beta2-agonist, a corticosteroid, a P38 MAP kinase inhibitor, a IKK2 inhibitor, a HNE inhibitor, a PDE4 inhibitor, a leukotriene modulator, a NSAID, and a mucus regulator.

9. A pharmaceutical composition according to claim 7, which is in a form suitable to be administered by inhalation.

10. A pharmaceutical composition according to claim 9, which is an inhalable powder, a propellant-containing metering aerosol, or a propellant-free inhalable formulation.

11. A device, which comprises a pharmaceutical composition according to claim 9.

12. A device according to claim 11, which is a single-dose dry powder inhaler, a multi-dose dry powder inhaler, a metered dose inhaler, or a soft mist nebulizer.

* * * * *